(12) United States Patent
Ichikawa et al.

(10) Patent No.: US 8,906,589 B2
(45) Date of Patent: Dec. 9, 2014

(54) SALT AND PHOTORESIST COMPOSITION COMPRISING THE SAME

(75) Inventors: Koji Ichikawa, Toyonaka (JP); Hiromu Sakamoto, Ibaraki (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 327 days.

(21) Appl. No.: 13/027,344

(22) Filed: Feb. 15, 2011

(65) Prior Publication Data

US 2011/0200940 A1 Aug. 18, 2011

(30) Foreign Application Priority Data

Feb. 18, 2010 (JP) ................. 2010-033422

(51) Int. Cl.

| | | |
|---|---|---|
| G03F 7/004 | (2006.01) | |
| G03F 7/028 | (2006.01) | |
| G03F 7/26 | (2006.01) | |
| C08F 18/20 | (2006.01) | |
| C07C 309/06 | (2006.01) | |
| C08F 212/14 | (2006.01) | |
| G03F 7/029 | (2006.01) | |
| C07C 25/18 | (2006.01) | |
| C07C 309/12 | (2006.01) | |
| C07C 309/17 | (2006.01) | |
| C07C 381/12 | (2006.01) | |
| C07D 333/46 | (2006.01) | |
| G03F 7/039 | (2006.01) | |

(52) U.S. Cl.
CPC ............. *C08F 212/14* (2013.01); *C07C 309/06* (2013.01); *G03F 7/029* (2013.01); *C07C 25/18* (2013.01); *C07C 309/12* (2013.01); *C07C 309/17* (2013.01); *C07C 381/12* (2013.01); *C07D 333/46* (2013.01); *G03F 7/0045* (2013.01); *G03F 7/0046* (2013.01); *G03F 7/0397* (2013.01); *Y10S 430/122* (2013.01); *Y10S 430/126* (2013.01)
USPC ........ 430/270.1; 430/921; 430/925; 430/322; 526/245; 568/22; 568/24

(58) Field of Classification Search
USPC ............... 430/270.1, 326, 921, 925; 526/243, 526/245; 560/15, 85; 549/78; 568/22, 24
See application file for complete search history.

(56) References Cited

U.S. PATENT DOCUMENTS

| | | | |
|---|---|---|---|
| 8,048,610 B2 * | 11/2011 | Ohsawa et al. | ............ 430/270.1 |
| 8,105,748 B2 * | 1/2012 | Ohashi et al. | ............... 430/270.1 |
| 2003/0099900 A1 | 5/2003 | Yamada et al. | |
| 2010/0055608 A1 * | 3/2010 | Ohashi et al. | ............... 430/270.1 |
| 2010/0075257 A1 | 3/2010 | Takemoto et al. | |
| 2011/0183263 A1 * | 7/2011 | Takahashi et al. | ......... 430/270.1 |

* cited by examiner

*Primary Examiner* — Anca Eoff
(74) *Attorney, Agent, or Firm* — Birch, Stewart, Kolasch & Birch, LLP

(57) ABSTRACT

The present invention provides a salt represented by the formula (I):

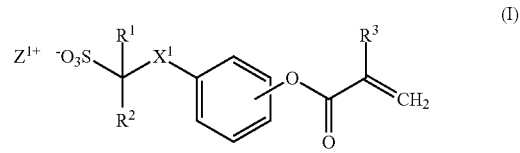

wherein $R^1$ and $R^2$ each independently represent a fluorine atom or a C1-C6 perfluoroalkyl group, $X^1$ represents a C1-C17 divalent saturated hydrocarbon group in which one or more —$CH_2$— can be replaced by —O— or —CO— and which can have one or more fluorine atoms, $R^3$ represents a hydrogen atom or a methyl group, and $Z^{1+}$ represents an organic counter cation, and a photoresist composition containing the same.

9 Claims, No Drawings

SALT AND PHOTORESIST COMPOSITION COMPRISING THE SAME

This nonprovisional application claims priority under 35 U.S.C. §119(a) on Patent Application No. 2010-033422 filed in JAPAN on Feb. 18, 2010, the entire contents of which are hereby incorporated by reference.

FIELD OF THE INVENTION

The present invention relates to a salt and photoresist composition comprising the same.

BACKGROUND OF THE INVENTION

A photoresist composition is used for semiconductor microfabrication employing a lithography process.

US 2003/0099900 A1 discloses a chemically amplified photoresist composition comprising a resin comprising a structural unit derived from 2-ethyl-2-adamantyl methacrylate and a structural unit derived from p-hydroxystyrene, triphenylsulfonium 2,4,6-triisopropylbenzenesulfonate and bis(cyclohexylsulfonyl)diazomethane as an acid generator, a basic compound and a solvent.

SUMMARY OF THE INVENTION

The present invention is to provide a salt for suitable for an acid generator and a photoresist composition comprising the same.

The present invention relates to the followings:
<1> A salt represented by the formula (I):

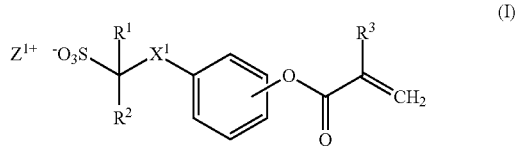

wherein $R^1$ and $R^2$ each independently represent a fluorine atom or a C1-C6 perfluoroalkyl group, $X^1$ represents a C1-C17 divalent saturated hydrocarbon group in which one or more —$CH_2$— can be replaced by —O— or —CO— and which can have one or more fluorine atoms, $R^3$ represents a hydrogen atom or a methyl group, and $Z^{1+}$ represents an organic counter cation;
<2> The salt according to <1>, wherein $X^1$ is *—CO—O— or *—$CH_2$—O—CO— in which * represents a binding position to —$C(R^1)(R^2)$—;
<3> The salt according to <1> or <2>, wherein $Z^{1+}$ is a triarylsulfonium cation;
<4> An acid generator comprising the salt according to any one of <1> to <3>;
<5> A polymer comprising a structural unit derived from the salt according to any one of <1> to <3>;
<6> A photoresist composition comprising the acid generator according to <4> and a resin having an acid-labile group, being insoluble or poorly soluble in an aqueous alkali solution but becoming soluble in an aqueous alkali solution by the action of an acid;
<7> A photoresist composition comprising the polymer according to <5>;
<8> The photoresist composition according to <6> or <7>, which further comprises a basic compound;
<9> A process for producing a photoresist pattern comprising the following steps (1) to (5):
(1) a step of applying the photoresist composition according to any one of <6> to <8> on a substrate,
(2) a step of forming a photoresist film by conducting drying,
(3) a step of exposing the photoresist film to radiation,
(4) a step of baking the exposed photoresist film, and
(5) a step of developing the baked photoresist film with an alkaline developer, thereby forming a photoresist pattern.

DESCRIPTION OF PREFERRED EMBODIMENTS

First, the salt represented by the formula (I) will be illustrated.

The salt of the present invention is represented by the formula (I)

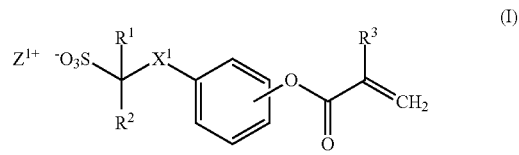

wherein $R^1$ and $R^2$ each independently represent a fluorine atom or a C1-C6 perfluoroalkyl group, $X^1$ represents a C1-C17 divalent saturated hydrocarbon group in which one or more —$CH_2$— can be replaced by —O— or —CO— and which can have one or more fluorine atoms, $R^3$ represents a hydrogen atom or a methyl group, and $Z^{1+}$ represents an organic counter cation (hereinafter, simply referred to as SALT (I)).

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $R^1$ and $R^2$ independently preferably represent a fluorine atom or a trifluoromethyl group, and $R^1$ and $R^2$ are more preferably fluorine atoms.

Examples of the C1-C17 divalent saturated hydrocarbon group include a C1-C17 linear alkanediyl group such as a methylene group, an ethylene group, a propane-1,3-diyl group, a propane-1,2-diyl group, a butane-1,4-diyl group, a butane-1,3-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,1-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group; a C2-C17 branched alkanediyl group such as a 1-methyl-1,3-propylene group, a 2-methyl-1,3-propylene group, a 2-methyl-1,2-propylene group, a 1-methyl-1,4-butylene group, and a 2-methyl-1,4-butylene group; a divalent monocyclic saturated hydrocarbon group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group; a divalent polycyclic saturated hydrocarbon group such as a norbornane-2,3-diyl group, a norbornane-1,4-diyl group, a norbornane-2,5-diyl group, an adamantane-1,2-diyl group, an adamantane-1,5-diyl group and an adamantane-2, 6-diyl group; and a group formed by combining two or more groups selected from the group consisting of the above-mentioned groups.

Examples of the C1-C17 divalent saturated hydrocarbon group in which one or more —CH$_2$— are replaced by —O— or —CO— include *—CO—O-L$^{b2}$-, *—CO—O-L$^{b4}$-CO—O-L$^{b3}$-, *-L$^{b5}$-O—CO—, *-L$^{b7}$-O-L$^{b6}$-, *—CO—O-L$^{b8}$-O—, and *—CO—O-L$^{b10}$-O-L$^{b9}$-CO—O—, wherein L$^{b2}$ represents a single bond or a C1-C15 saturated hydrocarbon group, L$^{b3}$ represents a single bond or a C1-C12 saturated hydrocarbon group, L$^{b4}$ represents C1-C13 saturated hydrocarbon group, with the proviso that total carbon number of L$^{b3}$ and L$^{b4}$ is 1 to 13, L$^{b5}$ represents a C1-C15 saturated hydrocarbon group, L$^{b6}$ represents a C1-C15 saturated hydrocarbon group, L$^{b7}$ represents a C1-C15 saturated hydrocarbon group, with the proviso that total carbon number of L$^{b6}$ and L$^{b7}$ is 1 to 16, L$^{b8}$ represents a C1-C14 saturated hydrocarbon group, L$^{b9}$ represents a C1-C11 saturated hydrocarbon group, L$^{b10}$ represents a C1-C11 saturated hydrocarbon group, with the proviso that total carbon number of L$^{b9}$ and L$^{b10}$ is 1 to 12, and * represents a binding position to —C(R$^1$)(R$^2$)—. Among them, preferred is *—CO—O-L$^{b2}$-, and more preferred is *—CO—O-L$^2$- in which L$^{b2}$ is a single bond or —CH$_2$—.

Examples of *—CO—O-L$^{b2}$- include *—CO—O— and *—CO—O—CH$_2$—. Examples of *—CO—O-L$^{b4}$-CO—O-L$^{b3}$- include *—CO—O—(CH$_2$)$_4$—CO—O—, *—CO—O—(CH$_2$)$_2$—CO—O—, *—CO—O—(CH$_2$)$_3$—CO—O—, *—CO—O—(CH$_2$)$_4$—CO—O—, *—CO—O—(CH$_2$)$_6$—CO—O—, *—CO—O—(CH$_2$)$_8$—CO—O—, *—CO—O—CH$_2$—CH(CH$_3$)—CO—O— and *—CO—O—CH$_2$—C(CH$_3$)$_2$—CO—O—. Examples of *-L$^{b5}$-O—CO— include *—CH$_2$—O—CO—, *—(CH$_2$)$_2$—O—CO—, *—(CH$_2$)$_3$—O—CO—, *—(CH$_2$)$_4$—O—CO— and *—(CH$_2$)$_6$—O—CO—. Examples of *-L$^{b7}$-O-L$^{b6}$- include *—CH$_2$—O—CH$_2$—. Examples of *—CO—O-L$^{b8}$-O— include *—CO—O—CH$_2$—O—, *—CO—O—(CH$_2$)$_2$—O—, *—CO—O—(CH$_2$)$_3$—O—, *—CO—O—(CH$_2$)$_4$—O— and *—CO—O—(CH$_2$)$_6$—O—. Examples of *—CO—O-L$^{b10}$-O-L$^{b9}$-CO—O— include the followings.

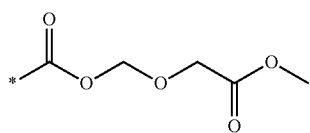

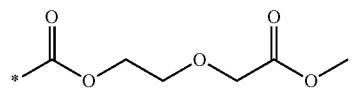

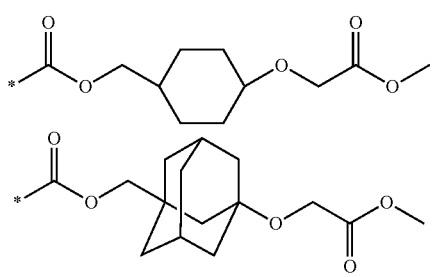

Examples of SALT (I) include the following.

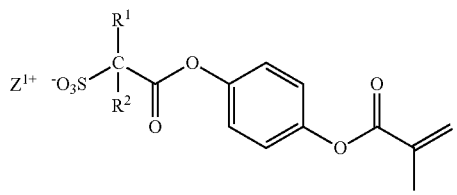

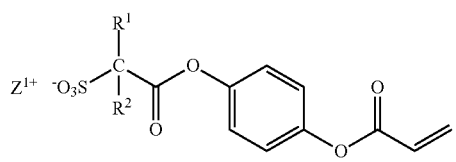

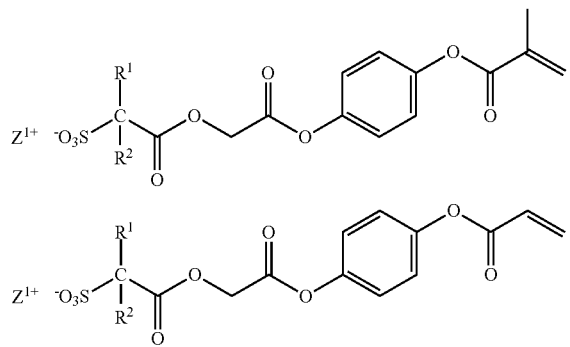

wherein R$^1$, R$^2$ and Z$^{1+}$; are the same as defined above.

Examples of the organic counter ion represented by Z$^{1+}$ include an onium cation such as a sulfonium cation, an iodonium cation, an ammonium cation, a benzothiazolium cation and a phosphonium cation, and a sulfonium cation and an iodonium cation are preferable, and an arylsulfonium cation is more preferable, and triarylsulfonium cation is especially preferable.

Preferable examples of the organic cation represented by Z$^{1+}$ include the cations represented by the formulae (b2-1) to (b2-4):

(b2-1)

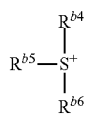

(b2-2)

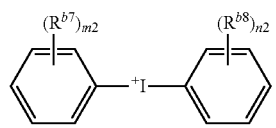

(b2-3)

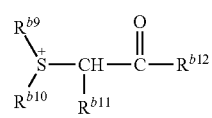

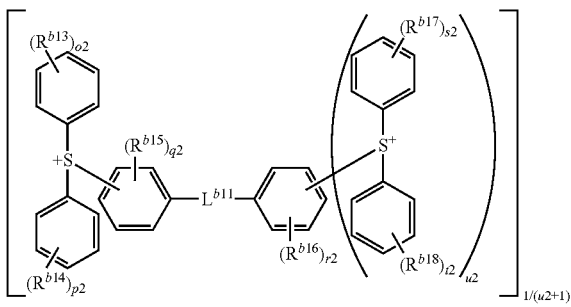

wherein $R^{b4}$, $R^{b5}$ and $R^{b6}$ independently represent a C1-C30 aliphatic hydrocarbon group which can have one or more substituents selected from the group consisting of a hydroxyl group, a C1-C12 alkoxy group and a C6-C18 aromatic hydrocarbon group, a C3-C18 saturated cyclic hydrocarbon group which can have one or more substituents selected from the group consisting of a halogen atom, a C2-C4 acyl group and a glycidyloxy group, or a C6-C18 aromatic hydrocarbon group which can have one or more substituents selected from the group consisting of a halogen atom, a hydroxyl group, a C1-C18 aliphatic hydrocarbon group, a C3-C18 saturated cyclic hydrocarbon group and a C1-C12 alkoxy group, $R^{b7}$ and $R^{b8}$ are independently in each occurrence a hydroxyl group, a C1-C12 aliphatic hydrocarbon group or a C1-C12 alkoxy group, m2 and n2 independently represents an integer of 0 to 5, $R^{b9}$ and $R^{b10}$ independently represent a C1-C18 aliphatic hydrocarbon group or a C3-C18 saturated cyclic hydrocarbon group, or $R^{b9}$ and $R^{10}$ are bonded to form a C2-C11 divalent acyclic hydrocarbon group which forms a ring together with the adjacent $S^+$, and one or more —$CH_2$— in the divalent acyclic hydrocarbon group may be replaced by —CO—, —O— or —S—, and $R^{b11}$ represents a hydrogen atom, a C10-C18 aliphatic hydrocarbon group, a C3-C18 saturated cyclic hydrocarbon group or a C6-C18 aromatic hydrocarbon group, $R^{b12}$ represents a C1-C12 aliphatic hydrocarbon group, a C3-C18 saturated cyclic hydrocarbon group or a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and a C2-C13 acyloxy group, or $R^{b11}$ and $R^{b12}$ are bonded each other to form a C1-C10 divalent acyclic hydrocarbon group which forms a 2-oxocycloalkyl group together with the adjacent —CHCO—, and one or more —$CH_2$— in the divalent acyclic hydrocarbon group may be replaced by —CO—, —O— or —S—, and $R^{b13}$, $R^{b14}$, $R^{b15}$, $R^{b16}$, $R^{b17}$ and $R^{b18}$ independently represent a hydroxyl group, a C1-C12 aliphatic hydrocarbon group or a C1-C12 alkoxy group, $L^{b11}$ represents —S— or —O— and o2, p2, s2 and t2 each independently represents an integer of 0 to 5, q2 and r2 each independently represents an integer of 0 to 4, and u2 represents 0 or 1.

The aliphatic hydrocarbon group represented by $R^{b9}$ to $R^{b11}$ has preferably 1 to 12 carbon atoms. The saturated cyclic hydrocarbon group represented by $R^{b9}$ to $R^{b11}$ has preferably 3 to 18 carbon atoms and more preferably 4 to 12 carbon atoms.

Preferable examples of the aliphatic hydrocarbon group include an alkyl group such as a methyl group, an ethyl group, a propyl group, an isopropyl group, a butyl group, a sec-butyl group, a tert-butyl group, a pentyl group, a hexyl group, an octyl group and a 2-ethylhexyl group. Preferable examples of the saturated cyclic hydrocarbon group include a cyclopropyl group, a cyclobutyl group, a cyclopentyl group, a cyclohexyl group, a cycloheptyl group, a cyclodecyl group, a 2-alkyl-a-adamantyl group, a 1-(1-adamantyl)-1-alkyl group and an isobornyl group. Preferable examples of the aromatic group include a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group. Examples of the aliphatic hydrocarbon group having an aromatic hydrocarbon group include a benzyl group. Examples of the alkoxy group include a methoxy group, an ethoxy group, a propoxy group, an isopropoxy group, a butoxy group, a sec-butoxy group, a tert-butoxy group, a pentyloxy group, a hexyloxy group, a heptyloxy group, an octyloxy group, a 2-ethylhexyloxy group, a nonyloxy group, a decyloxy group, an undecyloxy group and a dodecyloxy group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent $S^+$ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

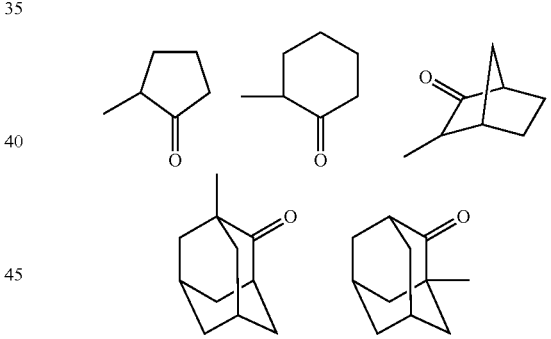

A C1-C5 divalent acyclic hydrocarbon group is preferable.

Among the above-mentioned cations, preferred is the cation represented by the formula (b2-1), and more preferred is the cation represented by the formula (b2-1-1). A triphenylsulfonium cation is especially preferable.

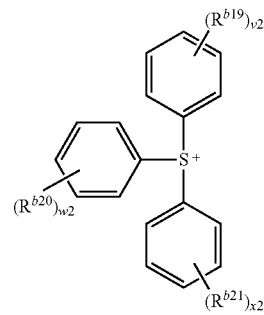

(b2-1-1)

wherein $R^{b19}$, $R^{b20}$ and $R^{b21}$ are independently in each occurrence a halogen atom (preferably a fluorine atom), a hydroxyl group, a C1-C18 aliphatic hydrocarbon group, a C3-C18 saturated cyclic hydrocarbon group or a C1-C12 alkoxy group, and one or more hydrogen atoms of the aliphatic hydrocarbon group can be replaced by a hydroxyl group, a C1-C12 alkoxy group or a C6-C18 aromatic hydrocarbon group, and one or more hydrogen atoms of the saturated cyclic hydrocarbon group can be replaced by a halogen atom, a glycidyloxy group or a C2-C4 acyl group, and v2, w2 and x2 independently each represent an integer of 0 to 5.

The aliphatic hydrocarbon group has preferably 1 to 12 carbon atoms, and the saturated cyclic hydrocarbon group has preferably 4 to 18 carbon atoms, and v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5. It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the cation represented by the formula (b2-1) include the following.

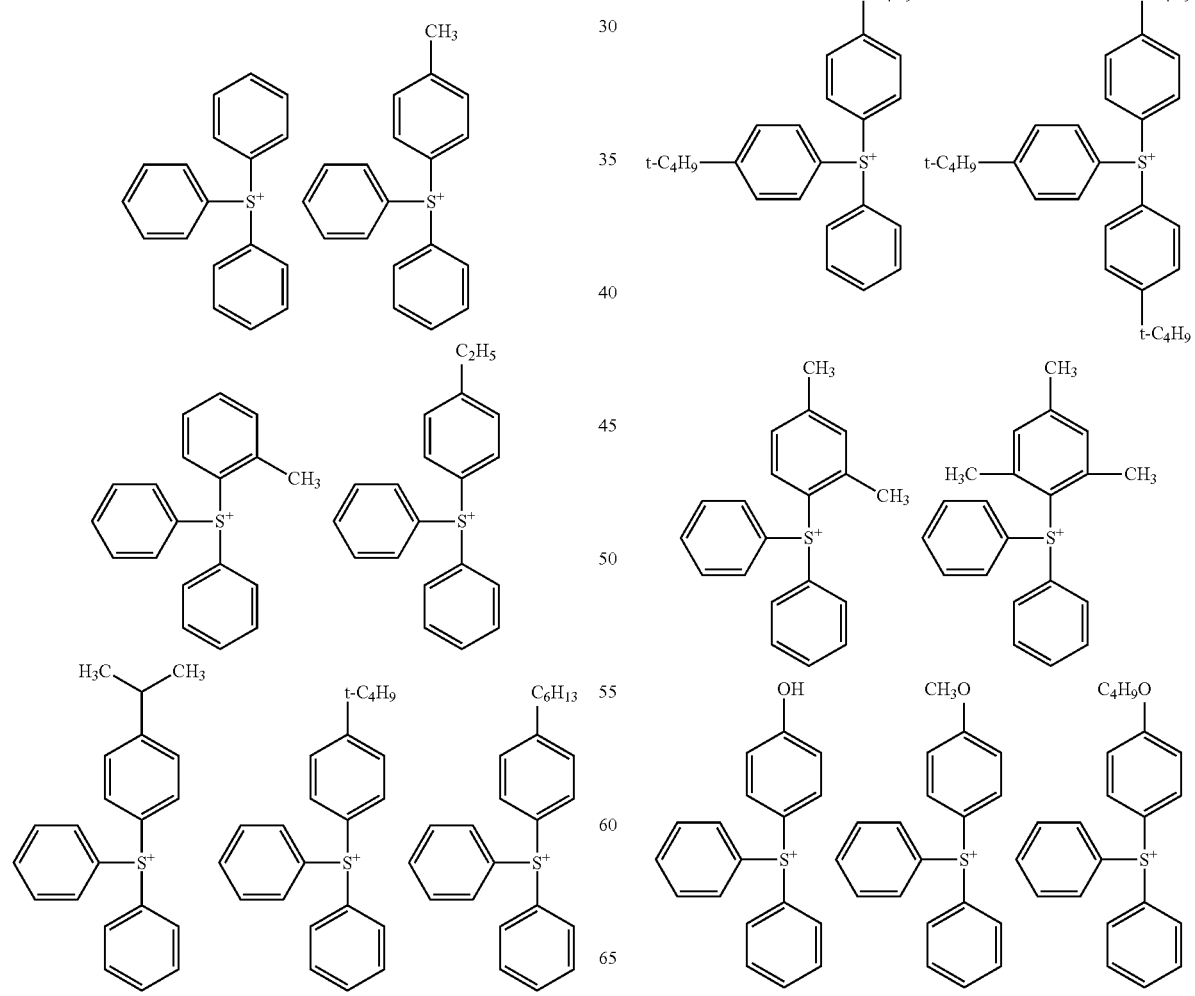

-continued
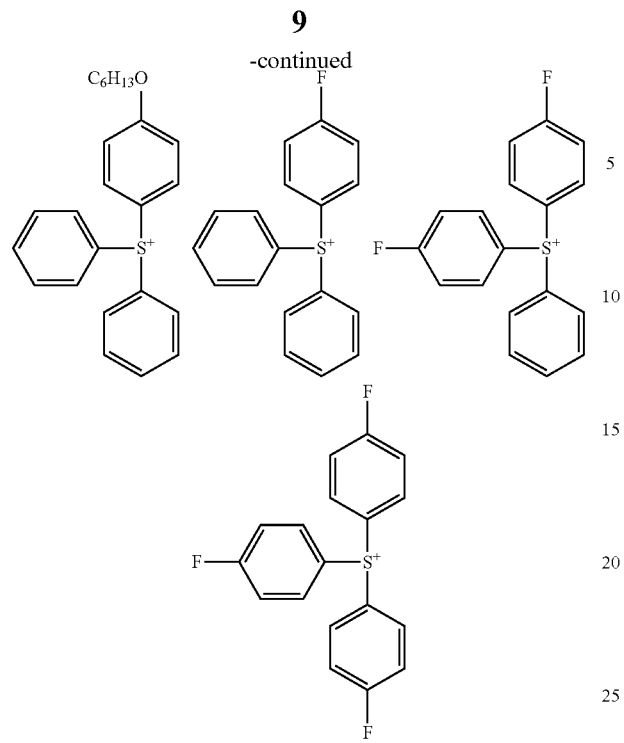
Examples of the cation represented by the formula (b2-2) include the followings.
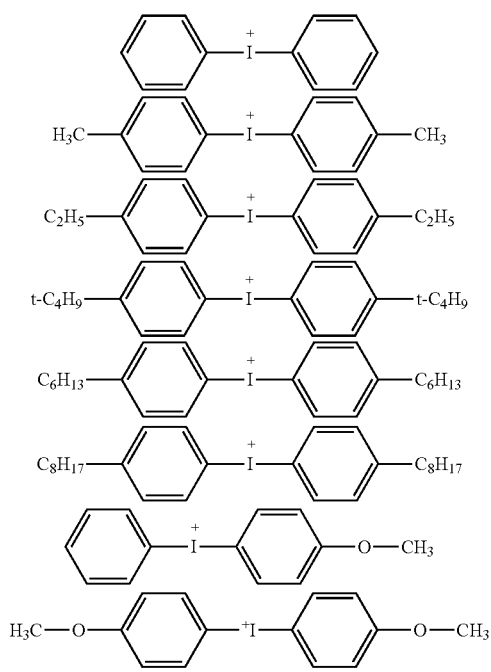
Examples of the cation represented by the formula (b2-3) include the followings.
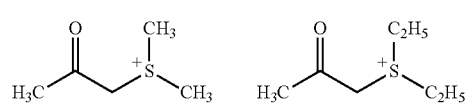
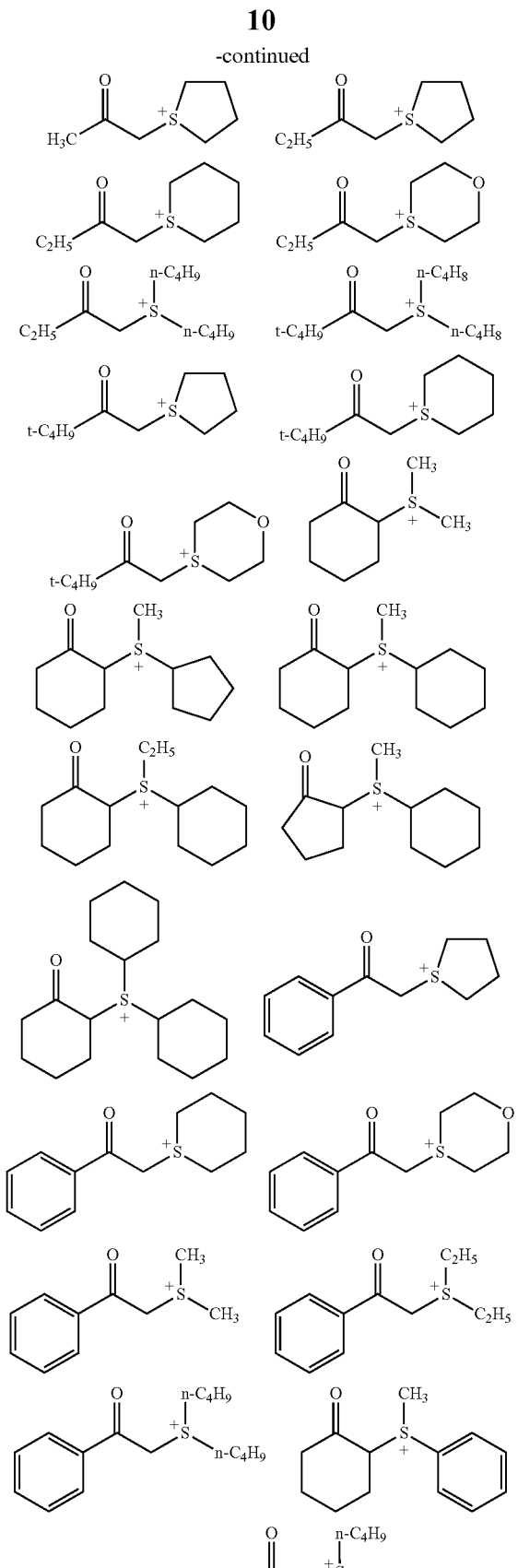
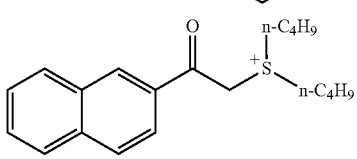

-continued
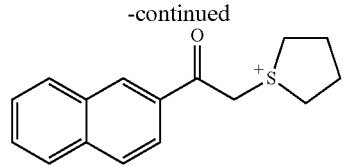
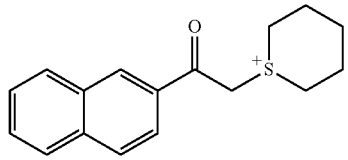
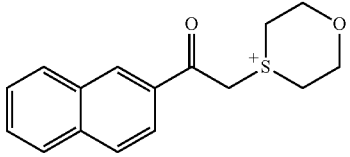
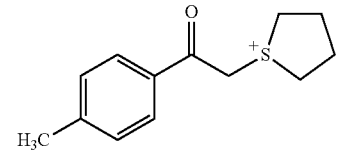
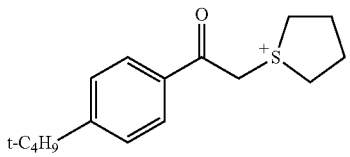
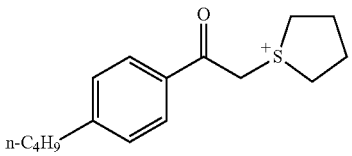
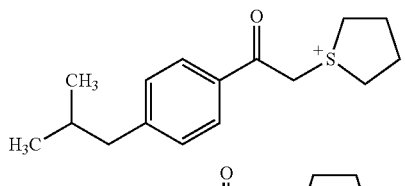
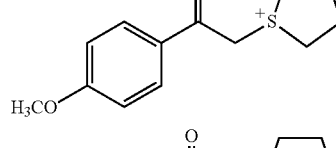
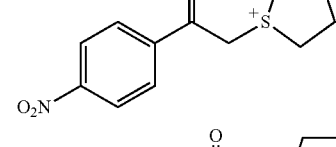
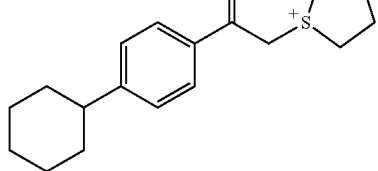
-continued
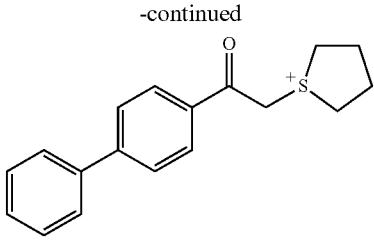
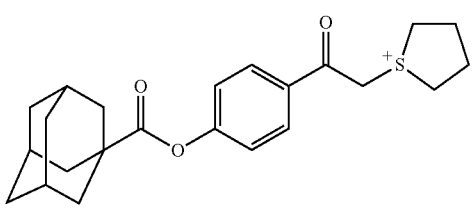
Examples of the cation represented by the formula (b2-4) include the followings.
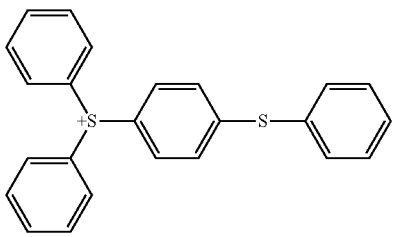
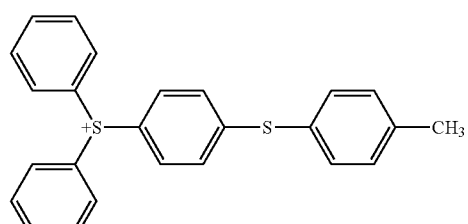
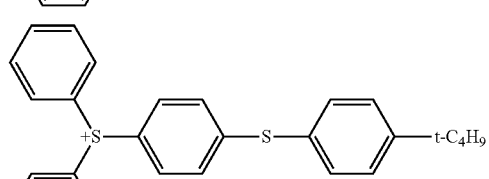
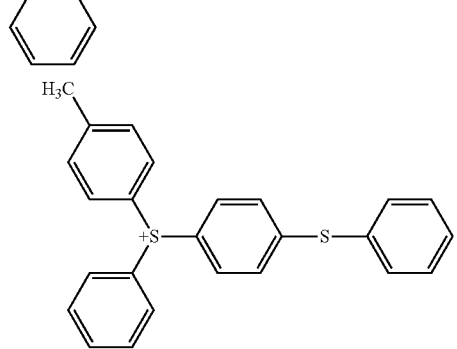

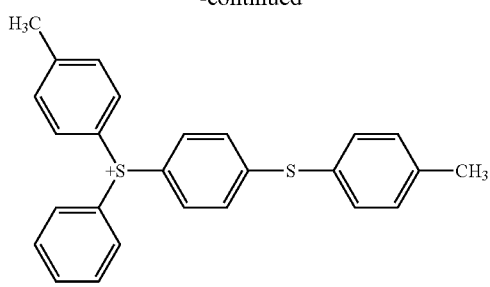
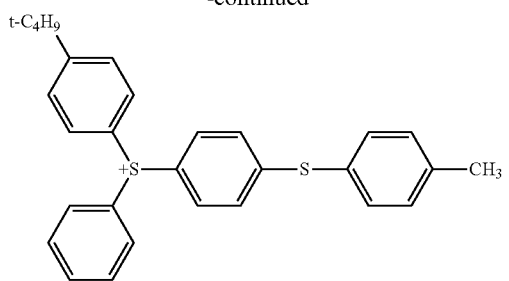
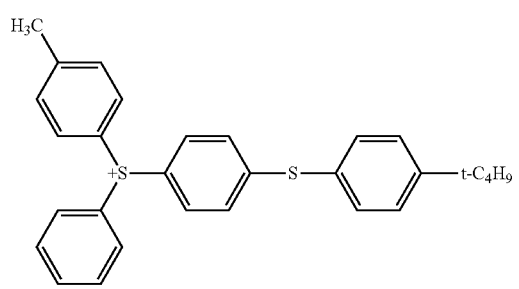
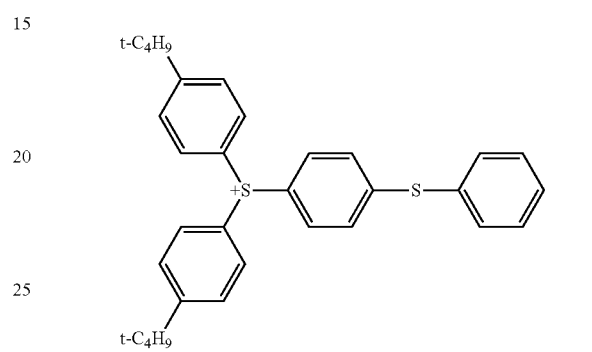
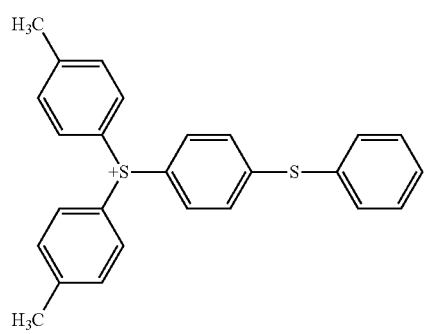
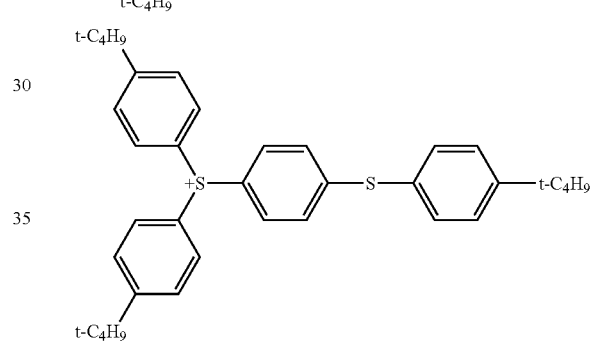
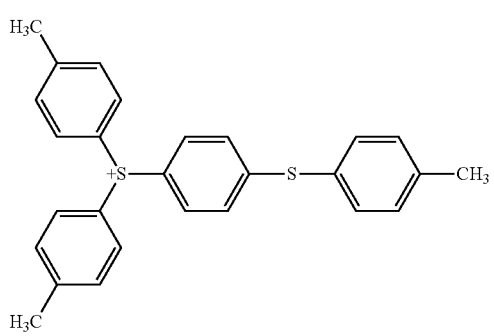
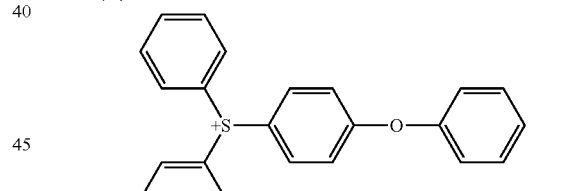
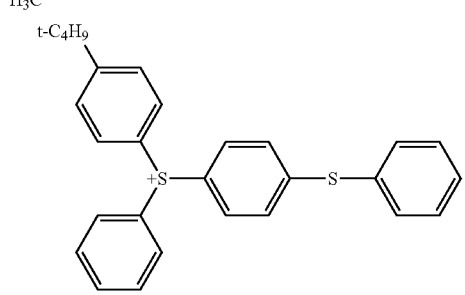
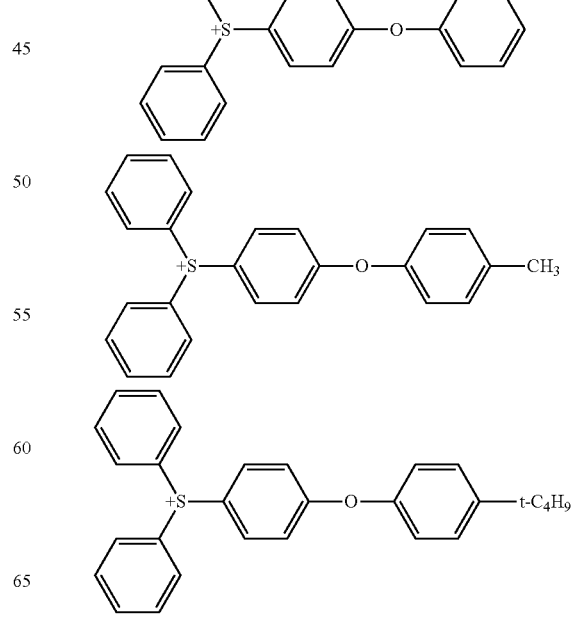

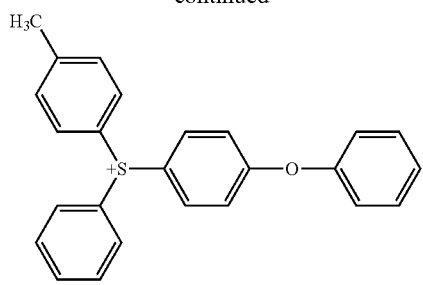
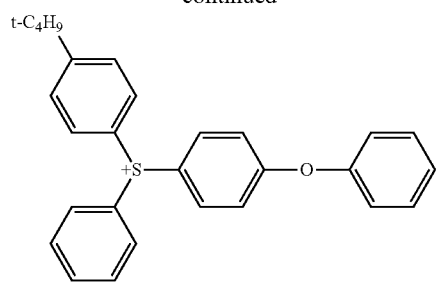
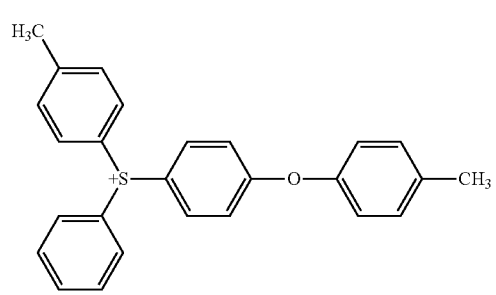
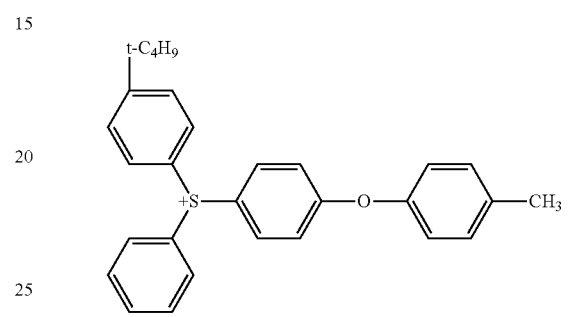
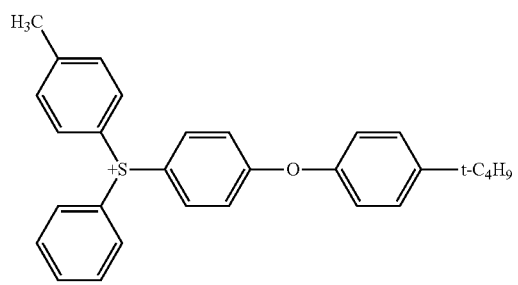
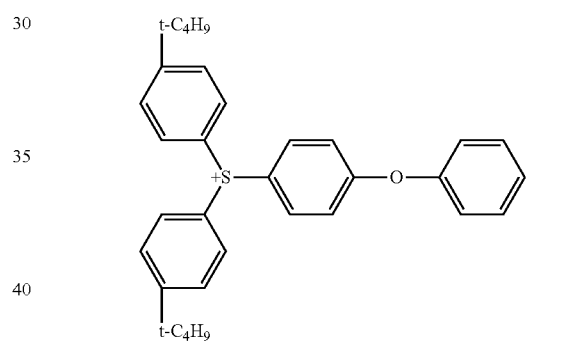
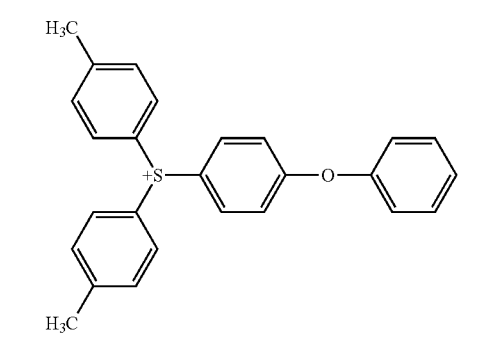
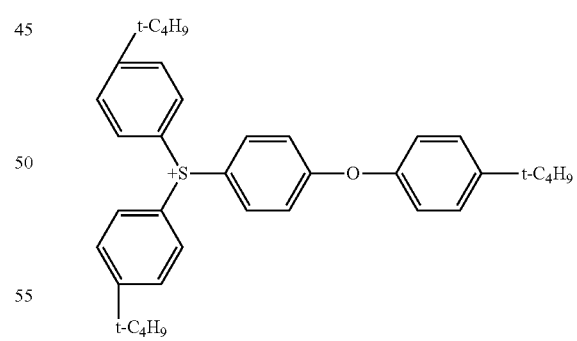
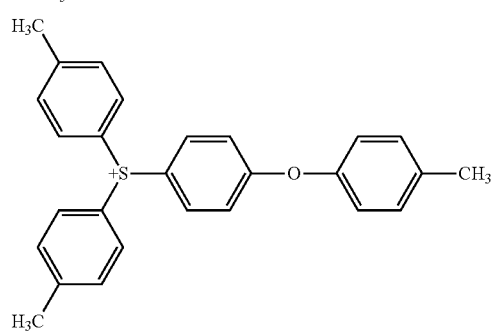
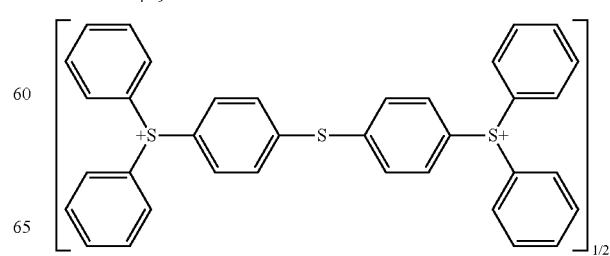

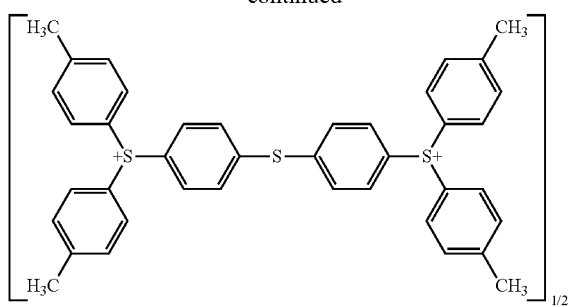
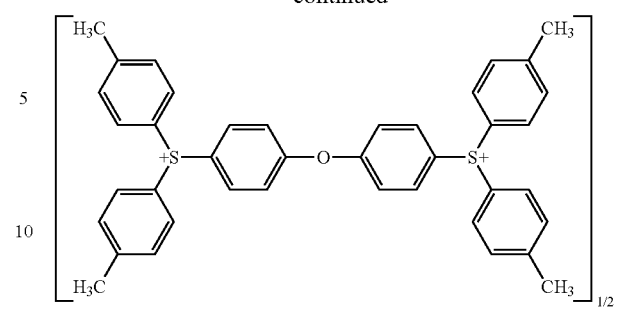
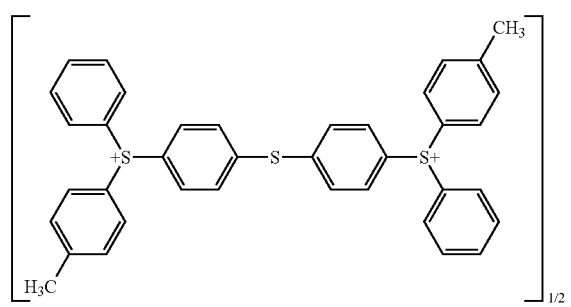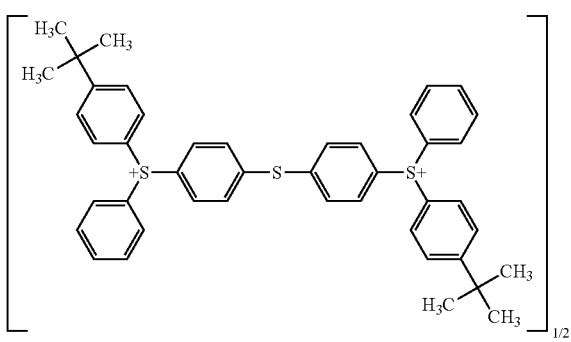
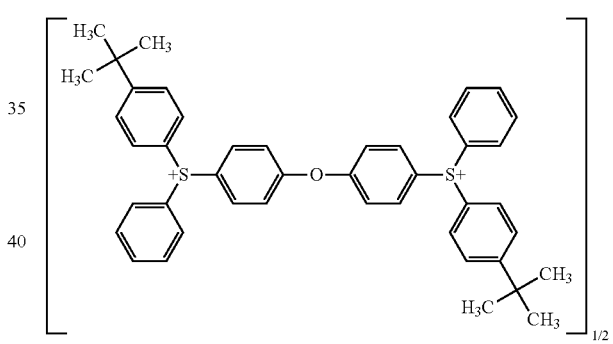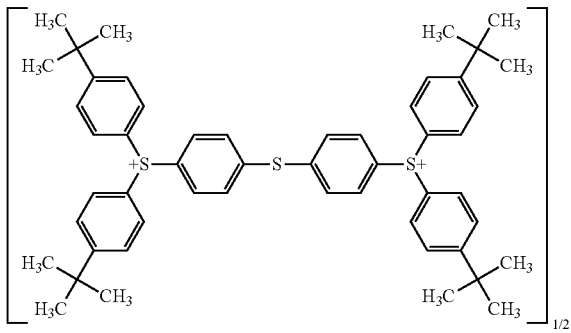
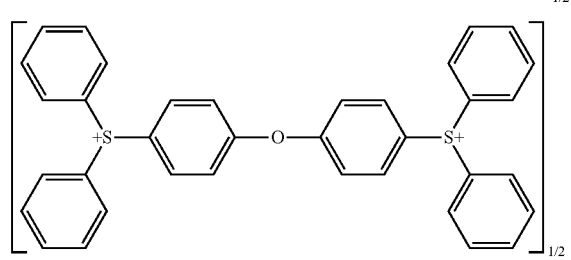
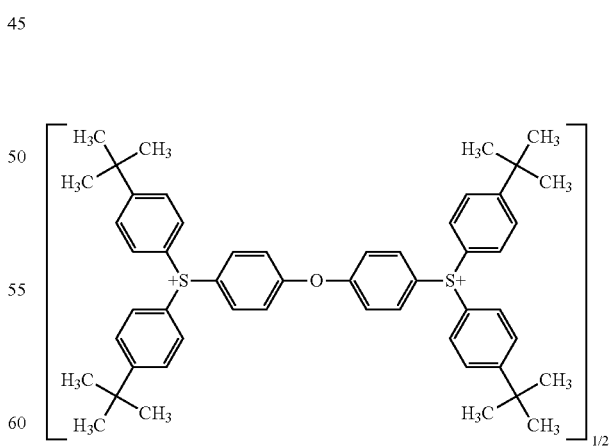
Examples of SALT (I) include a salt wherein the anion is any one of the above-mentioned anions and the cation is any one of organic cations. Preferable examples of SALT (I) include the following.

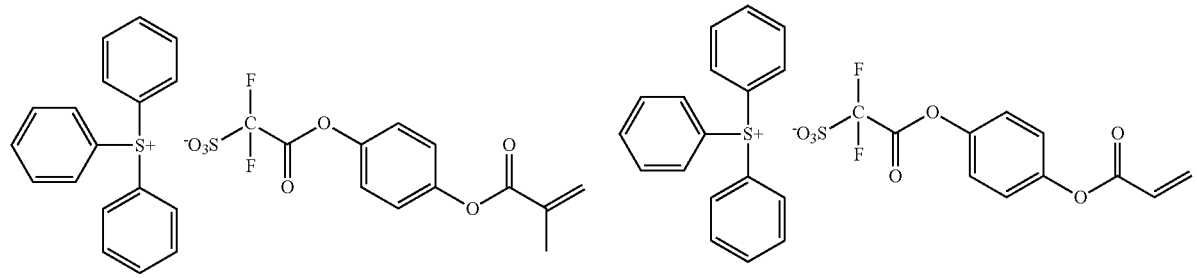
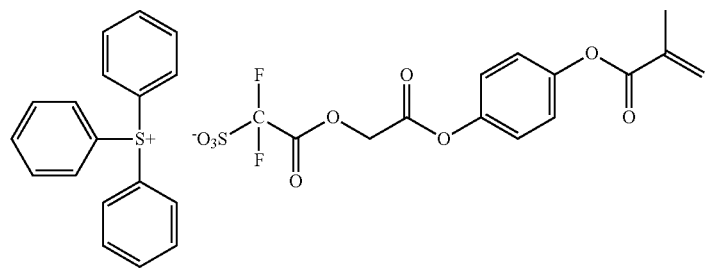
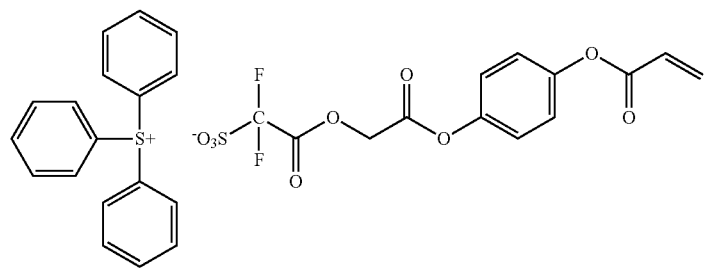
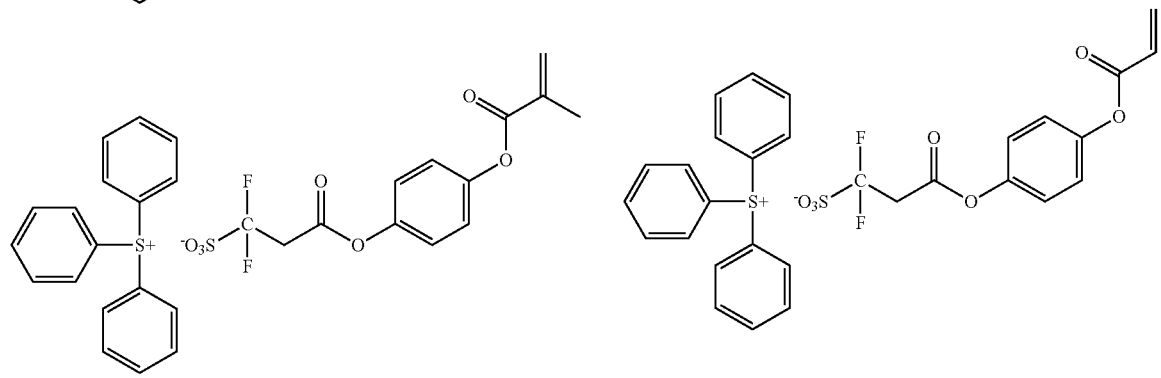
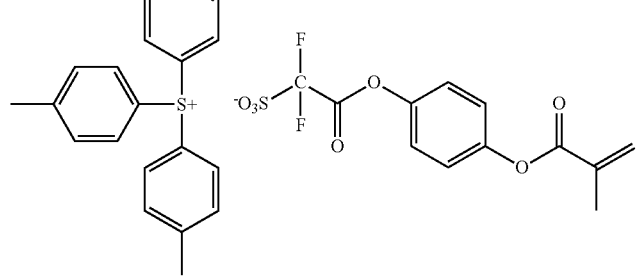

-continued
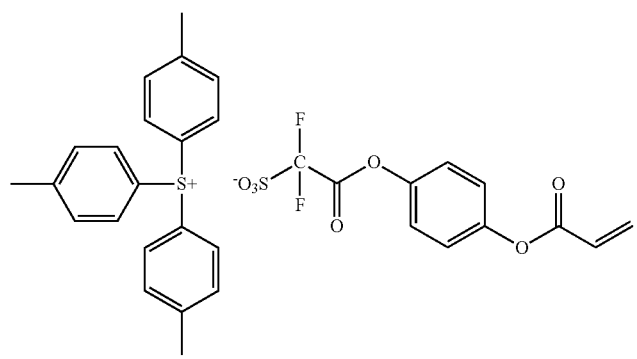
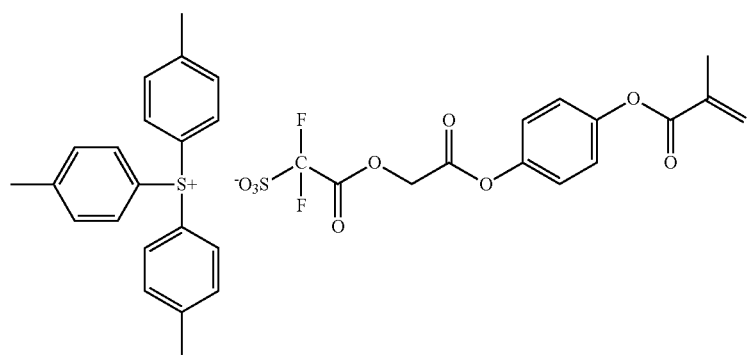
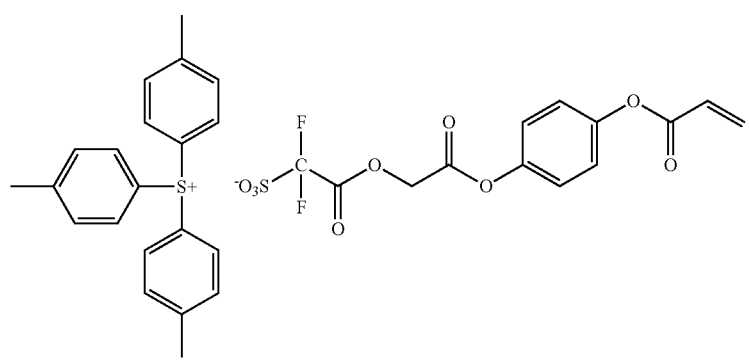
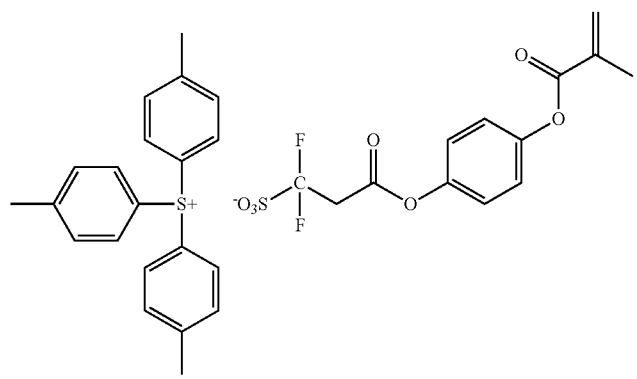

-continued
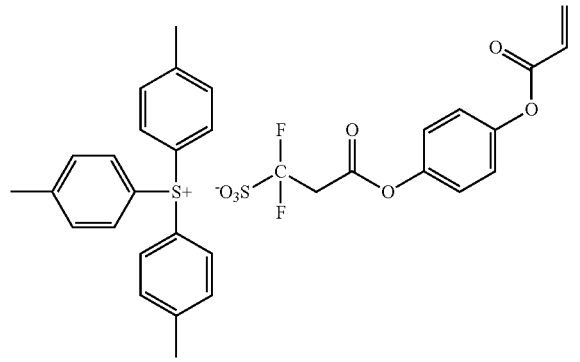
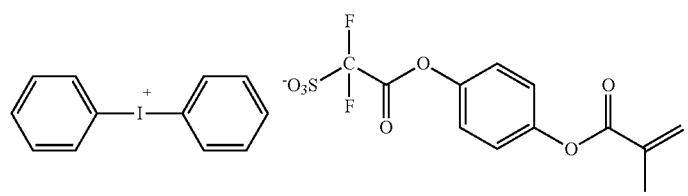
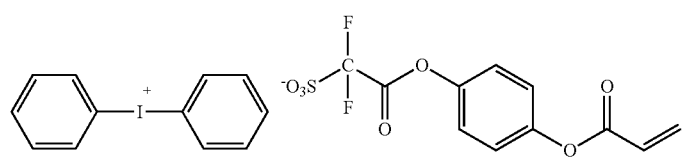
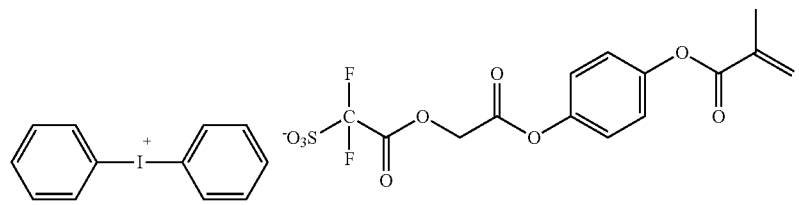
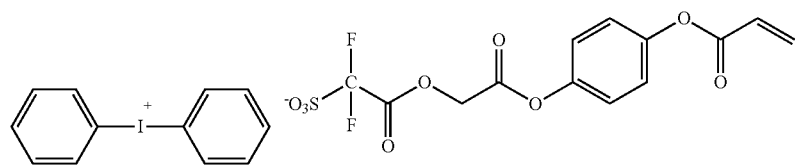
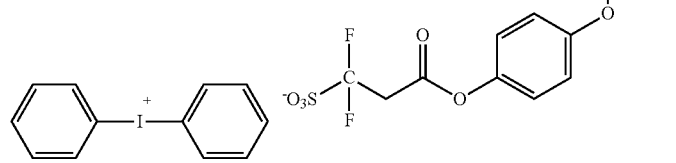
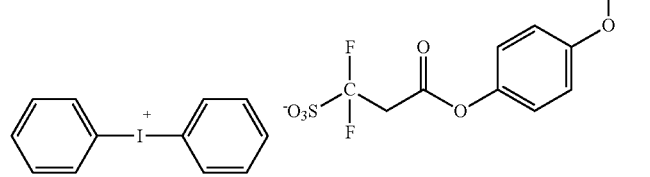

-continued
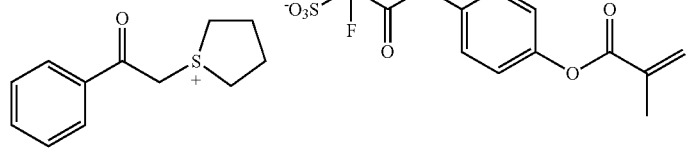
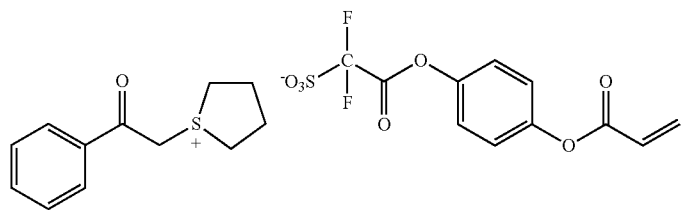
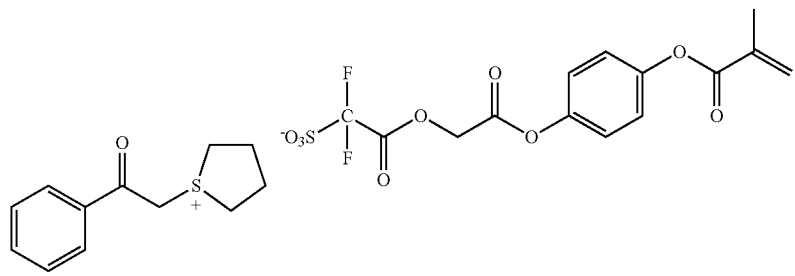
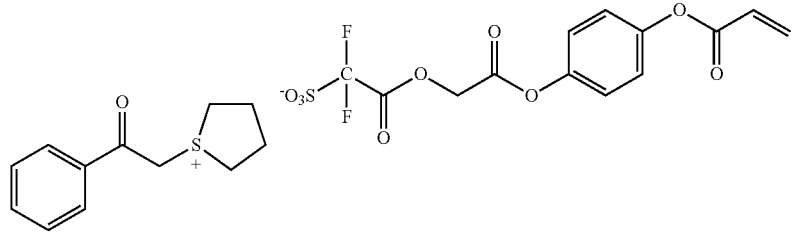
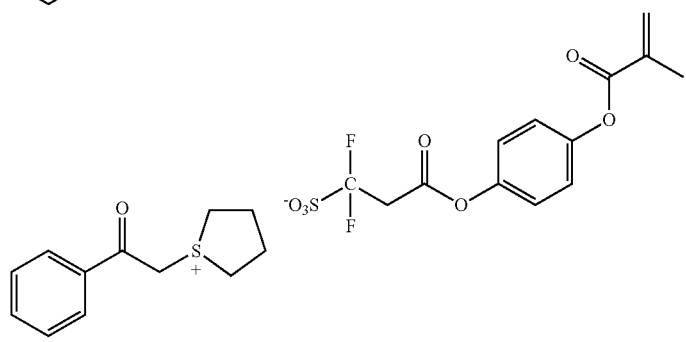
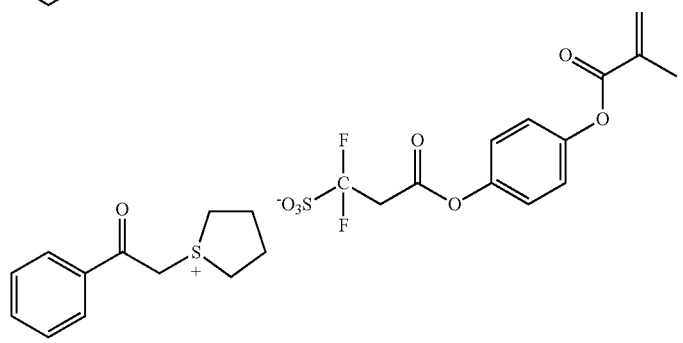

The process for producing SALT (I) will be illustrated.

For example, a salt represented by the formula (IA) can be produced by reacting a compound represented by the formula (IA-2) with a salt represented by the formula (IA-1) in a solvent such as acetonitrile.

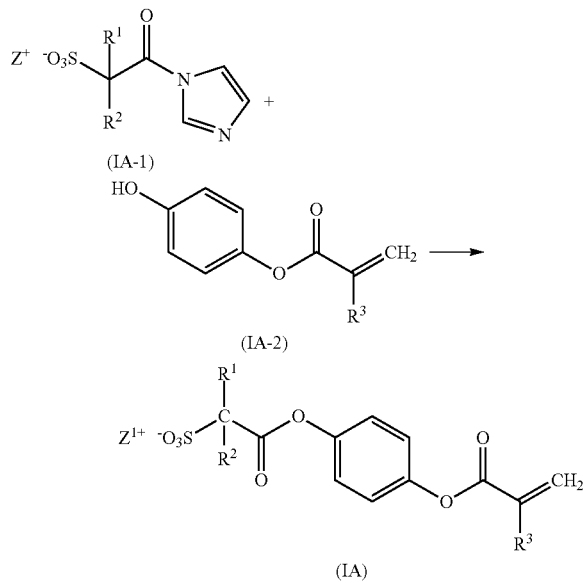

wherein $R^1$, $R^2$, $R^3$ and $Z^{1+}$ are the same as defined above.

Examples of the compound represented by the formula (IA-2) include p-hydroxyphenyl methacrylate.

The salt represented by the formula (IA-1) can be produced by reacting a salt represented by the formula (IA-3) with carbonyldiimidazole in a solvent such as acetonitrile.

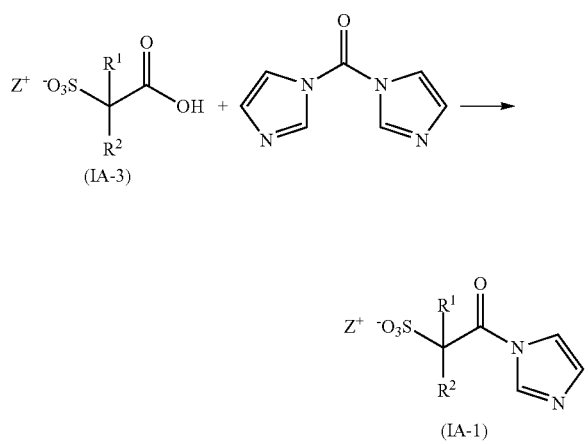

wherein $R^1$, $R^2$ and $Z^{1+}$ are the same as defined above.

The salt represented by the formula (IIA-3) can be produced according to the method described in JP 2008-127367 A.

For example, a salt represented by the formula (IB) can be produced by reacting a compound represented by the formula (IB-2) with a salt represented by the formula (IB-1) in a solvent such as acetonitrile.

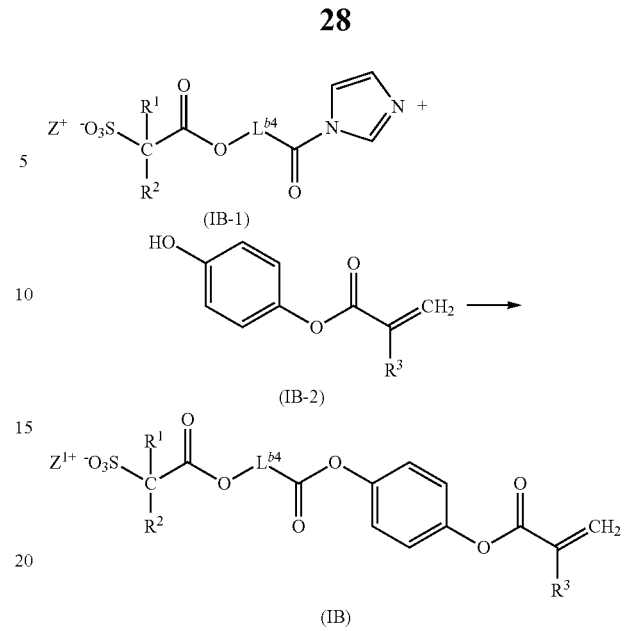

wherein $R^1$, $R^2$, $R^3$, $L^{b4}$ and $Z^{1+}$ are the same as defined above.

Examples of the compound represented by the formula (IB-2) include p-hydroxyphenyl methacrylate.

The salt represented by the formula (IB-1) can be produced by reacting a salt represented by the formula (IB-3) with carbonyldiimidazole in a solvent such as acetonitrile.

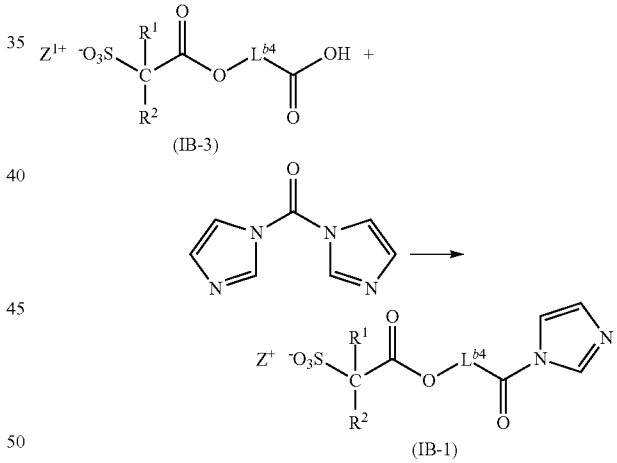

wherein $R^1$, $R^2$, $L^{b4}$ and $Z^{1+}$ are the same as defined above.

For example, a salt represented by the formula (IB-3) can be produced by reacting a salt represented by the formula (IB-5) with a compound represented by the formula (IB-6) in a solvent such as N,N-dimethylformamide in the presence of a catalyst such as potassium iodide and potassium carbonate.

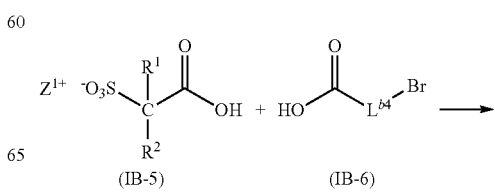

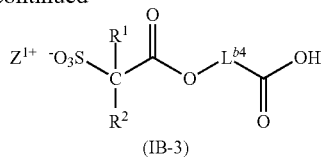

(IB-3)

wherein $R^1$, $R^2$, $L^{b4}$ and $Z^{1+}$ are the same as defined above.

Examples of the compound represented by the formula (IB-6) include bromoacetic acid, and examples of the salt represented by the formula (IB-5) can be produced according to the method described in JP 2008-127367 A.

Next, the polymer of the present invention will be illustrated

The polymer of the present invention (hereinafter, simply referred to as POLYMER (I)) comprises a structural unit derived from SALT (I). The structural unit derived from SALT (I) is represented by the following:

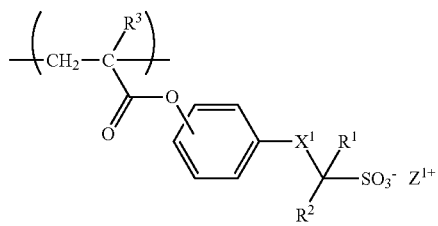

wherein $R^1$, $R^2$, $R^3$, $X^1$ and $Z^{1+}$ are the same as defined above.

POLYMER (I) can have two or more kinds of the structural unit derived from SALT (I).

POLYMER (I) can have one or more structural units derived from the monomers other than SALT (I).

POLYMER (I) can be produced by polymerizing SALT (I) or POLYMER (I) and other monomers in the presence of an initiator in an inert solvent such as 1,4-dioxane, tetrahydrofuran, acetonitrile and dichloroethane. Examples of the initiator include azobisisobutyronitrile, azobis(2,4-dimethylvaleronitrile) and benzoyl peroxide. The polymerization temperature is usually room temperature to 100° C., and preferably 60 to 80° C. POLYMER (I) can be isolated by charging the reaction mixture obtained into water, a polar solvent such as methanol or a nonpolar solvent such as hexane and heptane to cause a precipitation followed by collecting the precipitation by filtration.

The content of the structural unit derived from SALT (I) in POLYMER (I) is usually 3 to 100% by mole, preferably 4 to 50% by mole and more preferably 5 to 30% by mole.

POLYMER (I) is preferably a polymer being insoluble or poorly soluble in an alkali aqueous solution but becoming soluble in an alkali aqueous solution by the action of an acid. POLYMER (I) being insoluble or poorly soluble in an alkali aqueous solution but becoming soluble in an alkali aqueous solution by the action of an acid can be produced by polymerizing SALT (I) and one or more monomers having an acid-labile group (hereinafter, simply referred to as MONOMER (a1)). In this specification, "an acid-labile group" means a group capable of being eliminated by the action of an acid.

Examples of the acid-labile group include a group represented by the formula (I):

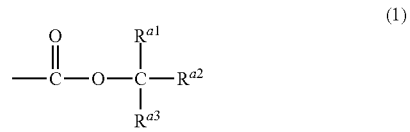

wherein $R^{a1}$, $R^{a2}$ and $R^{a3}$ independently each represent an aliphatic hydrocarbon group or a saturated cyclic hydrocarbon group, and $R^{a1}$ and $R^{a2}$ can be bonded each other to form a ring together with a carbon atom to which $R^{a1}$ and $R^{a2}$ are bonded.

Examples of the aliphatic hydrocarbon group include a C1-C8 alkyl group. Specific examples of the C1-C8 alkyl group include a methyl group, an ethyl group, a propyl group, an isopropyl group, a butyl group, a pentyl group, a hexyl group, a heptyl group and an octyl group. The saturated cyclic hydrocarbon group may be monocyclic or polycyclic, and preferably has 3 to 20 carbon atoms. Examples of the saturated cyclic hydrocarbon group include a monocyclic alicyclic hydrocarbon group such as a C3-C20 cycloalkyl group (e.g. a cyclopentyl group, a cyclohexyl group, a methylcyclohexyl group, a dimethylcyclohexyl group, a cycloheptyl group and a cyclooctyl group) and a polycyclic alicyclic hydrocarbon group such as a decahydronaphthyl group, an adamantyl group, a norbornyl group, a methylnorbornyl group, and the followings:

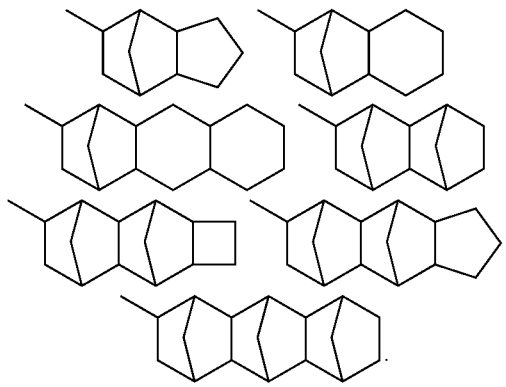

Examples of the ring formed by bonding $R^{a1}$ and $R^{a2}$ each other include the following groups and the ring preferably has 5 to 20 carbon atoms.

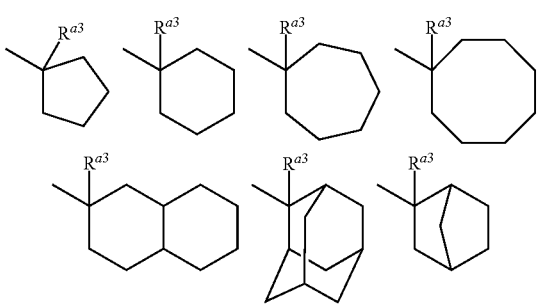

-continued

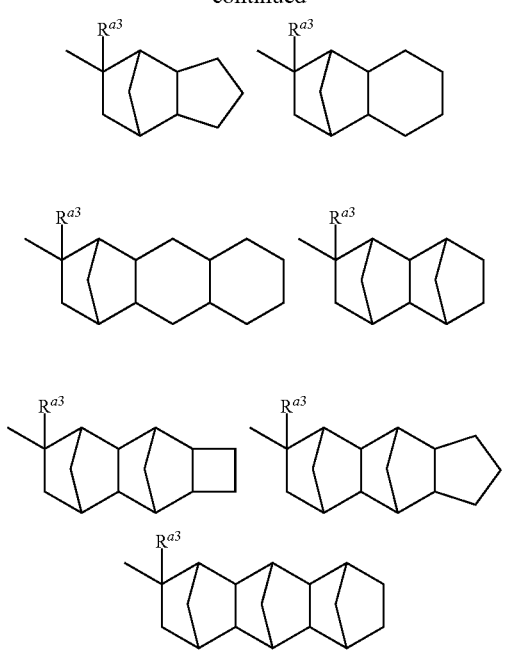

wherein R$^{a3}$ is the same as defined above.

The group represented by the formula (I) wherein R$^{a1}$, R$^{a2}$ and R$^{a3}$ independently each represent a C1-C8 alkyl group such as a tert-butyl group, the group represented by the formula (I) wherein R$^{a1}$ and R$^{a2}$ are bonded each other to form an adamantyl ring and R$^{a3}$ is a C1-C8 alkyl group such as a 2-alkyl-2-adamantyl group, and the group represented by the formula (I) wherein R$^{a1}$ and R$^{a2}$ are C1-C8 alkyl groups and R$^{a3}$ is an adamantyl group such as a 1-(1-adamantyl)-1-alkylalkoxycarbonyl group are preferable.

MONOMER (a1) is preferably an acrylate monomer having an acid-labile group in its side chain or a methacryalte monomer having an acid-labile group in its side chain. In this specification, "(meth)acrylate monomer" means a monomer having a structure represented by CH$_2$=CH—CO— or CH$_2$=C(CH$_3$)—CO—, and "acrylate monomer" means a monomer having a structure represented by CH$_2$=CH—CO—, and "methacrylate monomer" means a monomer having a structure represented by CH$_2$=C(CH$_3$)—CO—.

Preferable examples of MONOMER (a1) include (meth)acrylate monomers having C5-C20 saturated cyclic hydrocarbon group. As (meth)acrylate monomers having C5-C20 saturated cyclic hydrocarbon group, preferred are monomers represented by the formulae (a1-1) and (a1-2)

(a1-1)

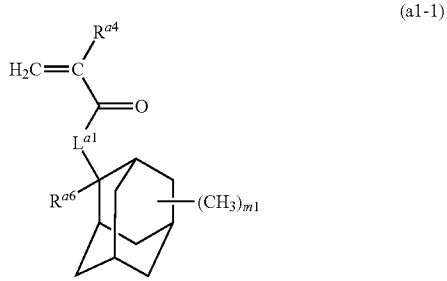

(a1-2)

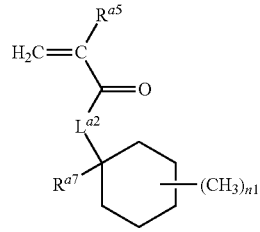

wherein R$^{a4}$ and R$^{a5}$ dependently represent a hydrogen atom or a methyl group, R$^{a6}$ and R$^{a7}$ independently represents a C1-C8 aliphatic hydrocarbon group or a C3-C10 saturated cyclic hydrocarbon group, L$^{a1}$ and L$^{a2}$ independently represents *—O— or *—O—(CH$_2$)$_{k1}$—CO—O— in which * represents a binding position to —CO—, and k1 represents an integer of 1 to 7, m1 represents an integer of 0 to 14 and n1 represents an integer of 0 to 10.

The aliphatic hydrocarbon group preferably has 1 to 6 carbon atoms, and the saturated cyclic hydrocarbon group preferably has 3 to 8 carbon atoms and more preferably 3 to 6 carbon atoms.

Examples of the aliphatic hydrocarbon group include a C1-C8 alkyl group such as a methyl group, an ethyl group, a propyl group, an isopropyl group, a butyl group, a tert-butyl group, a 2,2-dimethylethyl group, a 1-methylpropyl group, a 2,2-dimethylpropyl group, a 1-ethylpropyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the saturated cyclic hydrocarbon group include a cyclohexyl group, a methylcyclohexyl group, a dimethylcyclohexyl group, a cycloheptyl group, a methylcycloheptyl group, a norbornyl group and a methylnorbornyl group.

L$^{a1}$ is preferably *—O— or *—O—(CH$_2$)$_{f1}$—CO—O— in which * represents a binding position to —CO—, and f1 represents an integer of 1 to 4, and is more preferably *—O— or *—O—CH$_2$—CO—O—, and is especially preferably *—O—. L$^{a2}$ is preferably *—O— or *—O—(CH$_2$)$_{f1}$—CO—O— in which * represents a binding position to —CO—, and f1 is the same as defined above, and is more preferably *—O— or *—O—CH$_2$—CO—O—, and is especially preferably *—O—.

In the formula (a1-1), m1 is preferably an integer of 0 to 3, and is more preferably 0 or 1. In the formula (a1-2), n1 is preferably an integer of 0 to 3, and is more preferably 0 or 1.

Examples of the monomer represented by the formula (a1-1) include the followings.

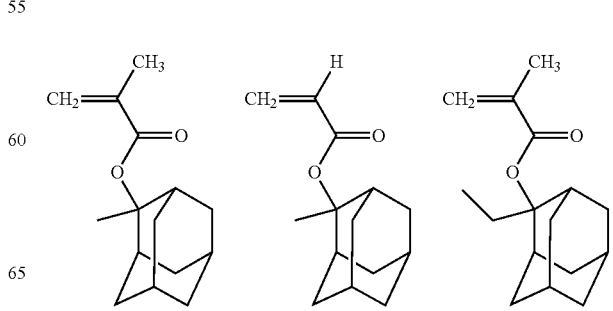

-continued
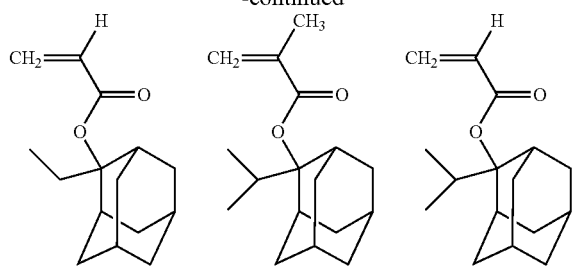
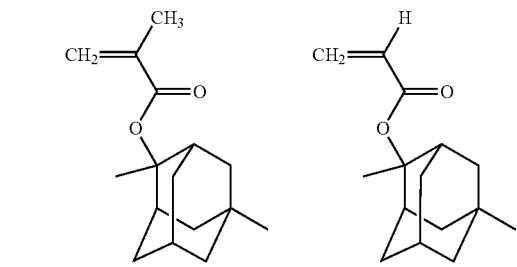
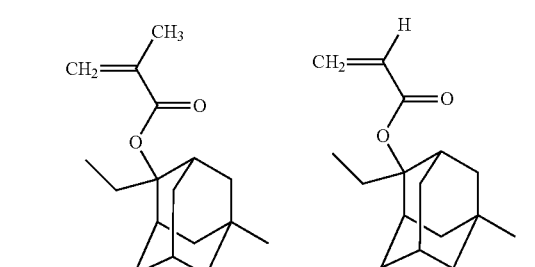
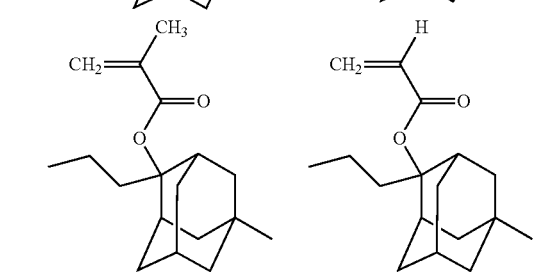
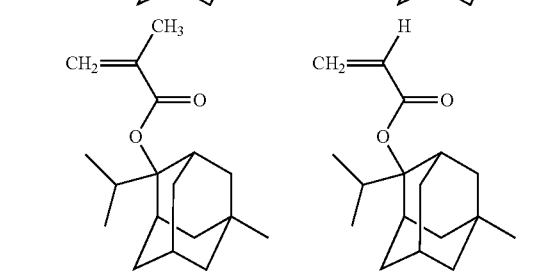
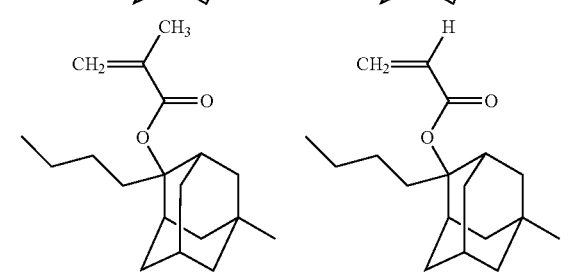
-continued
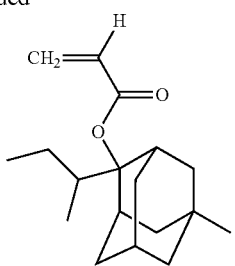
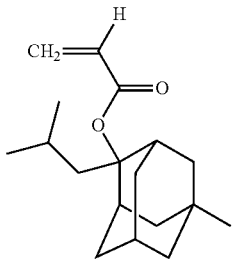
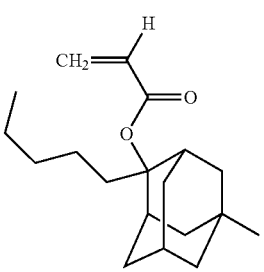
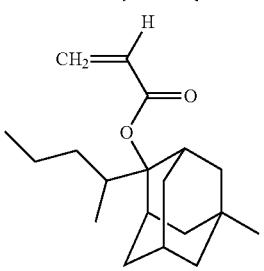
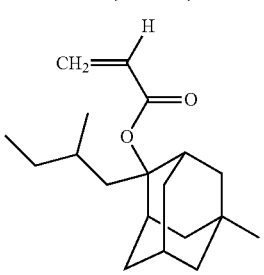
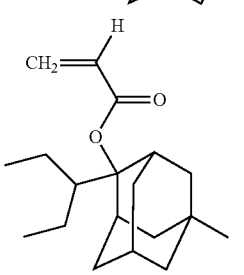

-continued
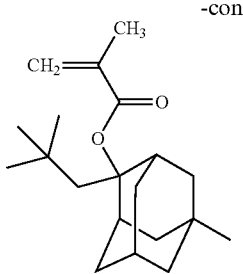 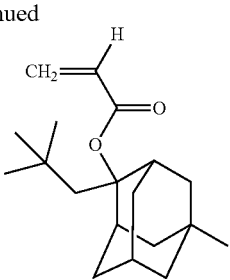 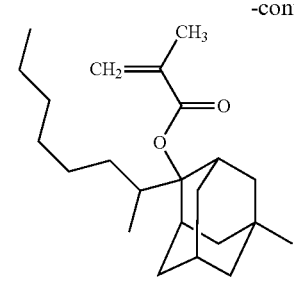 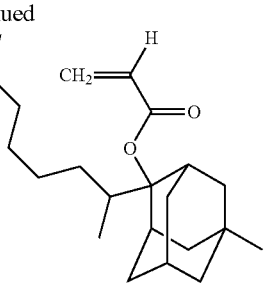
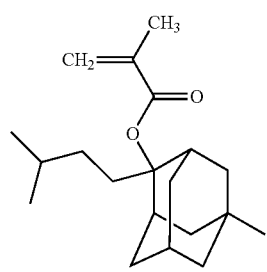 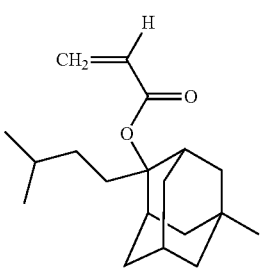 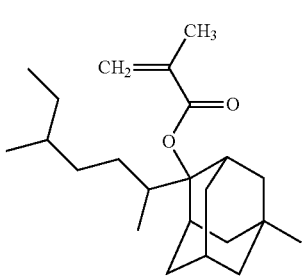
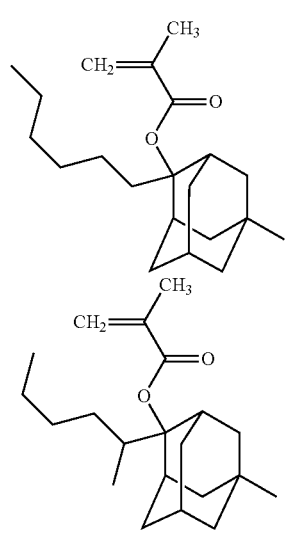 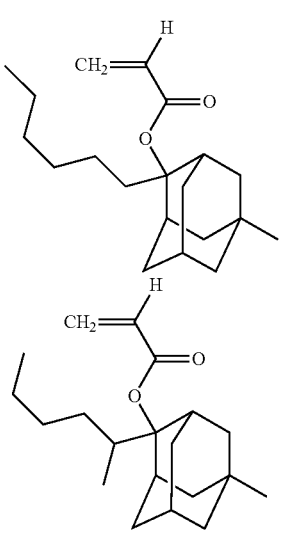 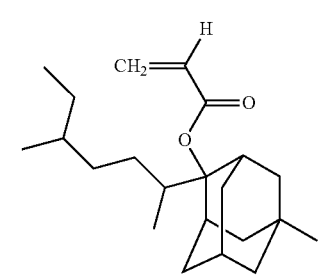
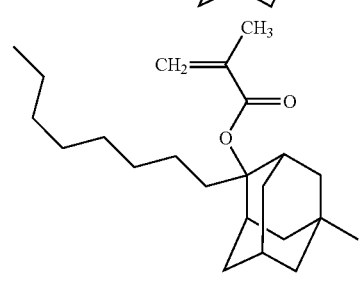
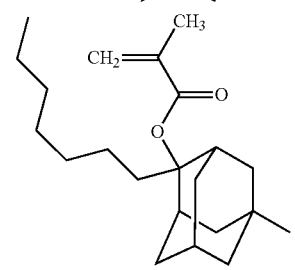 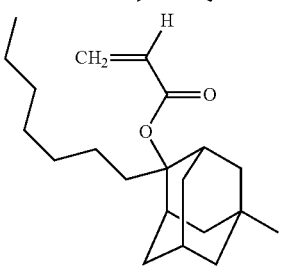 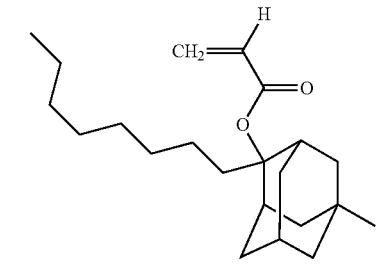
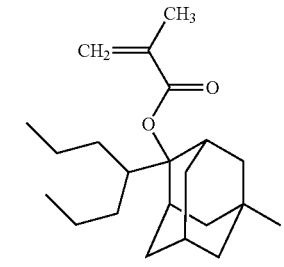 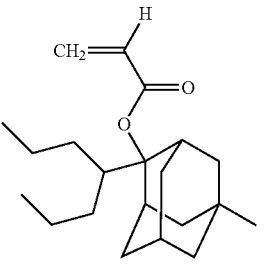 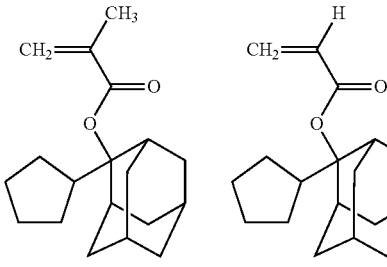

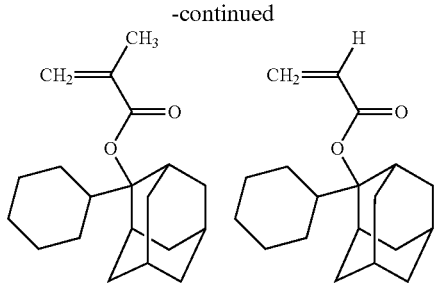
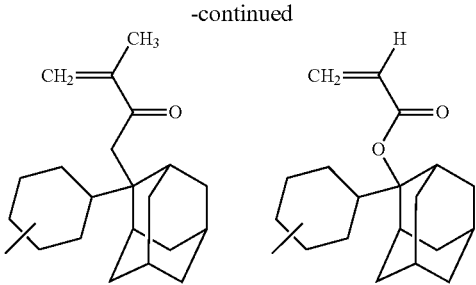

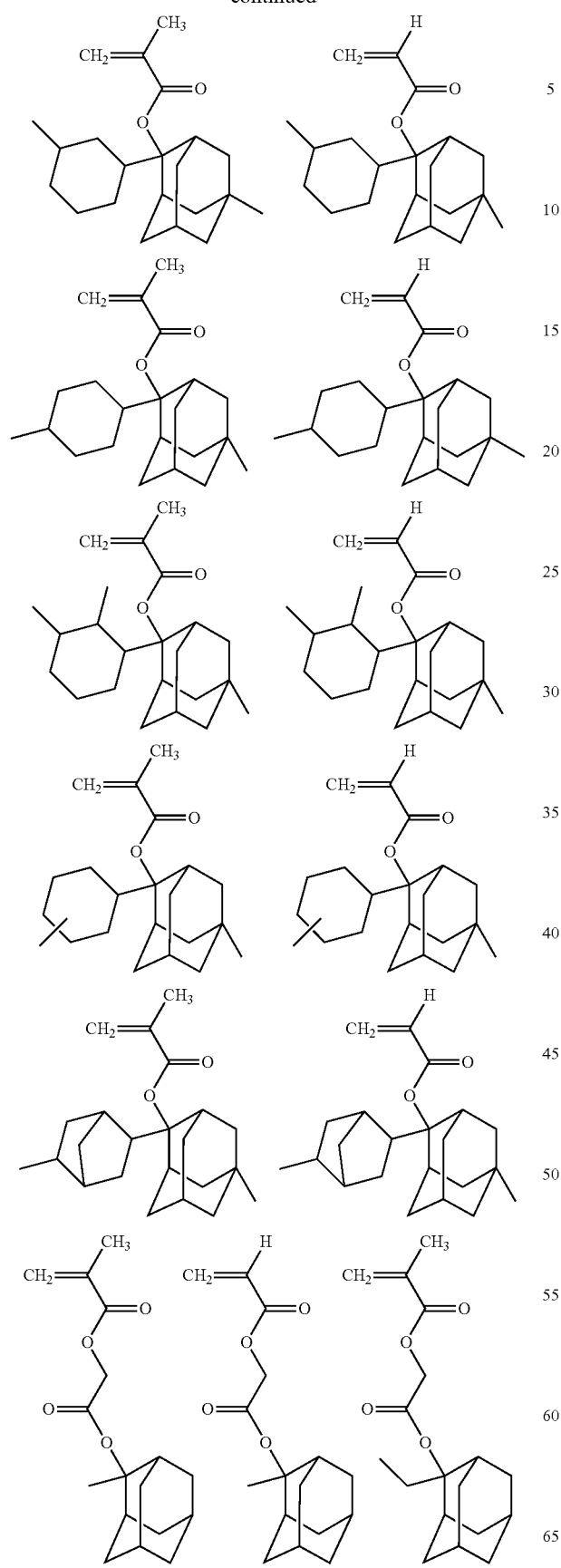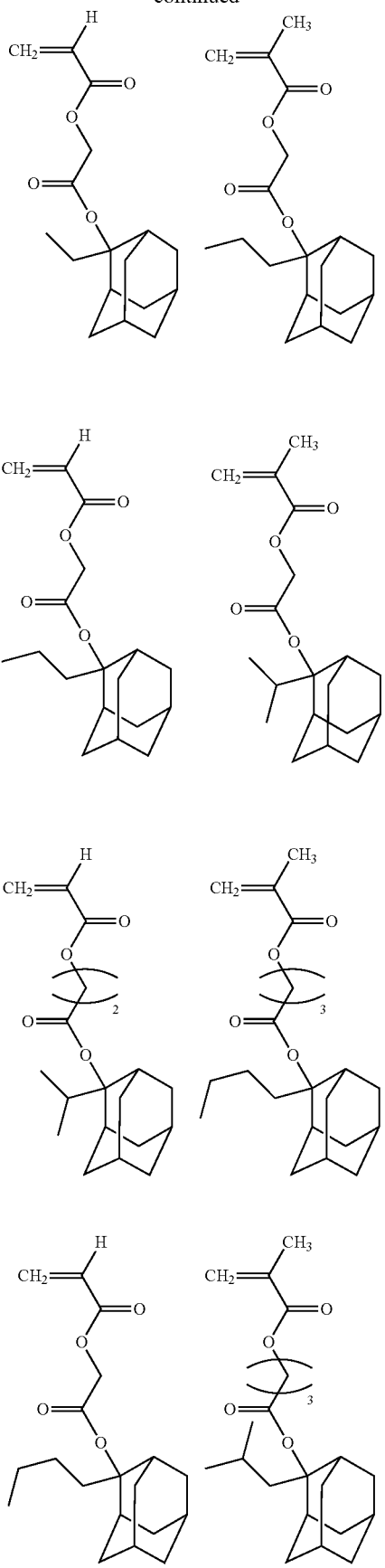

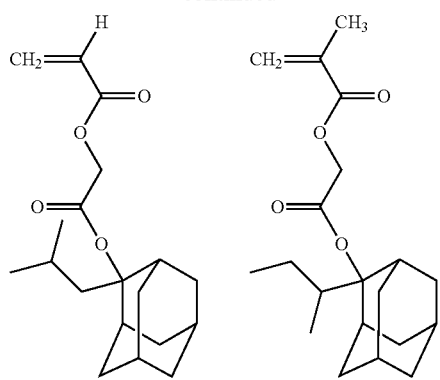
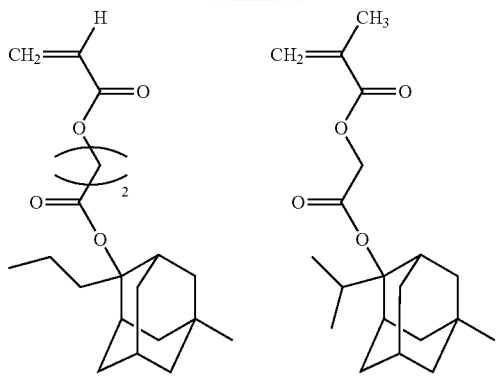
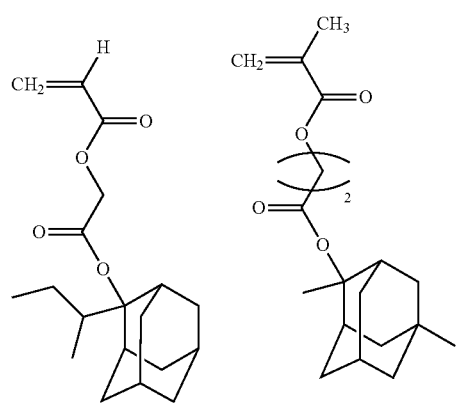
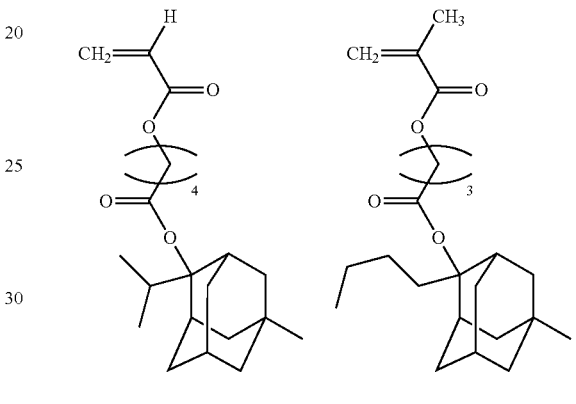
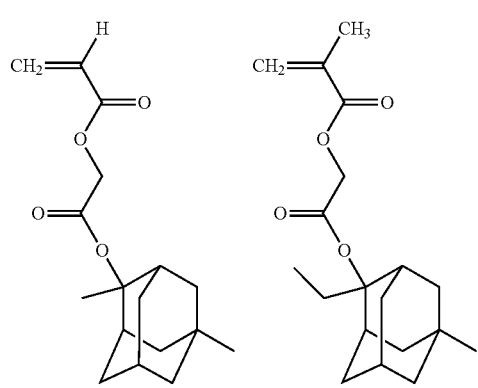
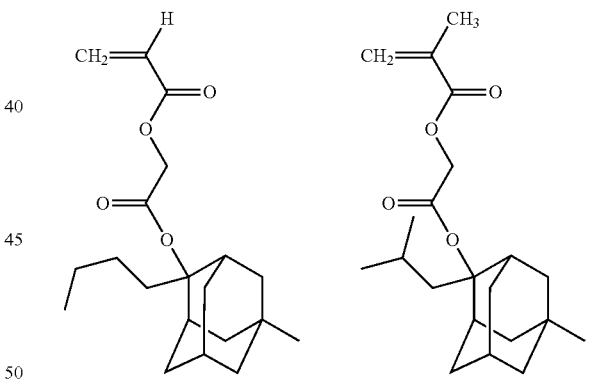
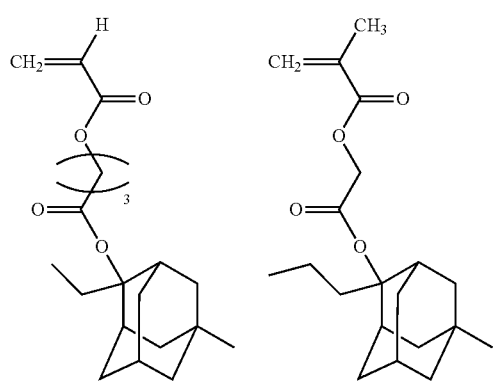
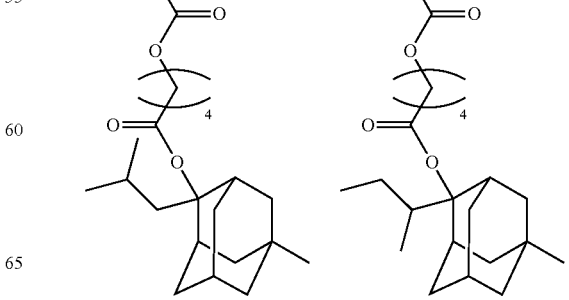

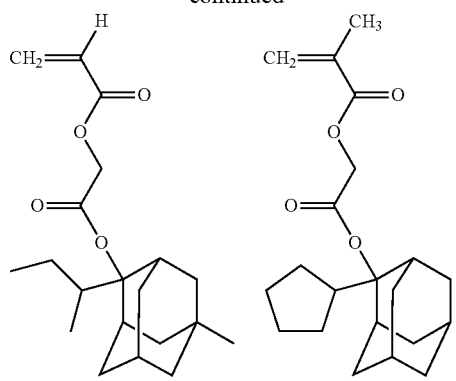
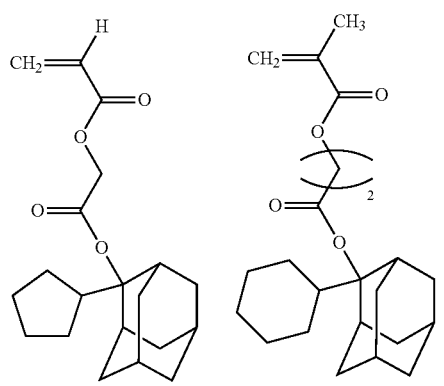
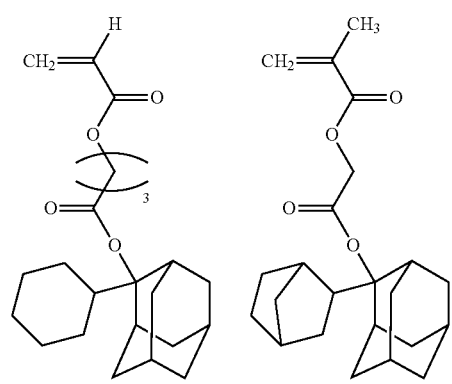
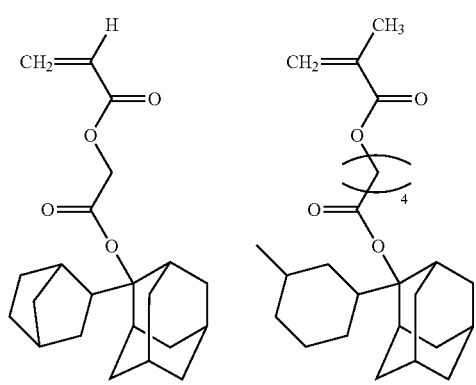
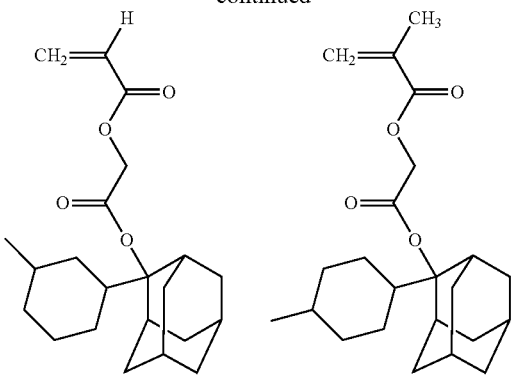
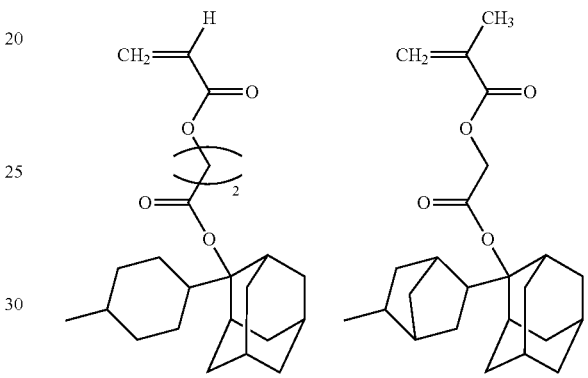
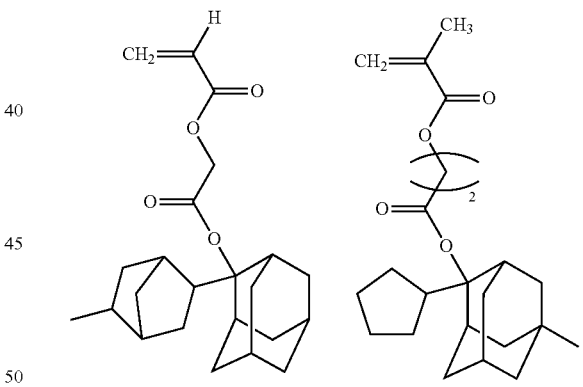
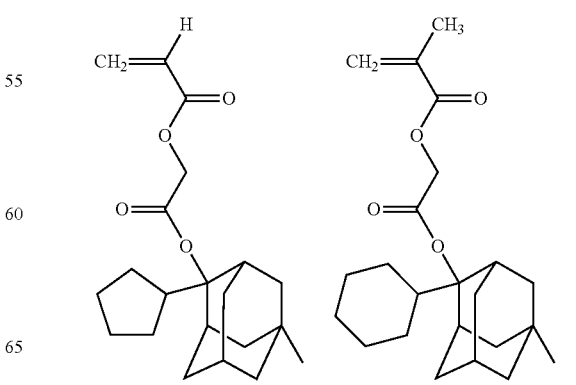

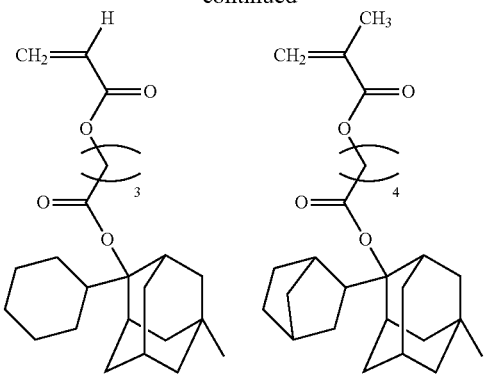
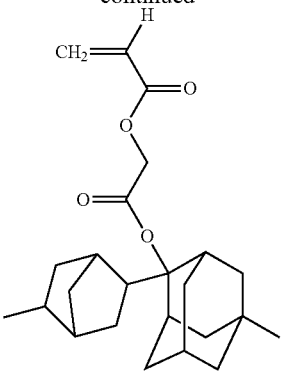

Among them, preferred are 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate and 2-isopropyl-2-adamantyl methacrylate, and more preferred are 2-methyl-2-adamantyl methacrylate, 2-ethyl-2-adamantyl methacrylate, and 2-isopropyl-2-adamantyl methacrylate.

Examples of the monomer represented by the formula (a1-2) include the followings.

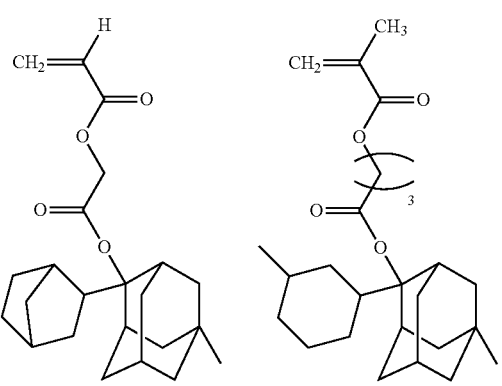

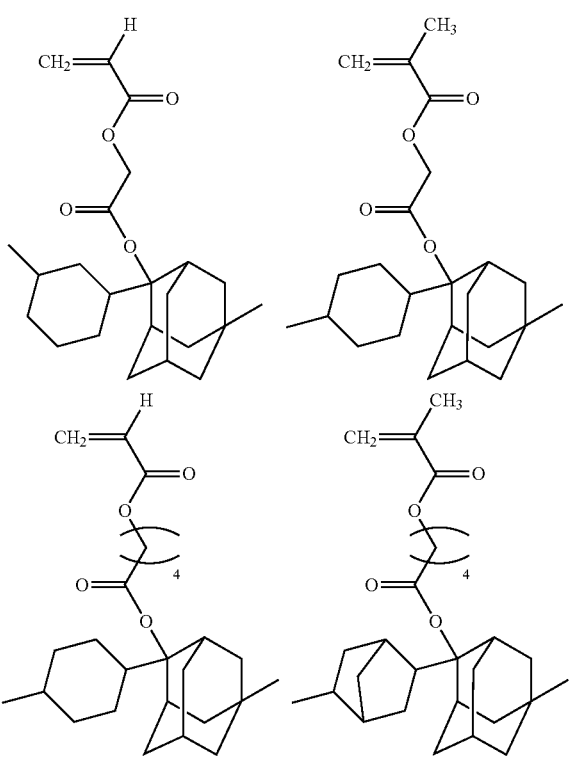

Among them, preferred are 1-ethyl-1-cyclohexyl acrylate and 1-ethyl-1-cyclohexyl methacrylate, and more preferred is 1-ethyl-1-cyclohexyl methacrylate.

The content of the structural unit derived from MONOMER (a1) in POLYMER (I) is usually 10 to 95% by mole, preferably 15 to 90% by mole and more preferably 20 to 85% by mole based on 100% by mole of all the structural units of POLYMER (I).

Other examples of MONOMER (a1) include a monomer represented by the formula (a1-3):

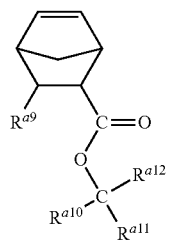

(a1-3)

wherein $R^{a9}$ represents a hydrogen atom, a C1-C3 aliphatic hydrocarbon group which can have one or more substituents, a carboxyl group, a cyano group or a —COOR$^{a13}$ group in which $R^{a13}$ represents a C1-C8 aliphatic hydrocarbon group or a C3-C8 saturated cyclic hydrocarbon group, and the C1-C8 aliphatic hydrocarbon group and the C3-C8 saturated cyclic hydrocarbon group can have one or more hydroxyl groups, and one or more —CH$_2$— in the C1-C8 aliphatic hydrocarbon group and the C3-C8 saturated cyclic hydrocarbon group can be replaced by —O— or —CO—, $R^{a10}$, $R^{a11}$ and $R^{a12}$ independently represent a C1-C12 aliphatic hydrocarbon group or a C3-C12 saturated cyclic hydrocarbon group, or $R^{a10}$ and $R^{a11}$ are bonded each other to form a ring together with the carbon atom to which $R^{a10}$ and $R^{a11}$ are bonded, and the C1-C12 aliphatic hydrocarbon group and the C3-C12 saturated cyclic hydrocarbon group can have one or more hydroxyl groups, and one or more —CH$_2$— in the C1-C12 aliphatic hydrocarbon group and the C3-C12 saturated cyclic hydrocarbon group can be replaced by —O— or —CO—.

Examples of the substituent include a hydroxyl group. Examples of the C1-C3 aliphatic hydrocarbon group which can have one or more substituents include a methyl group, an ethyl group, a propyl group, a hydroxymethyl group and a 2-hydroxyethyl group. Examples of $R^{a13}$ include a methyl group, an ethyl group, a propyl group, a 2-oxo-oxolan-3-yl group and a 2-oxo-oxolan-4-yl group. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group, and examples of the ring formed by bonding $R^{a10}$ and $R^{a11}$ each other together with the carbon atom to which $R^{a10}$ and $R^{a11}$ are bonded include a cyclohexane ring and an adamantane ring.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxycyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When POLYMER (I) contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of POLYMER (I).

Other examples of MONOMER (a1) include a monomer represented by the formula (a1-4)

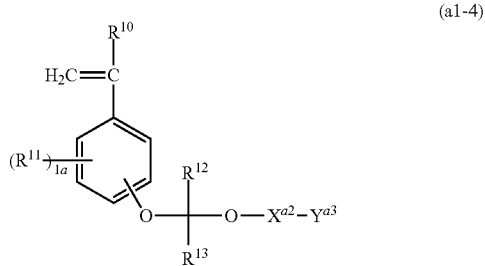

(a1-4)

wherein $R^{10}$ represents a hydrogen atom, a halogen atom, a C1-C6 alkyl group or a C1-C6 halogenated alkyl group, $R^{11}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, 1a represents an integer of 0 to 4, $R^{12}$ and $R^{13}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N(R$^c$)— wherein R$^c$ represents a hydrogen atom or a C1-C6 alkyl group, and $Y^{a3}$ represents a C1-C12 aliphatic hydrocarbon group, a C3-C18 saturated cyclic hydrocarbon group or a C6-C18 aromatic hydrocarbon group, and the C1-C12 aliphatic hydrocarbon group, the C2-C18 saturated cyclic hydrocarbon group and the C6-C18 aromatic hydrocarbon group can have one or more substituents.

Examples of the halogen atom include a fluorine atom.

Examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the C1-C12 hydrocarbon group include a C1-C12 aliphatic hydrocarbon group such as a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group, and a C3-C12 saturated cyclic hydrocarbon group such as a cyclohexyl group, an adamantyl group, a 2-alkyl-2-adamantyl group, a 1-(1-adamantyl)-1-alkyl group and an isobornyl group.

Examples of the C1-C17 divalent saturated hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,1'-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the C1-C12 aliphatic hydrocarbon group include a methyl group, an ethyl group, a propyl group, an isopropyl group, a butyl group, an isobutyl group, a sec-butyl group, a tert-butyl group, a pentyl group, a hexyl group, a heptyl group, an octyl group, a 2-ethylhexyl group, a nonyl group, a decyl group, an undecyl group and a dodecyl group. Examples of the C3-C18 saturated cyclic hydrocarbon group include a cyclopropyl group, a cyclobutyl group, a cyclopentyl group, a cyclohexyl group, a cycloheptyl group, a cyclooctyl group, a cyclononyl group, a cyclodecyl group, a norbornyl group, a 1-adamantyl group, a 2-adamantyl group, an isobornyl group and the following groups:

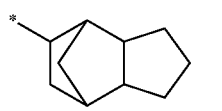 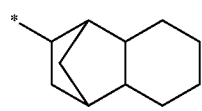

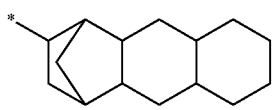 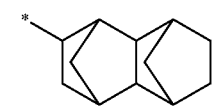

 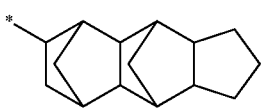

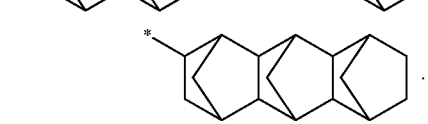

Examples of the C6-C18 aromatic hydrocarbon group include a phenyl group, a naphthyl group, an anthryl group, a p-methylphenyl group, a p-tert-butylphenyl group and a p-adamantylphenyl group.

Examples of the monomer represented by the formula (a1-4) include the followings.

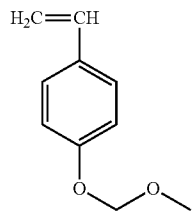 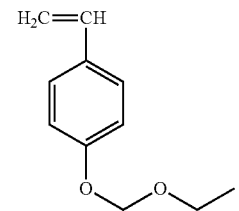

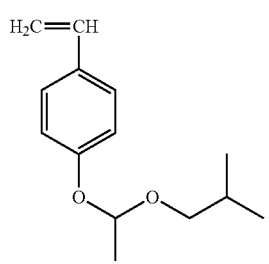 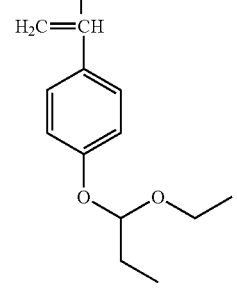

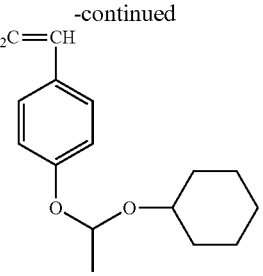

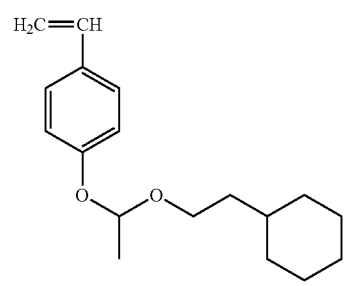

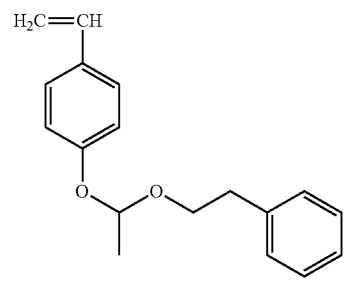

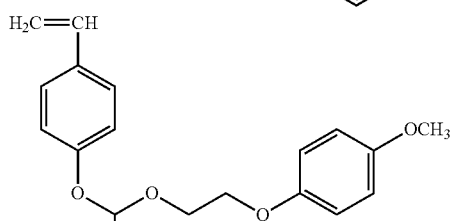

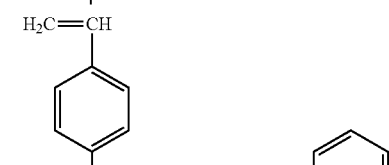

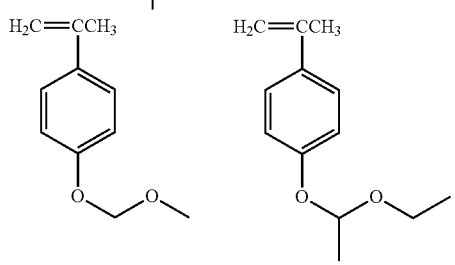

51
-continued
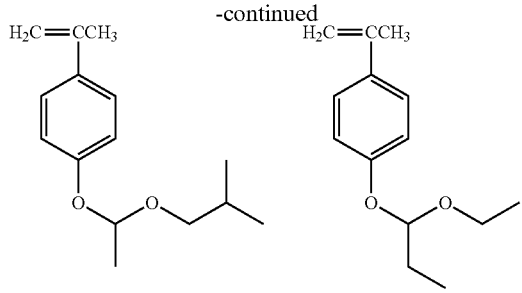
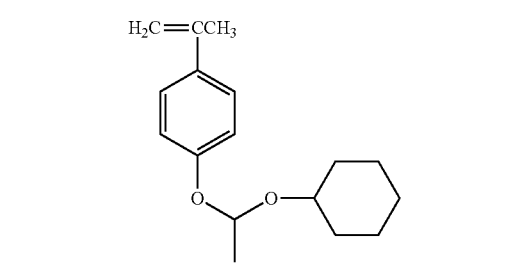
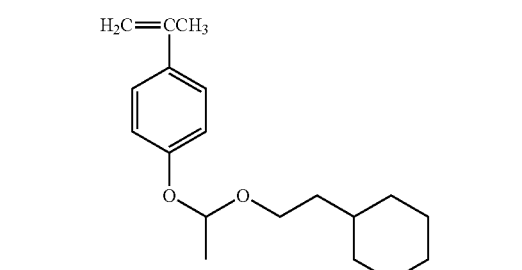
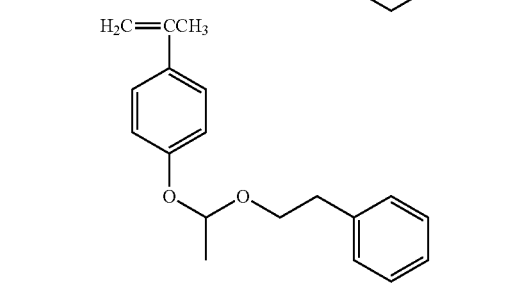
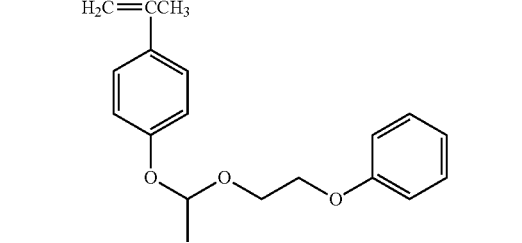
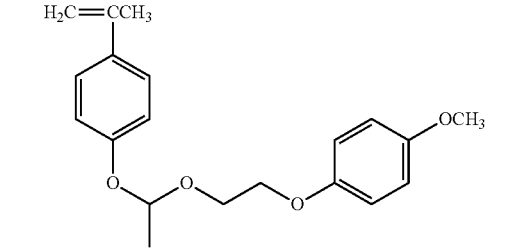
52
-continued
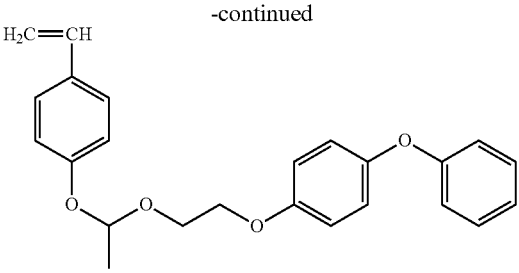
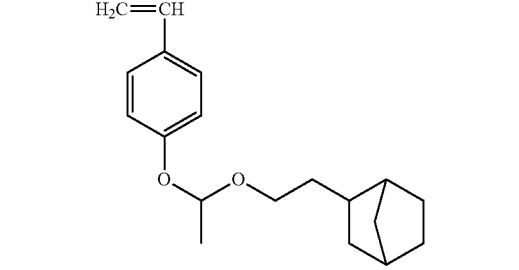
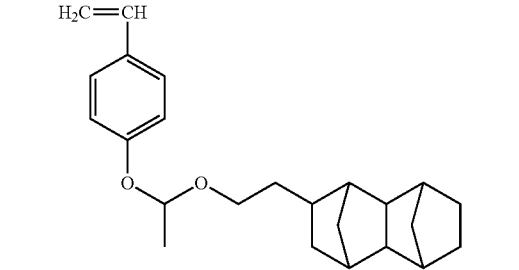
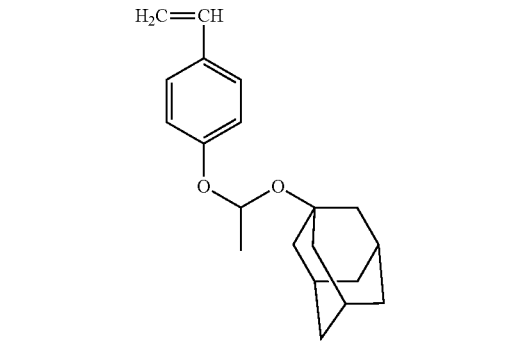
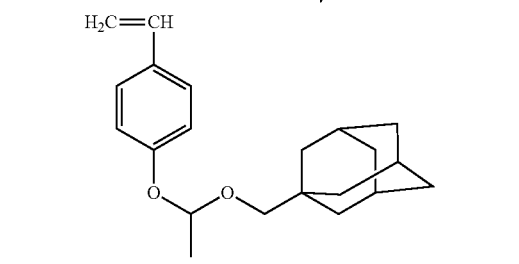
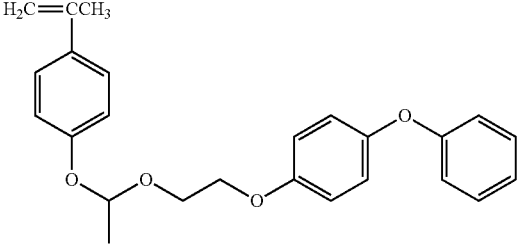

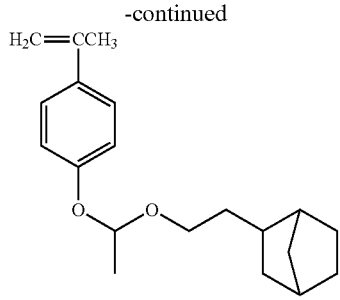
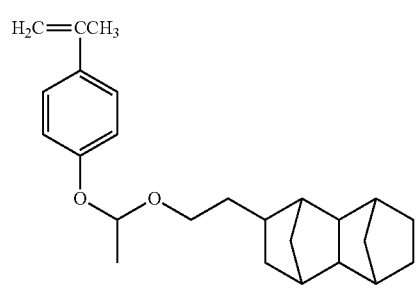
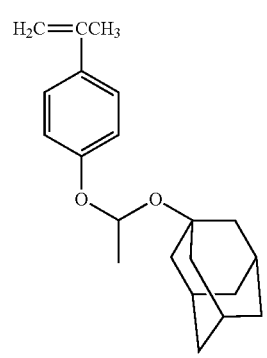
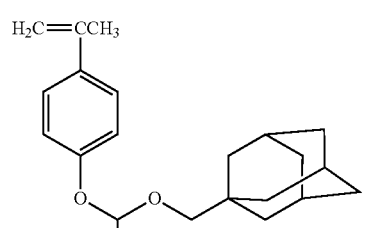
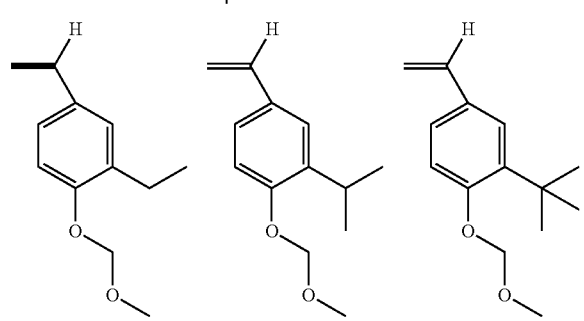
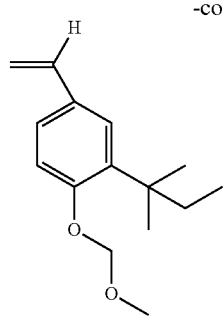
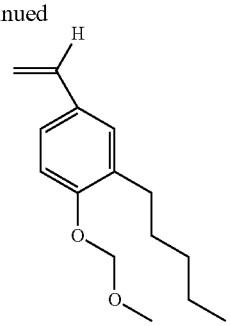
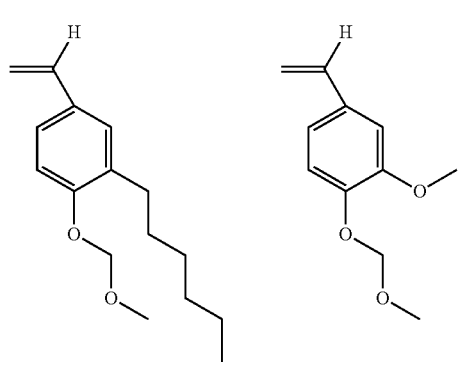
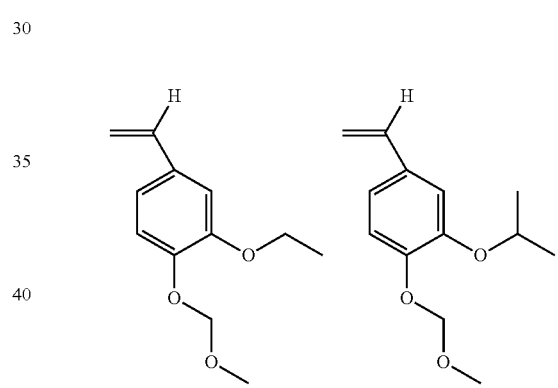
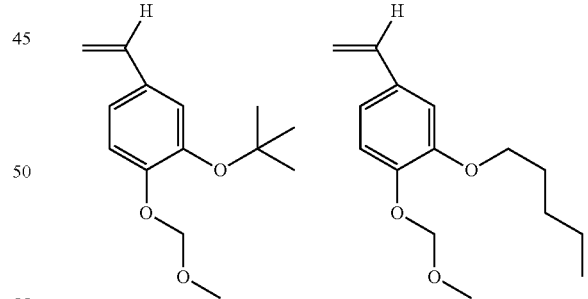
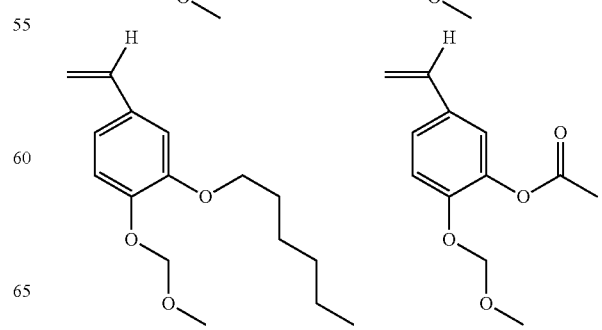

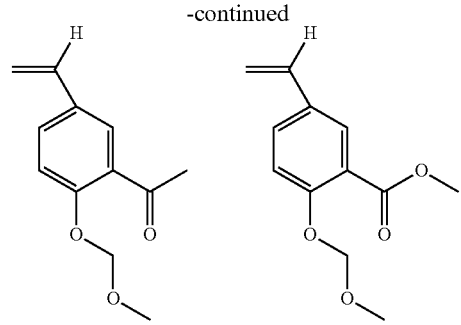
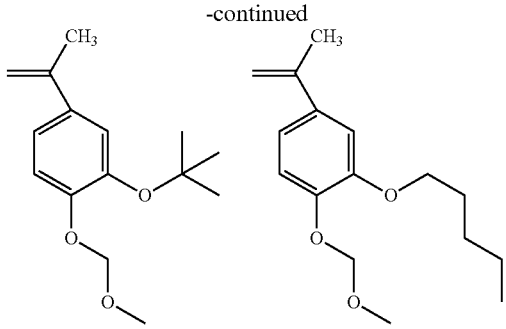
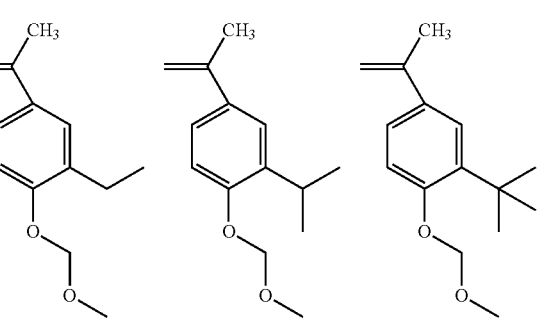
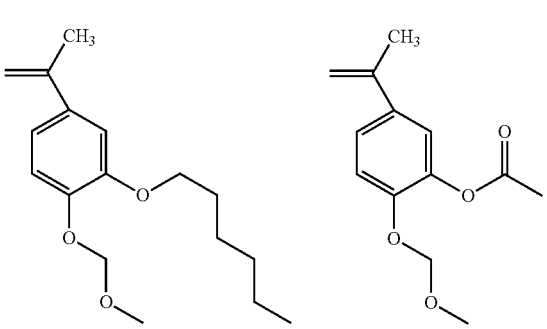
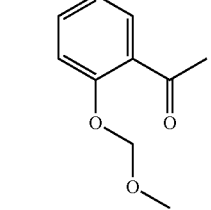
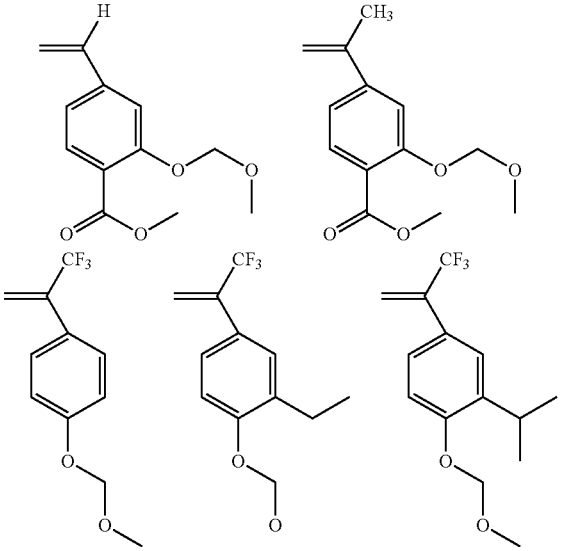

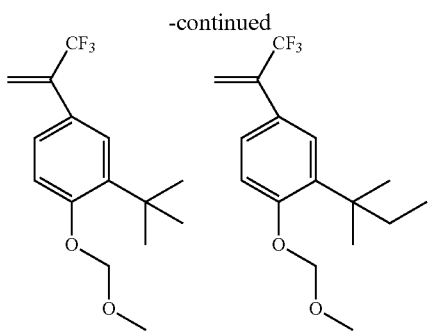

When POLYMER (I) contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of POLYMER (I).

POLYMER (I) preferably contains one or more structural units derived from SALT (I), one or more structural units derived from MONOMER (a1) and one or more structural units derived from a monomer having no acid-labile group POLYMER (I) can have two or more kinds of structural units derived from the monomers having no acid-labile group. When POLYMER (I) contains one or more structural units derived from SALT (I), one or more structural units derived from MONOMER (a1) and one or more structural units derived from a monomer having no acid-labile group, the content of the structural unit derived from SALT (I) is usually 5 to 40% by mole and preferably 10 to 30% by mole based on 10% by mole of the structural units derived from MONOMER (a1), and it is usually 1 to 30% by mole and preferably 3 to 20% by mole based on 100% by mole of all the structural units of POLYMER (I). The content of the structural unit derived from MONOMER (a1) having an adamantyl group, especially the monomer represented by the formula (a1-1) in the structural unit derived from MONOMER (a1), is preferably 15% by mole or more from the viewpoint of dry-etching resistance of the photoresist composition.

Examples of a monomer having no acid-labile group include a monomer having one or more hydroxyl group and no acid-labile group (hereinafter, simply referred to as MONOMER (a2)) and a monomer having a lactone ring and no acid-labile group (hereinafter, simply referred to as MONOMER (a3)). When POLYMER (I) contains the structural unit derived from MONOMER (a2) or MONOMER (a3), a photoresist composition having good resolution and adhesiveness of photoresist to a substrate tends to be obtained.

Examples of MONOMER (a2) include a monomer represented by the formula (a2-0):

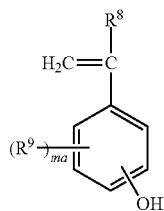

(a2-0)

wherein $R^8$ represents a hydrogen atom, a halogen atom, a C1-C6 alkyl group or a C1-C6 halogenated alkyl group, $R^9$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and a monomer represented by the formula (a2-1):

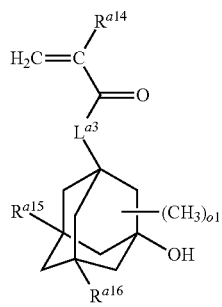

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—(CH$_2$)$_{k2}$—CO—O— in which * represents a binding position to —CO—, and k2 represents an integer of 1 to 7, and of represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tart-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a non-afluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

The resin containing the structural unit derived from the monomer represented by the formula (a2-0) and the structural unit derived from the compound having an acid generator can be produced, for example, by polymerizing the compound having an acid generator and a monomer obtained by protecting a hydroxyl group of the monomer represented by the formula (a2-0) with an acetyl group followed by conducting deacetylation of the obtained polymer with a base.
Examples of the monomer represented by the formula (a2-0) include the followings.
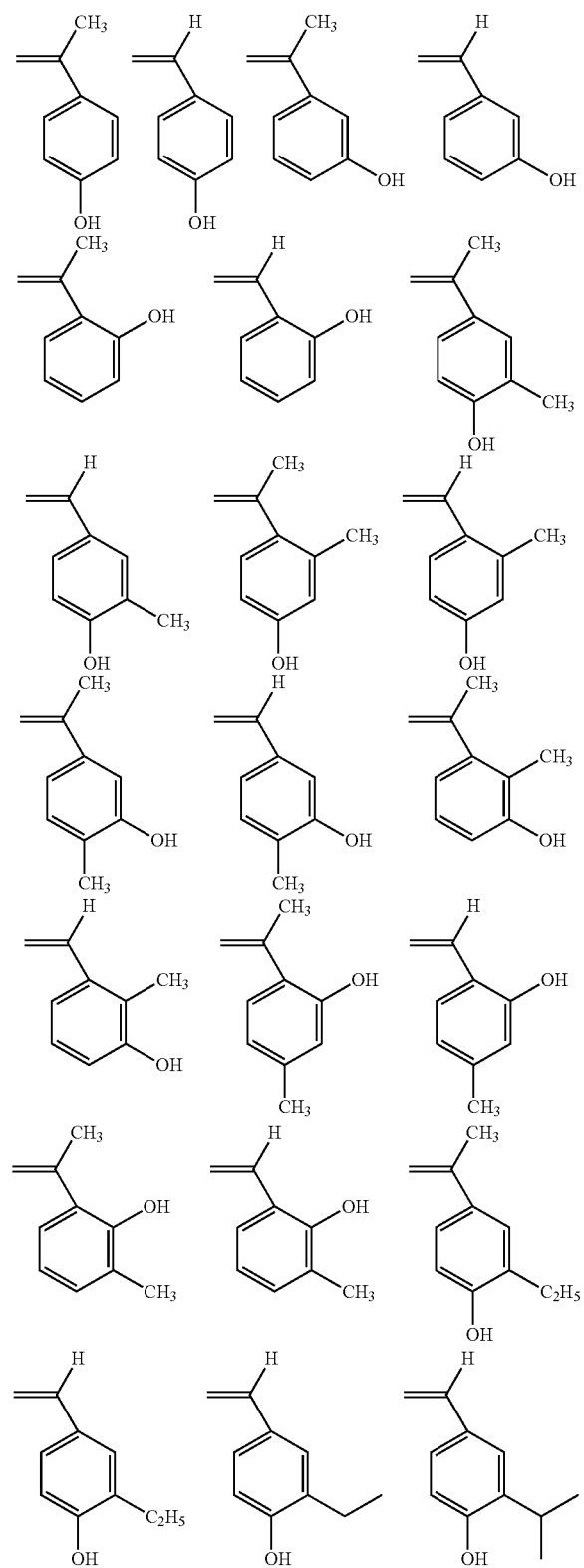
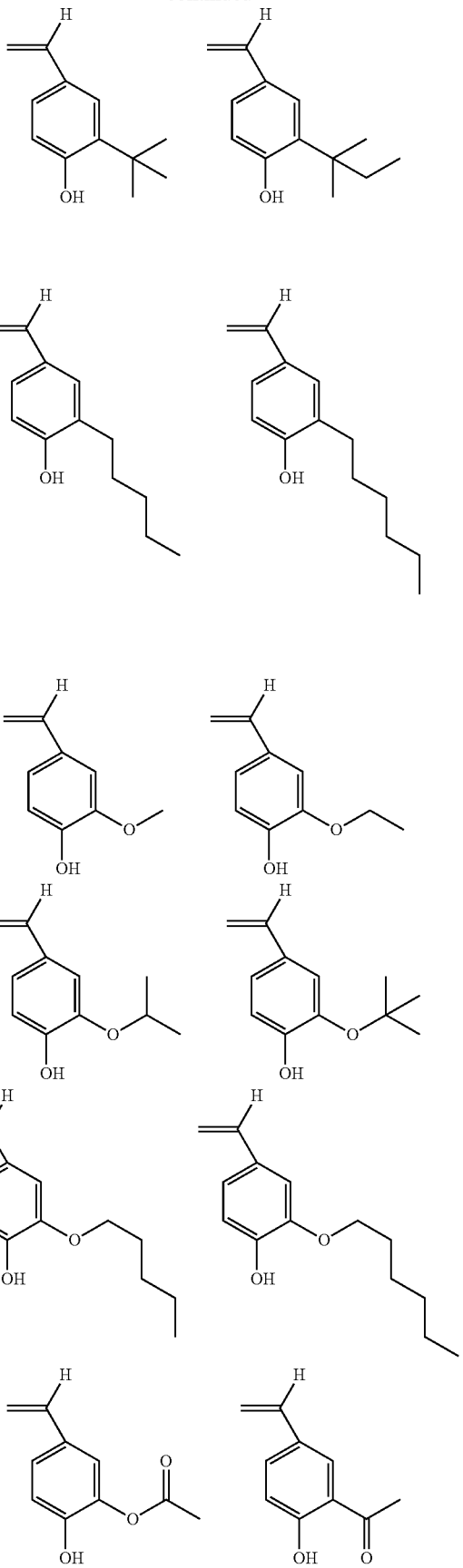

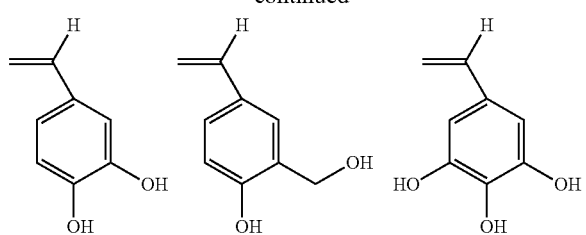

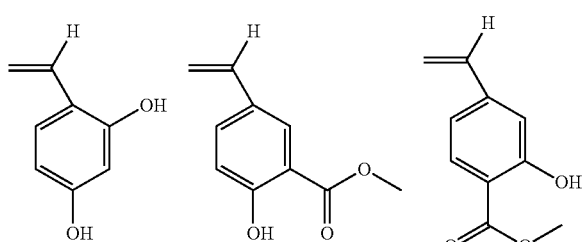

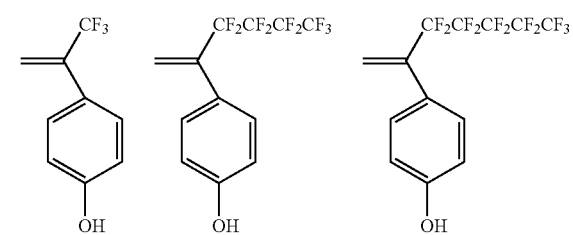

Among them, preferred are 4-hydroxystyrene and 4-hydroxy-α-methylstyrene.

When POLYMER (I) contains the structural unit derived from the monomer represented by the formula (a2-0), the content of the structural unit derived from the monomer represented by the formula (a2-0) is usually 5 to 90% by mole and preferably 10 to 85% by mole and more preferably 15 to 80% by mole based on total molar of all the structural units of POLYMER (I).

In the formula (a2-1) $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO— in which * represents a binding position to —CO—, and f2 represents an integer of 1 to 4, and is more preferably *—O—, and off, is preferably 0, 1, 2 or 3 and is more preferably 0 or 1.

Examples of the monomer represented by the formula (a2-1) include the followings, and 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1- (3,5-dihydroxy-1-adamantyloxycarbonyl) methyl acrylate and 1-(3,5-dihydroxy- 1-adamantyloxycarbonyl)methyl methacrylate are preferable, and 3-hydroxy-1-adamantyl methacrylate and 3,5-dihydroxy-1-adamantyl methacrylate are more preferable.

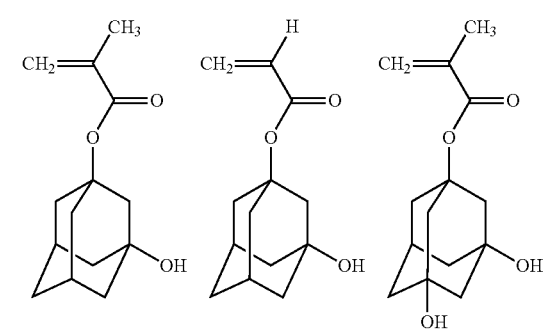

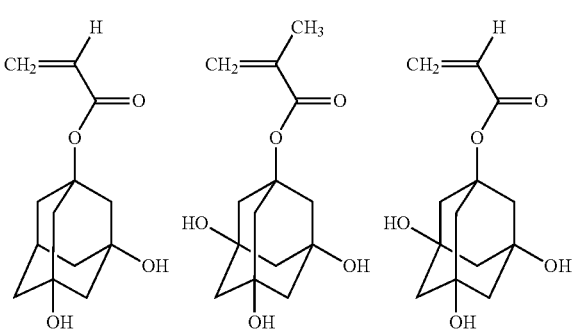

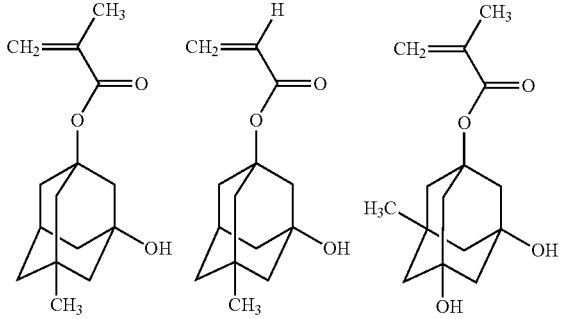

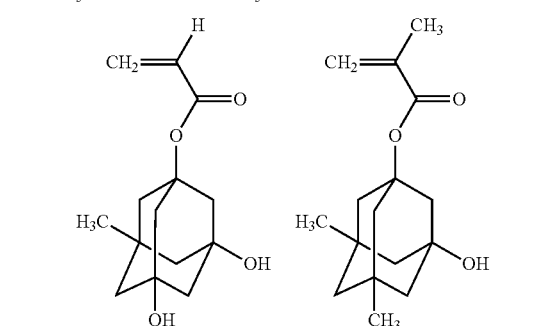

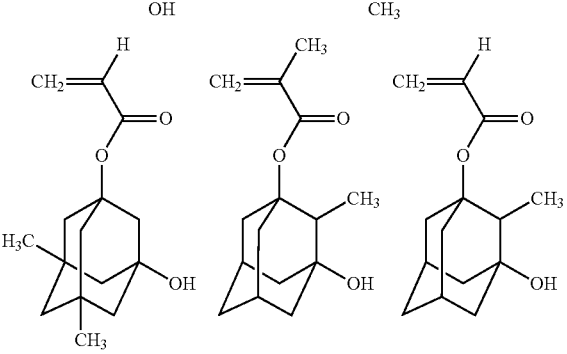

63
-continued
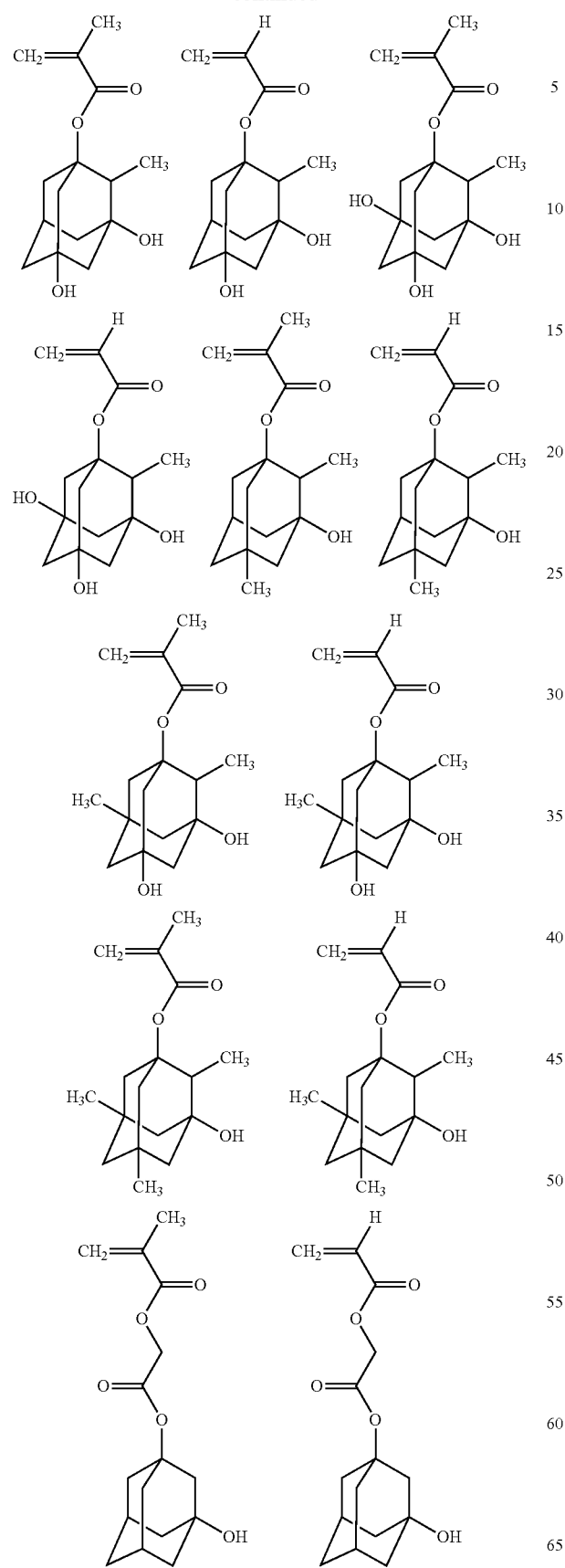
64
-continued
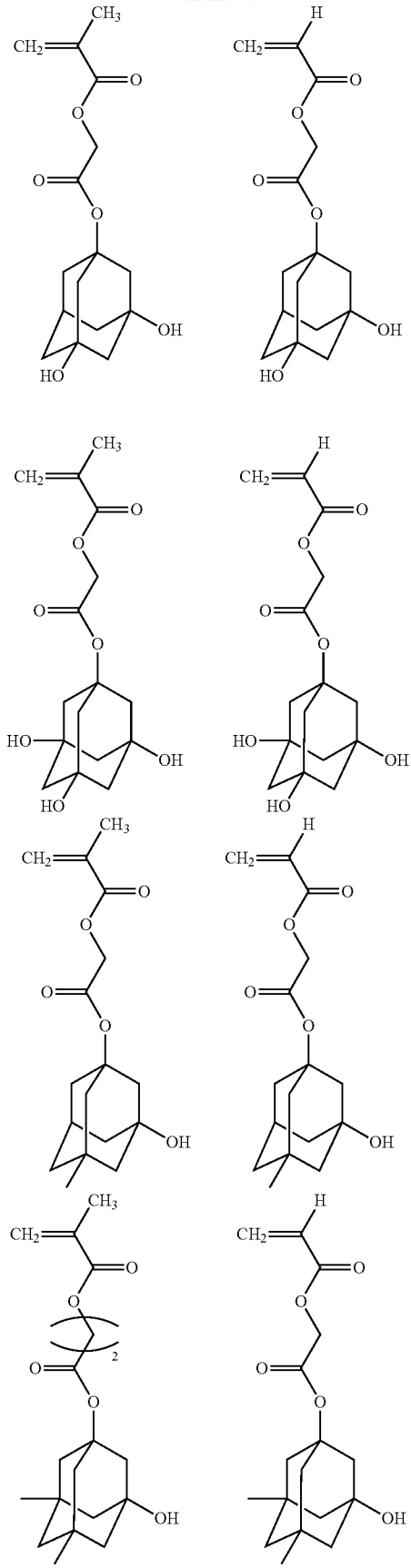

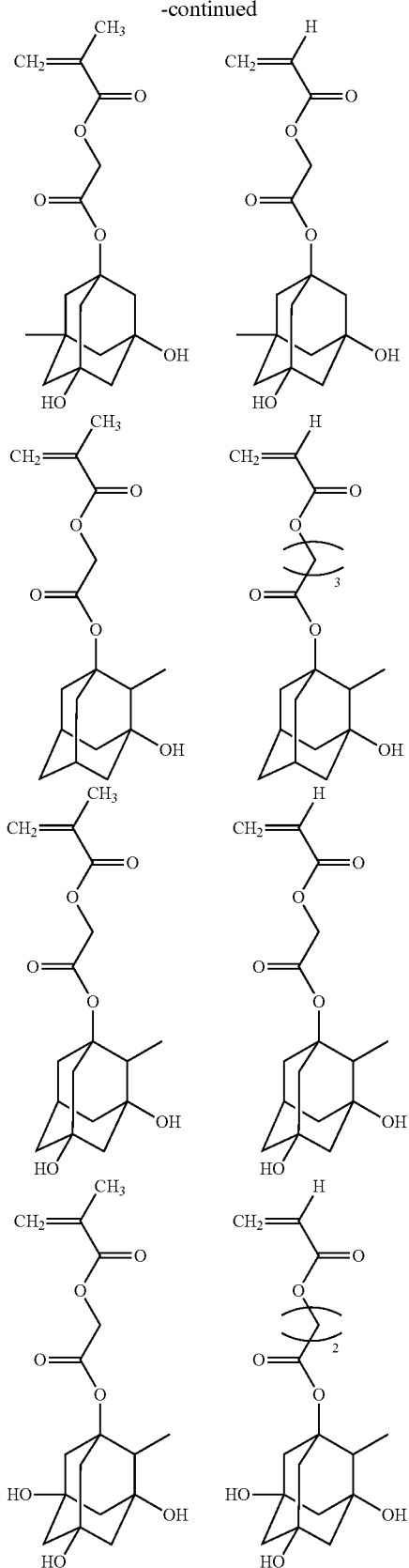

When POLYMER (I) contains the structural unit derived from a monomer represented by the formula (a2-1), the content of the structural unit derived from a monomer represented by the formula (a2-1) is usually 3 to 45% by mole and preferably 5 to 40% by mole and more preferably 5 to 35% by mole based on total molar of all the structural units of POLYMER (I).

Examples of the lactone ring of MONOMER (a3) include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone zing and the other ring.

Preferable examples of MONOMER (a3) include the monomers represented by the formulae (a3-1), (a3-2) and (a3-3):

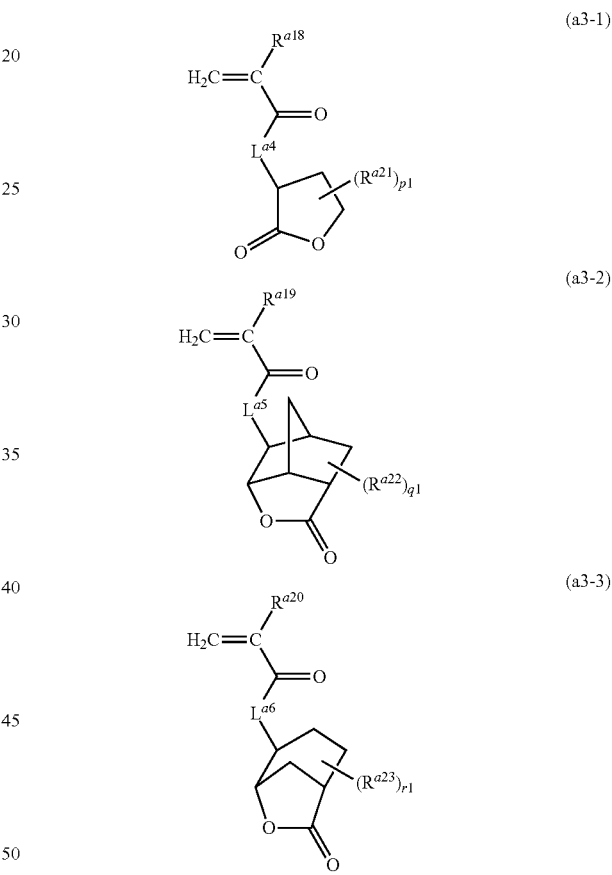

wherein $L_{a4}$, $L^{a5}$ and $L^{a6}$ independently represent *—O— or *—O—$(CH_2)_{k3}$—CO—O— in which * represents a binding position to —CO— and k3 represents an integer of 1 to 7, $R^{a16}$, $R^{a19}$ and $R^{a20}$ independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O—, $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the monomer represented by the formula (a3-1) include the followings.

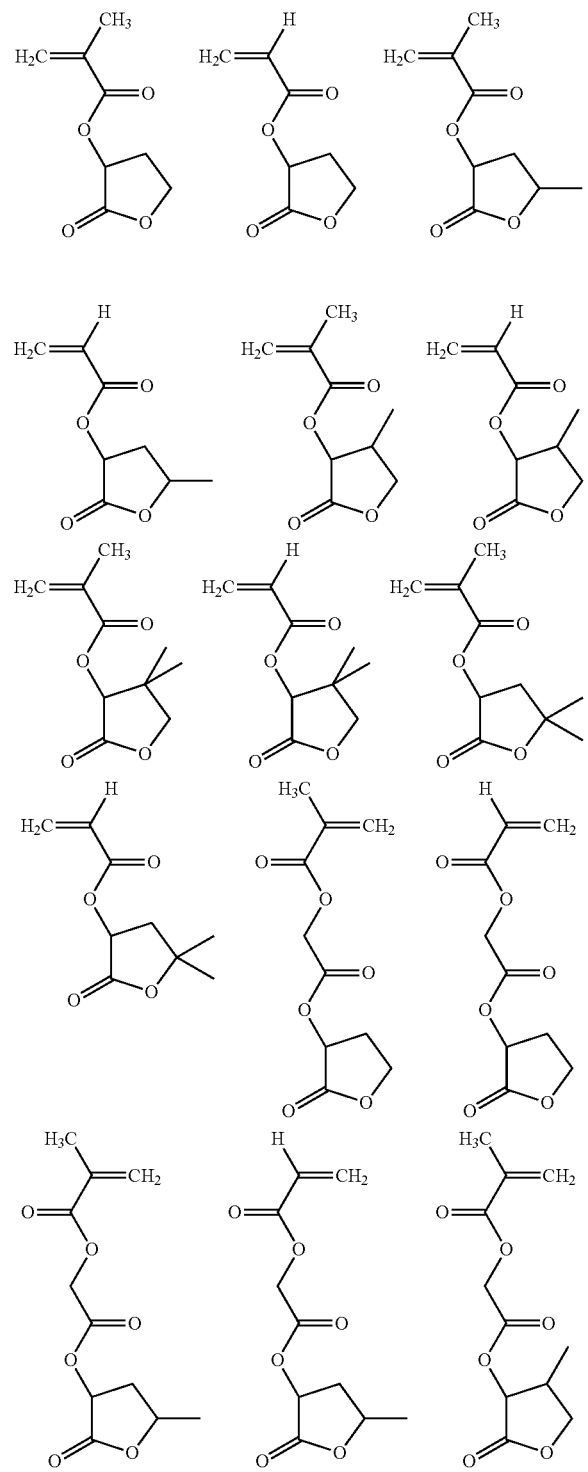

-continued

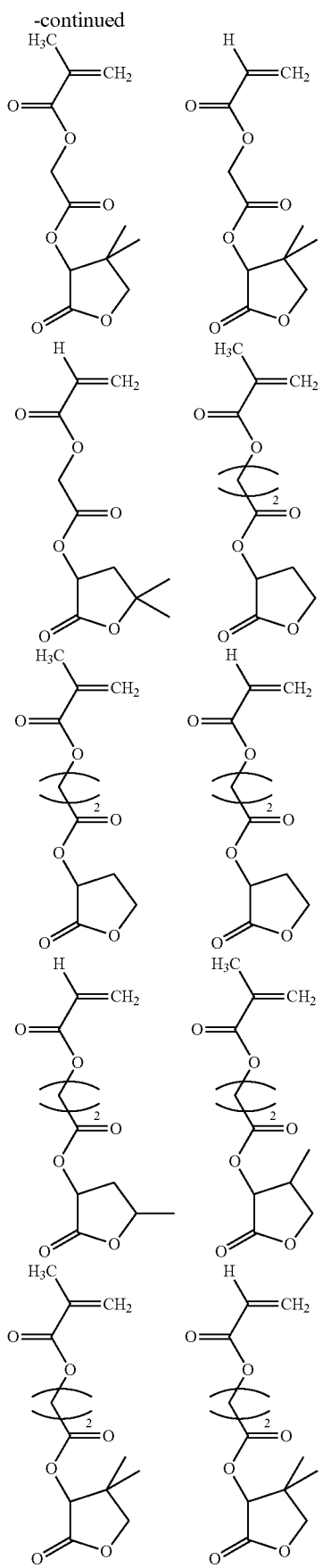

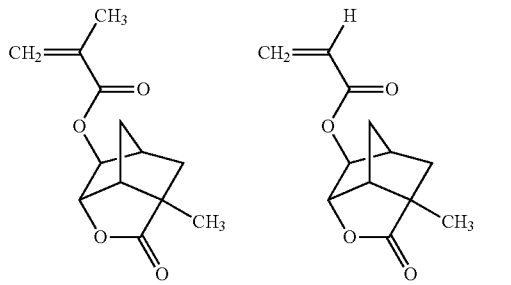
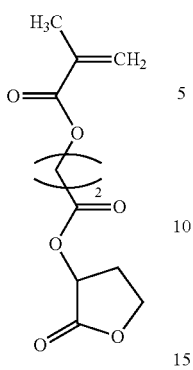
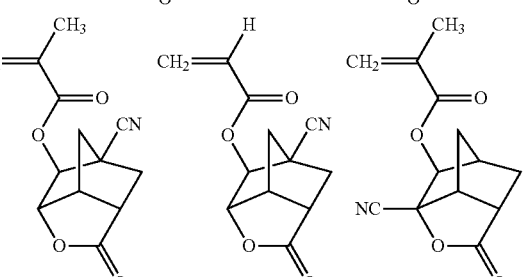
Examples of the monomer represented by the formula (a3-2) include the followings,
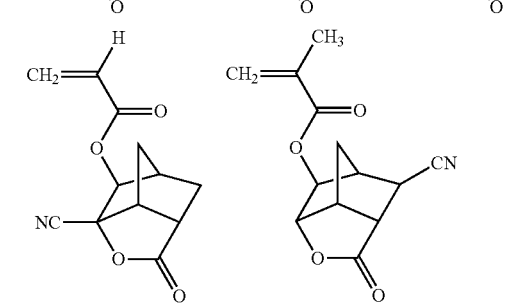
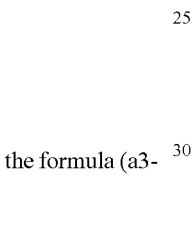
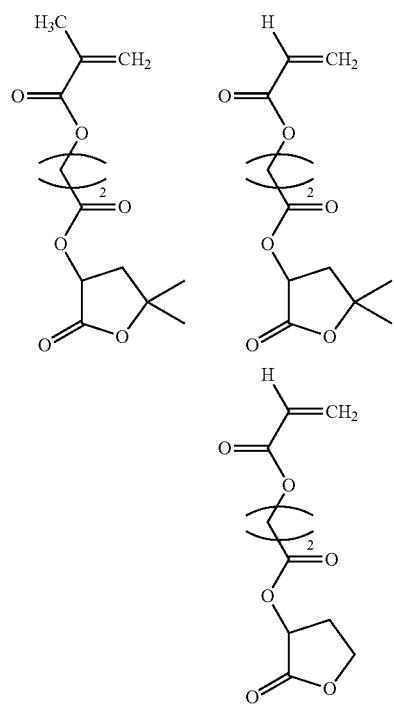
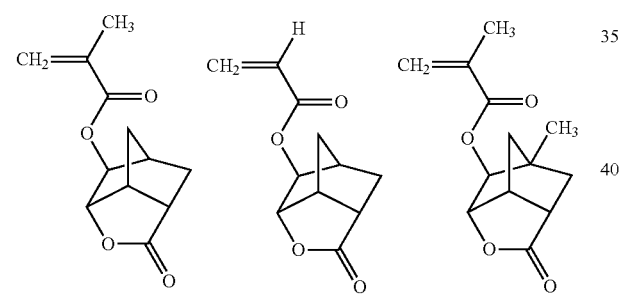
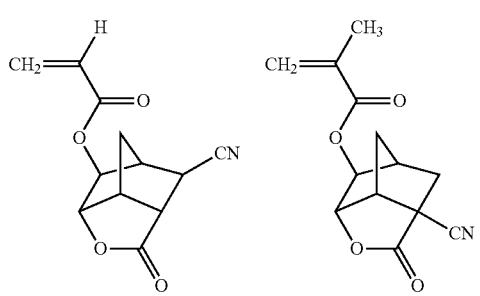
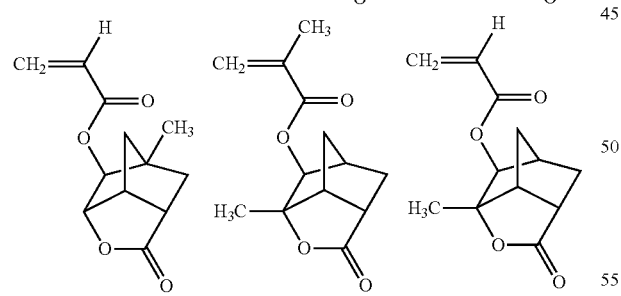
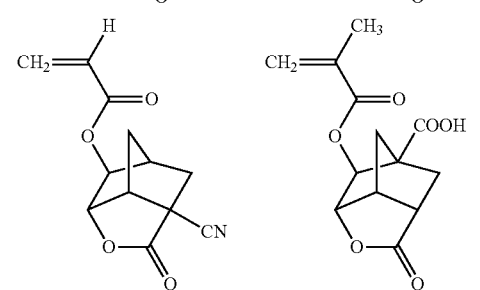
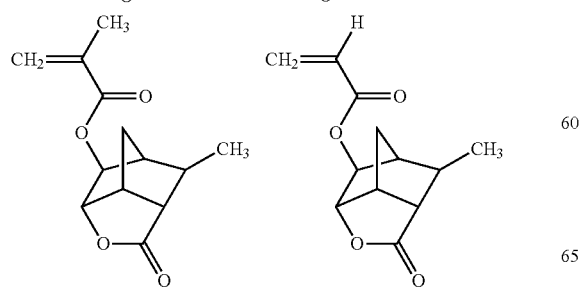
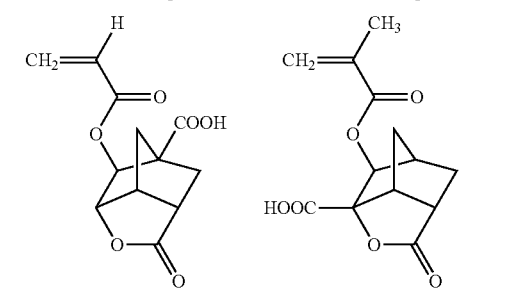

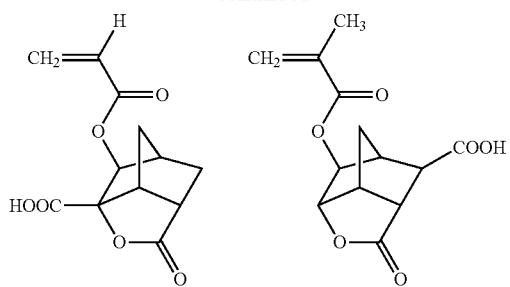
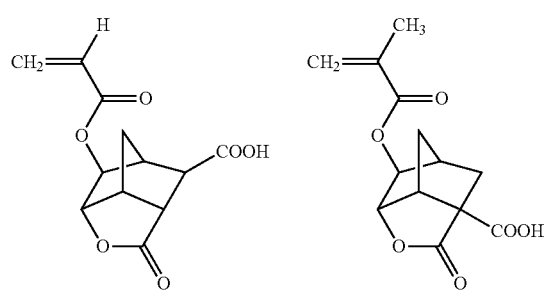
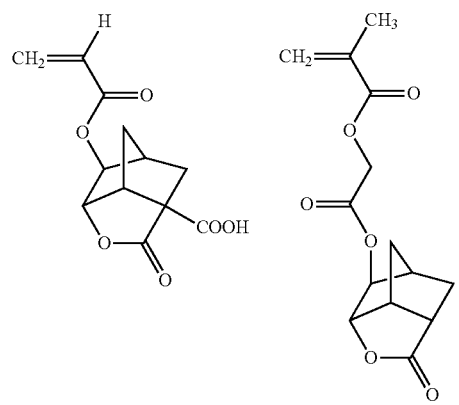
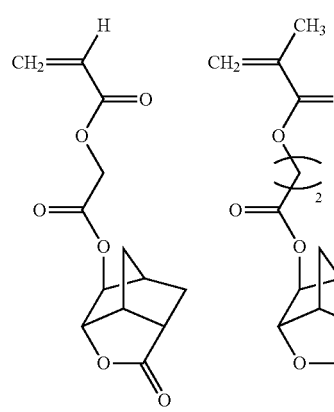
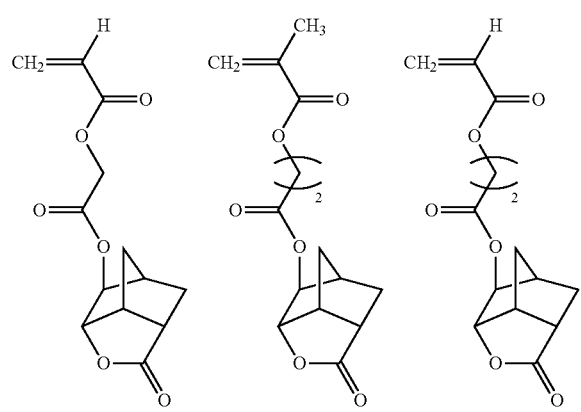
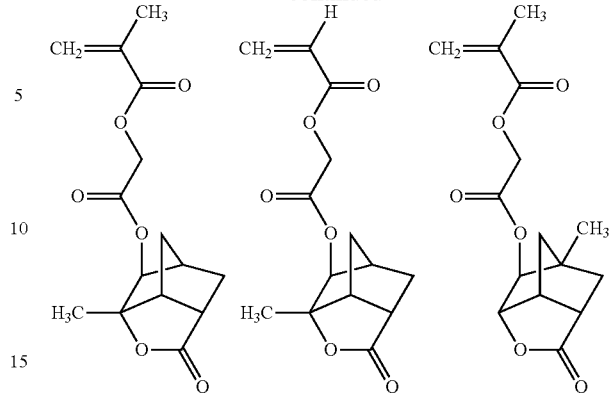
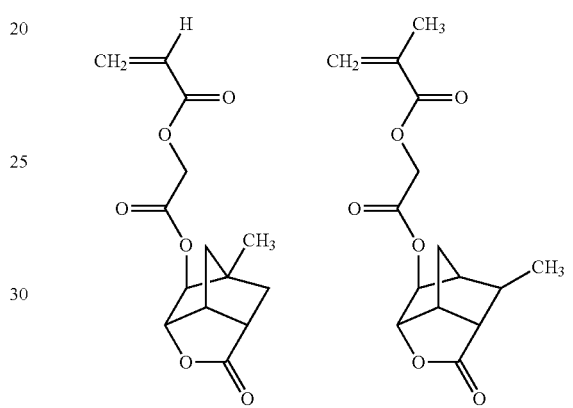
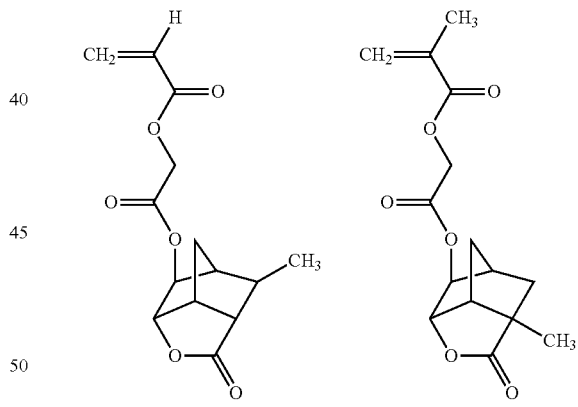
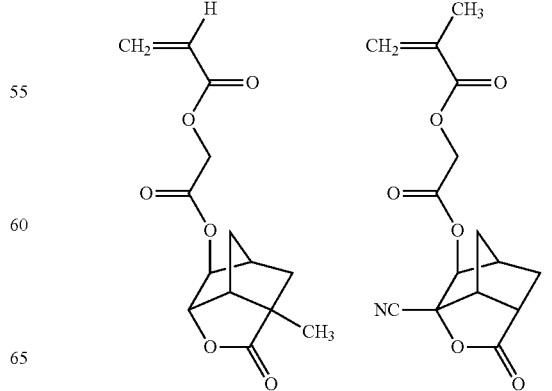

-continued
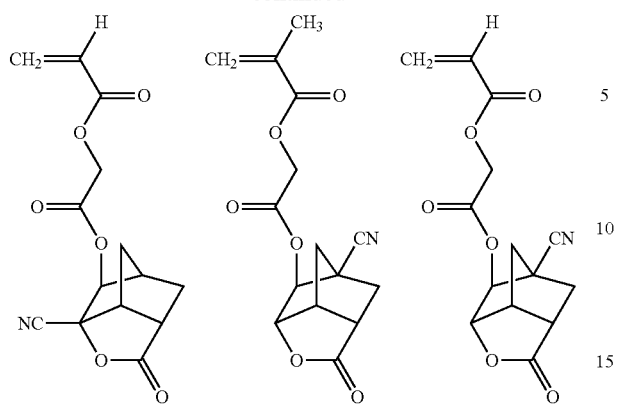
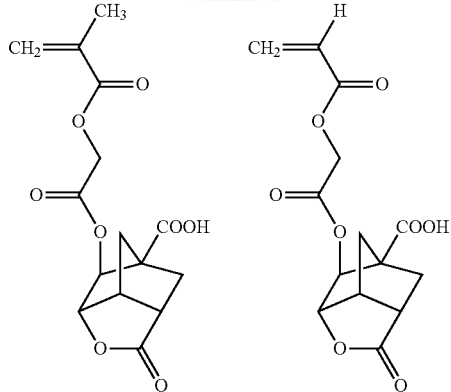
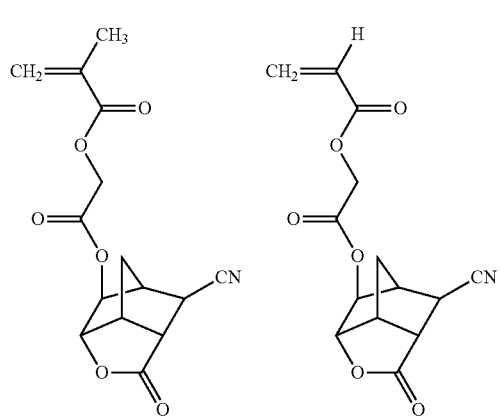
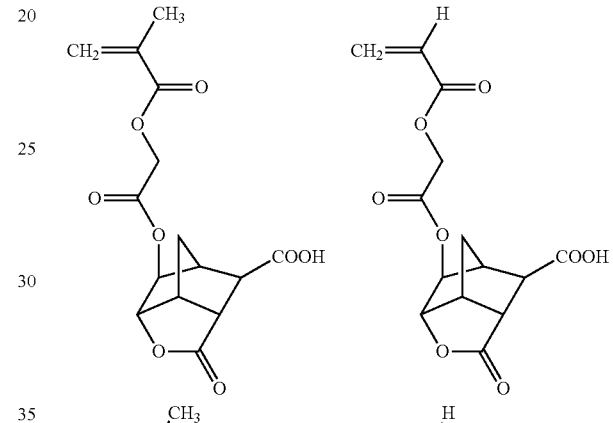
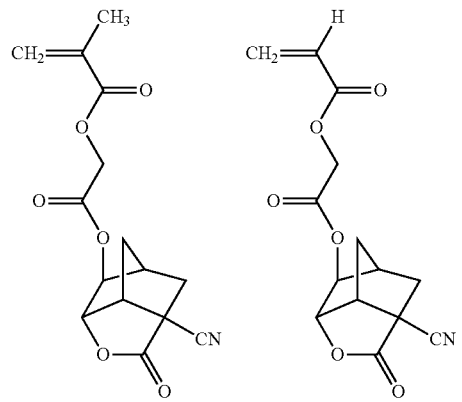
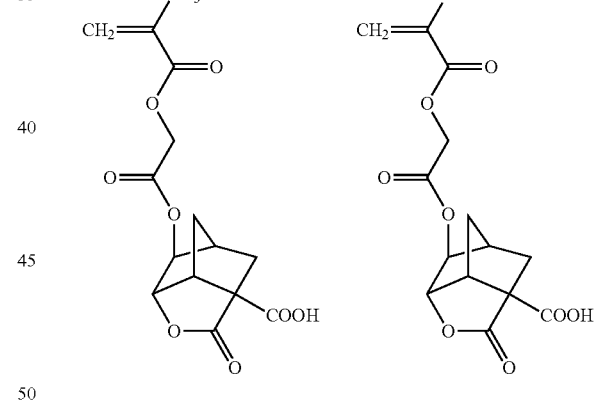
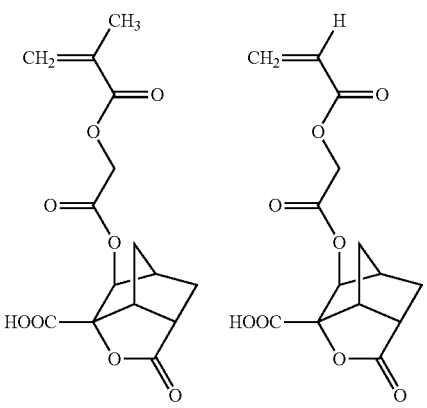
Examples of the monomer represented by the formula (a3-3) include the followings.
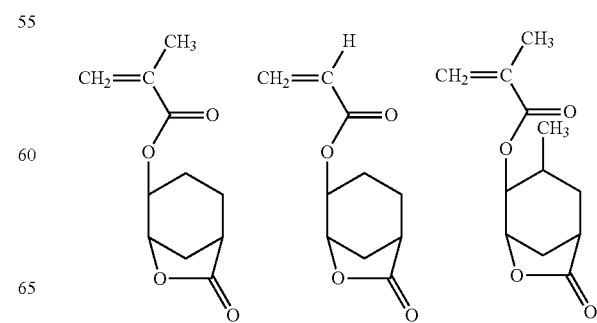

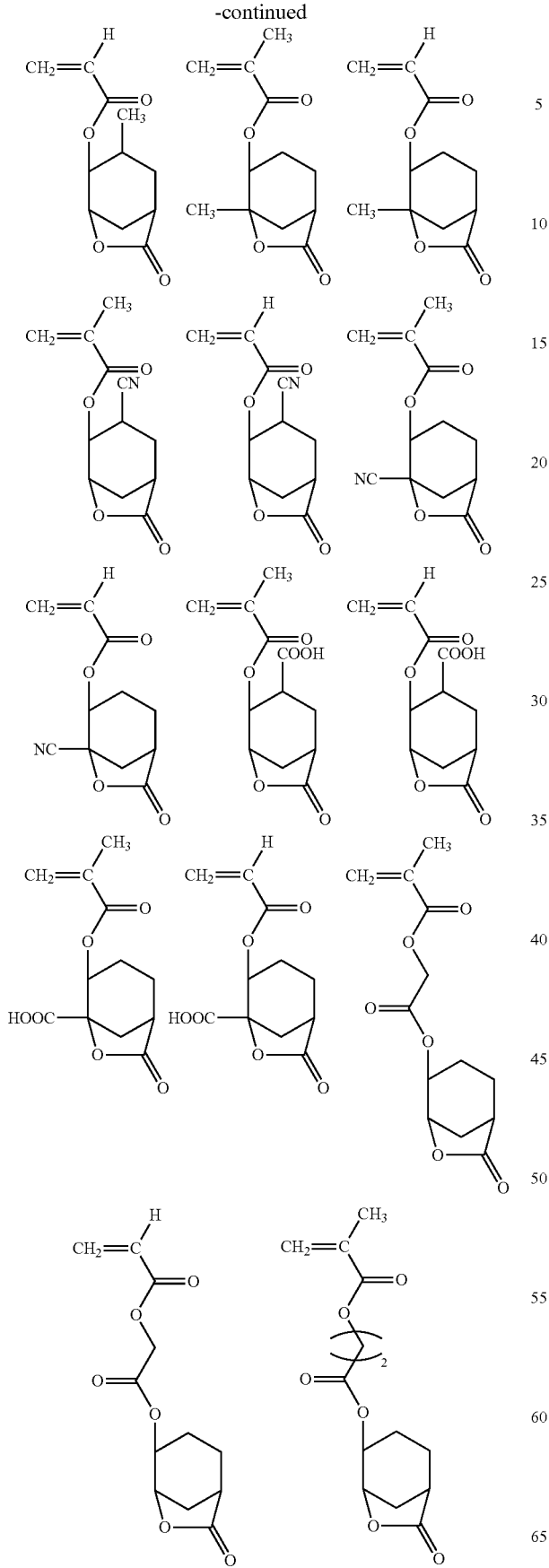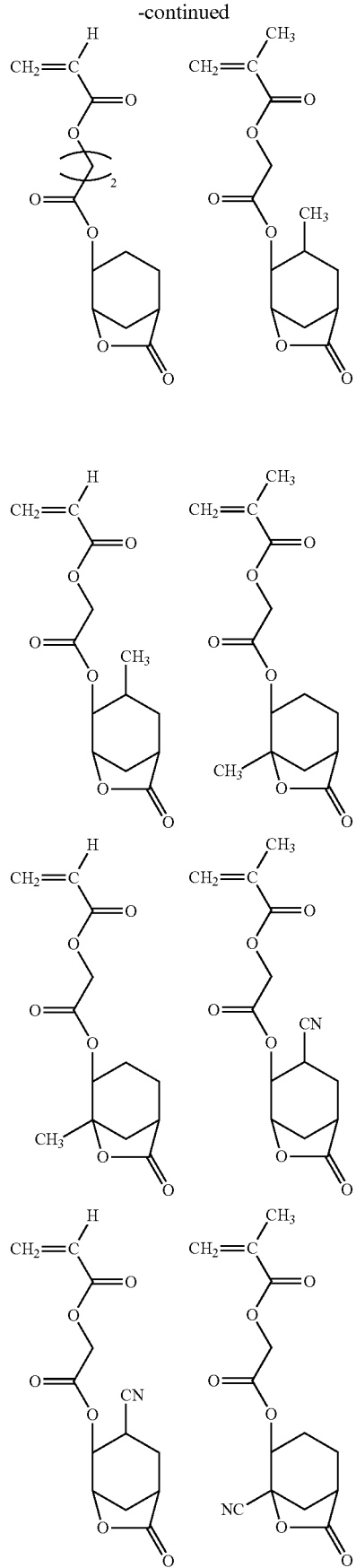

-continued

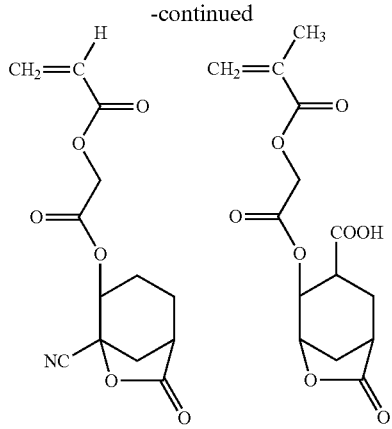

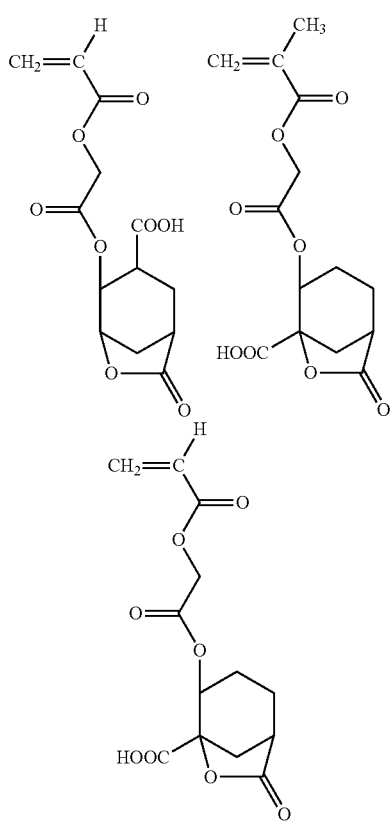

POLYMER (I) can contain a structural unit derived from a monomer having an acid-labile group containing a lactone ring. Examples of the monomer having an acid-labile group containing a lactone ring include the followings.

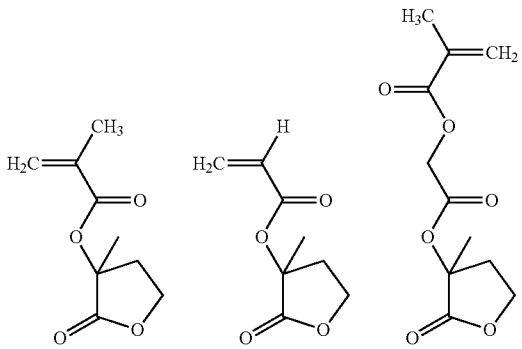

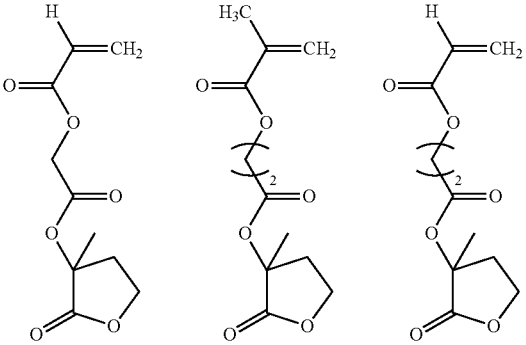

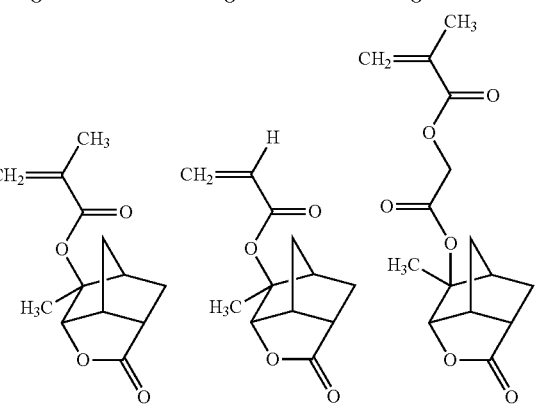

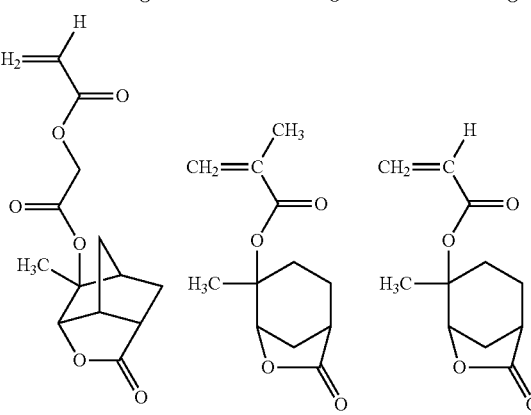

Among them, preferred are 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, tetrahydro-2-oxo-3-furyl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate, and more preferred are 5-oxo-4-oxatricyclo[4.2.1.0$^{3,7}$]nonan-2-yl methacrylate, tetrahydro-2-oxo-3-furyl methacrylate and 2-(5-oxo-4-oxatricyclo[4.2.1.0$^{3,7}$]nonan-2-yloxy)-2-oxoethyl methacrylate.

When POLYMER (I) contains the structural unit derived from MONOMER (a3), the content thereof is usually 5 to 70% by mole and preferably 10 to 65% by mole and more preferably 10 to 60% by mole based on total molar of all the structural units of POLYMER (I).

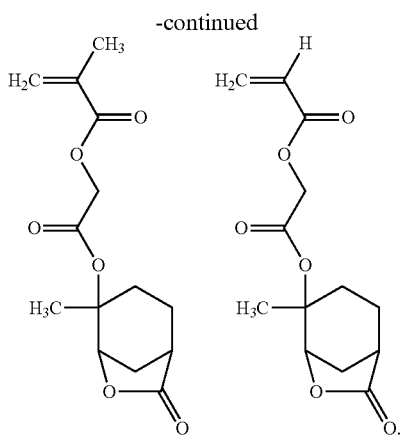

Examples of the other monomer having no acid-labile group include the monomers represented by the formulae (a4-1), (a4-2) and (a4-3):

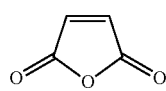
(a4-1)

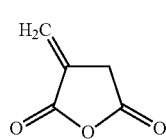
(a4-2)

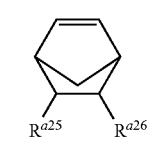
(a4-3)

wherein $R^{a25}$ and $R^{a26}$ independently represents a hydrogen atom, a C1-C3 aliphatic hydrocarbon group which can have one or more substituents, a carboxyl group, a cyano group or a —COOR$^{a27}$ group in which $R^{a27}$ represents a C1-C36 aliphatic hydrocarbon group or a C3-C36 saturated cyclic hydrocarbon group, and one or more —CH$_2$— in the C1-C36 aliphatic hydrocarbon group and the C3-C36 saturated cyclic hydrocarbon group can be replaced by —O— or —CO—, with the proviso that the carbon atom bonded to —O— of $R^{a27}$ of —COOR$^{a27}$ is not a tertiary carbon atom, or $R^{a25}$ and $R^{a26}$ are bonded together to form a carboxylic anhydride residue represented by —C(=O)OC(=O)—.

Examples of the substituent of the C1-C3 aliphatic hydrocarbon group include a hydroxyl group. Examples of the C1-C3 aliphatic hydrocarbon group which can have one or more substituents include a C1-C3 alkyl group such as a methyl group, an ethyl group and a propyl group, and a C1-C3 hydroxyalkyl group such a hydroxymethyl group and a 2-hydroxyethyl group. The C1-C36 aliphatic hydrocarbon group represented by $R^5$ is preferably a C1-C8 aliphatic hydrocarbon group and is more preferably a C1-C6 aliphatic hydrocarbon group. The C3-C36 saturated cyclic hydrocarbon group represented by $R^{25}$ is preferably a C4-C36 saturated cyclic hydrocarbon group, and is more preferably C4-C12 saturated cyclic hydrocarbon group. Examples of $R^{25}$ include a methyl group, an ethyl group, a propyl group, a 2-oxooxolan-3-yl group and a 2-oxo-oxolan-4-yl group.

Examples of the monomer represented by the formula (a4-3) include 2-norbornene, 2-hydroxy-5-norbornene, 5-norbornene-2-carboxylic acid, methyl 5- norbornene-2-carboxylate, 2-hydroxyethyl 5-norbornene-2-carboxylate, 5-norbornene-2-methanol and 5- norbornene-2,3-dicarboxylic anhydride.

When POLYMER (I) contains a structural unit derived from a monomer represented by the formula (a4-1), (a4-2) or (a4-3), the content thereof is usually 2 to 40% by mole and preferably 3 to 30% by mole and more preferably 5 to 20% by mole based on total molar of all the structural units of POLYMER (I).

Preferable POLYMER (I) is a polymer consisting of one or more structural units derived from SALT (I), one or more structural units derived from MONOMER (a1) and the structural units derived from, MONOMER (a2) and/or MONOMER (a3). MONOMER (a1) is preferably the monomer represented by the formula (a1-1) or the monomer represented by the formula (a1-2), and is more preferably the monomer represented by the formula (a1-1). MONOMER (a2) is preferably the monomer represented by the formula (a2-1), and MONOMER (a3) is preferably the monomer represented by the formula (a3-1) or (a3-2).

POLYMER (I) can be produced according to known polymerization methods such as radical polymerization.

POLYMER (I) usually has 2,500 or more of the weight-average molecular weight, and preferably 3,000 or more of the weight-average molecular weight. POLYMER (I) usually has 50,000 or less of the weight-average molecular weight, and preferably has 30,000 or less of the weight-average molecular weight. The weight-average molecular weight can be measured with gel permeation chromatography.

The first photoresist composition of the present invention comprises the acid generator of the present invention and a resin having an acid-labile group, being insoluble or poorly soluble in an aqueous alkali solution but becoming soluble in an aqueous alkali solution by the action of an acid.

The content of the acid generator in the first photoresist composition is usually 1 part by weight or more relative to 100 parts by weight of the resin and preferably 3 parts by weight or more. The content of the acid generator in the first photoresist composition is usually 30 parts by weight or less relative to 100 parts by weight of the resin and preferably 25 parts by weight or less.

The resin in the first photoresist composition has one or more structural units derived from monomers other than SALT (I).

The resin is insoluble or poorly soluble in an alkali aqueous solution but becomes soluble in an alkali aqueous solution by the action of an acid. The resin has one or more acid-labile groups.

Examples of the acid-labile group include the same as described above, and examples of the monomer having an acid-labile group include the same as described above.

Preferable examples of MONOMER (a1) include the monomers represented by the formulae (a1-1) and (a1-2).

The resin preferably contains one or more structural units derived from MONOMER (a2), and the resin also preferably contains one or more structural units derived from MONOMER (a3).

The resin can be produced by polymerizing one or more MONOMER (a1) or polymerizing one or more MONOMER (a1) and other monomers.

The content of the structural unit derived from Monomer (a1) in the resin is usually 10 to 95% by mole and preferably 15 to 90% by mole and more preferably 20 to 85% by mole based on total molar of all the structural units of the resin.

The content of the structural units derived from MONOMER (a2) is usually 0.1 to 40% by mole, preferably 0.1 to 35% by mole and more preferably 1 to 20% by mole based on 100% by mole of all the structural units of the resin. When the resin has the structural unit derived from MONOMER (a3), the content thereof is usually 1 to 80% by mole, preferably 10 to 00% by mole and more preferably 30 to 70% by mole based on 100% by mole of all the structural units of the resin.

Preferable resin is a resin comprising the structural units derived from MONOMER (a1) and the structural units derived from MONOMER (a2) and/or MONOMER (a3). MONOMER (a1) is preferably the monomer represented by the formula (a1-1) or the monomer represented by the formula (a1-2) and is more preferably the monomer represented by the formula (a1-1). MONOMER (a2) is preferably the monomer represented by the formula (a2-1), and MONOMER (a3) is preferably the monomer represented by the formula (a3-1) or (a3-2).

The resin can be produced according to known polymerization methods such as radical polymerization.

The resin usually has 2,500 or more of the weight-average molecular weight, and preferably 3,000 or more of the weight-average molecular weight. The resin usually has 50,000 or less of the weight-average molecular weight, and preferably has 30,000 or less of the weight-average molecular weight.

The content of the resin in the first photoresist composition of the present invention is preferably 80% by weight or more based on 100% by weight of the solid component. In this specification, "solid component" means components other than solvents in the photoresist composition. The content of the solid component can be analyzed with conventional means such as liquid chromatography and gas chromatography.

The acid generator of the present invention comprises SALT (I). The acid generator of the present invention can contain two or more kinds of SALT (I). The acid generator of the present invention can contain one or more known acid generators other than SALT (I) in addition to SALT (I). The photoresist composition preferably contains SALT (I) and one or more acid generators other than SALT (I) as the acid generator. The acid generator of the present invention contains SALT (I) in an effective amount.

Examples of the photoacid generator other than SALT (I) include nonionic photoacid generators and ionic photoacid generators. Examples of the nonionic photoacid generator include organic halides, sulfonate esters such as 2-nitrobenzyl ester, aromatic sulfonate, oxime sulfonate, N-sulfonyloxyimide, sulfonyloxyketone and DNQ 4-sulfonate, and sulfones such as disulfone, ketosulfone and sulfonyldiazomethane. Examples of the ionic photoacid generator include onium salts such as a diazonium salt, a phosphonium salt, a sulfonium salt and an iodonium salt, and examples of the anion of the onium salt include sulfonic acid anion, sulfonylimide anion and sulfonylmethide anion.

Other examples of the photoacid generator other than SALT (I) include photoacid generators described in JP 63-26653 A, JP 55-164824 A, JP 62-69263 A, JP 63-146038 A, JP 63-163452 A, JP 62-153853 A, JP 63-146029 A, U.S. Pat. No. 3,779,778, U.S. Pat. No. 3,849,137, DE Patent No. 3914407 and EP Patent No. 126,712.

A fluorine-containing photoacid generator is preferable.

Preferable examples of the acid generator other than SALT (I) include a salt represented by the formula (B1):

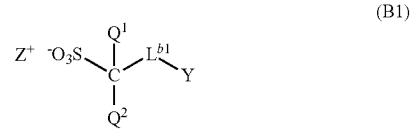

wherein $Q^1$ and $Q^2$ independently represent a fluorine atom or a C1-C6 perfluoroalkyl group,
$L^{b1}$ represents a single bond or a C1-C17 saturated divalent hydrocarbon group which can have one or more substituents, and one or more —$CH_2$— in the saturated divalent hydrocarbon group can be replaced by —O— or —CO—,
Y represents a C1-C18 aliphatic hydrocarbon group or a C3-C18 saturated cyclic hydrocarbon group, and the aliphatic hydrocarbon group and the saturated cyclic hydrocarbon group can have one or more substituents, and one or more —$CH_2$— in the aliphatic hydrocarbon group and the saturated cyclic hydrocarbon group can be replaced by —O—, —CO— or —$SO_2$—, and
$Z^+$ represents an organic cation.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ independently preferably represent a fluorine atom or a trifluoromethyl group and $Q^1$ and $Q^2$ are more preferably fluorine atoms.

Examples of the C1-C17 saturated divalent hydrocarbon group include a C1-C17 alkylene group and a divalent group having an alicyclic divalent hydrocarbon group. Examples of the alkylene group include a linear alkanediyl group such as a methylene group, an ethylene group, a propane-1,3-diyl group, a butane-1,4-diyl group, a pentane-1,5-diyl, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, a branched chain alkanediyl group formed by replacing one or more hydrogen atom of the above-mentioned linear alkanediyl group by a C1-C4 alkyl group, and
a divalent group having an alicyclic divalent hydrocarbon group such as the following groups represented by the formulae ($X^1$-A) to ($X^1$-C):

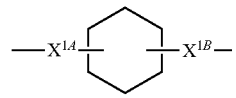

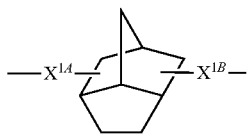
(X¹-C)

wherein $X^{1A}$ and $X^{1B}$ independently each represent a C1-C6 alkylene group which can have one or more substituents, with the proviso that total carbon number of the group represented by the formula (X¹-A), (X¹-B) or (X¹-C) is 1 to 17.

One or more —CH₂— in the C1-C6 alkanediyl group can be replaced by —O— or —CO—.

Examples of the C1-C17 saturated hydrocarbon group in which one or more —CH₂— are replaced by —O— or —CO— include the same as described in the above-mentioned $X^1$. Among them, preferred are *—CO—O-$L^{b2}$-, *—CO—O-$L^{b4}$-CO—O-$L^{b3}$-, *-$L^{b5}$-O—CO— and *-$L^{b7}$-O-$L^{b6}$-, and more preferred are *—CO—O-$L^{b2}$- and *—CO—O-$L^{b4}$-CO—O-$L^{b3}$-, and much more preferred is *—CO—O-$L^{b2}$-, and especially preferred is *—CO—O-$L^{b2}$- in which $L^{b2}$ is a single bond or —CH₂—.

Examples of the substituent in Y include a halogen atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and —(CH₂)$_{j2}$—O—CO—$R^{b1}$- in which $R^{b1}$ represents a C1-C16 aliphatic hydrocarbon group, a C3-C16 saturated cyclic hydrocarbon group or a C6-C18 aromatic hydrocarbon group and j2 represents an integer of 0 to 4. Examples of the halogen atom include a fluorine atom, a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkoxycarbonyl group include a methoxycarbonyl group, an ethoxycarbonyl group, a propoxycarbonyl group, an isopropoxycarbonyl group and a butoxycarbonyl group. Examples of the aliphatic hydrocarbon group include the same as described above. Examples of the hydroxyl-containing aliphatic hydrocarbon group include a hydroxymethyl group. Examples of the C3-C16 saturated cyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

Examples of the C1-C18 aliphatic hydrocarbon group represented by Y include a methyl group, an ethyl group, a propyl group, an isopropyl group, a butyl group, an isobutyl group, a sec-butyl group, a tert-butyl group, a pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a 2-ethylhexyl group, a nonyl group, a decyl group, an undecyl group and a dodecyl group, and a C1-C6 alkyl group is preferable. Examples of the C3-C36 saturated cyclic hydrocarbon group represented by Y include the groups represented by the formulae (Y1) to (Y26):

 (Y1)

 (Y2)

 (Y3)

 (Y4)

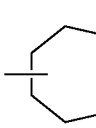 (Y5)

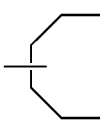 (Y6)

 (Y7)

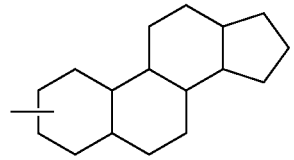 (Y8)

 (Y9)

 (Y10)

 (Y11)

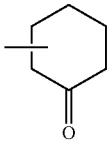 (Y12)

 (Y13)

 (Y14)

-continued (Y15) 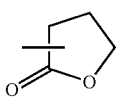

(Y16) 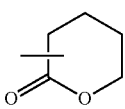

(Y17) 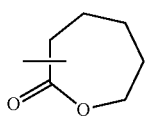

(Y18) 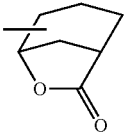

(Y19) 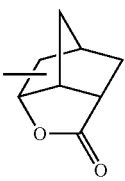

(Y20) 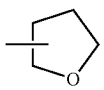

(Y21) 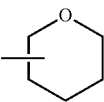

(Y22) 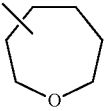

(Y23) 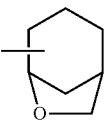

(Y24) 

(Y25) 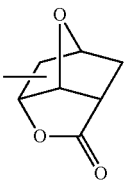

-continued (Y26) 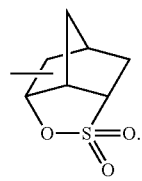

Among them, preferred are the groups represented by the formulae (Y1) to (Y19), and more preferred are the groups represented by the formulae (Y11), (Y14), (Y15) and (Y19). The groups represented by the formulae (Y11) and (Y14) are especially preferable.

Examples of Y having one or more substituents include the followings:

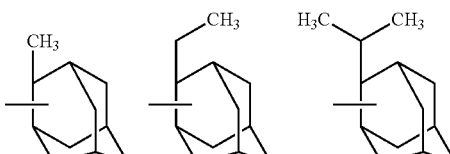

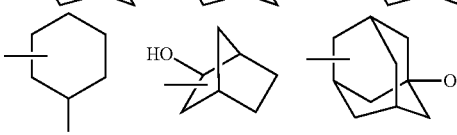

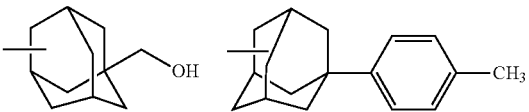

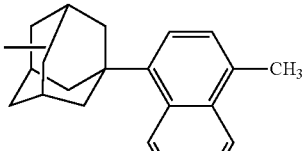

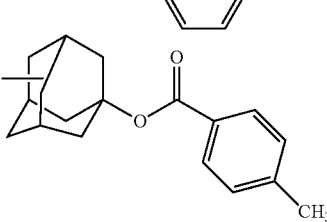

Y is preferably an adamantyl group which can have one or more substituents, and is more preferably an adamantyl group or an oxoadamantyl group.

Among the sulfonic acid anions of the salt represented by the formula (B1), preferred is a sulfonic acid anion in which $L^{b1}$ is *—CO—O-$L^{b2}$-, and more preferred are anions represented by the formulae (b1-1-1) to (b1-1-9).

(b-1-1-1) 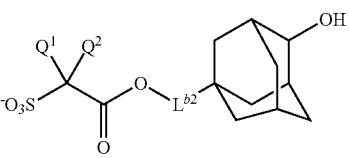

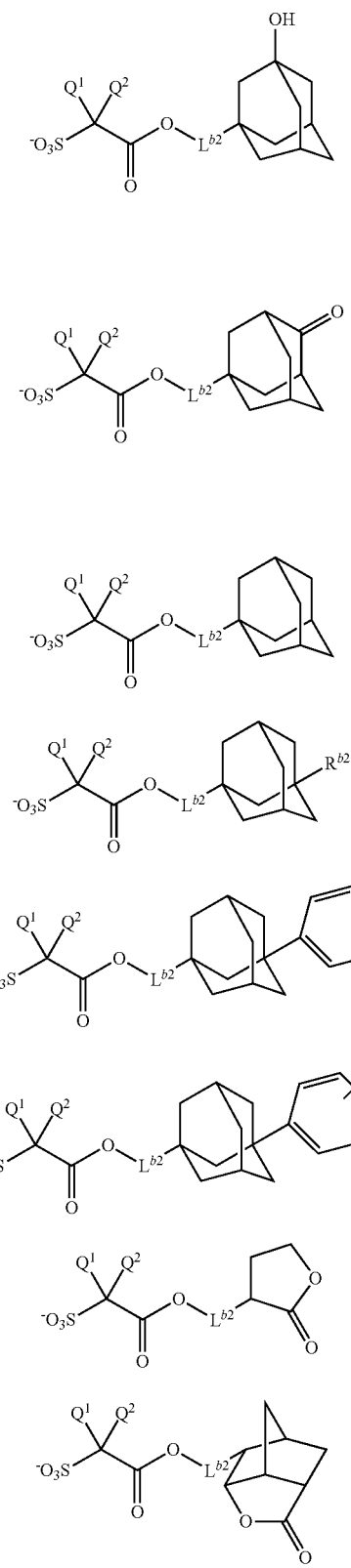
Examples of the anions of the salt represented by the formula (B1) include the followings.
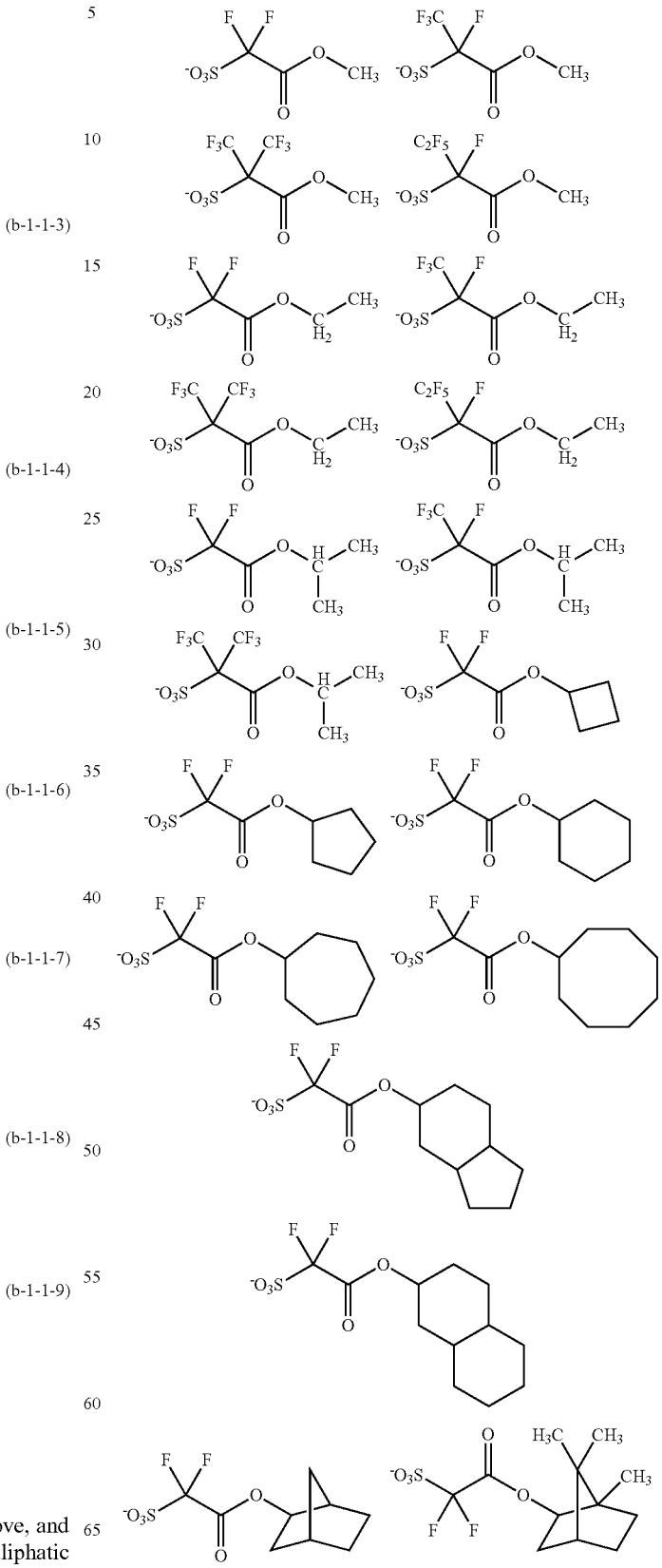
wherein $Q^1$, $Q^2$ and $L^{b2}$ are the same as defined above, and $R^{b2}$ and $R^{b3}$ each independently represent a C1-C4 aliphatic hydrocarbon group, preferably a methyl group.

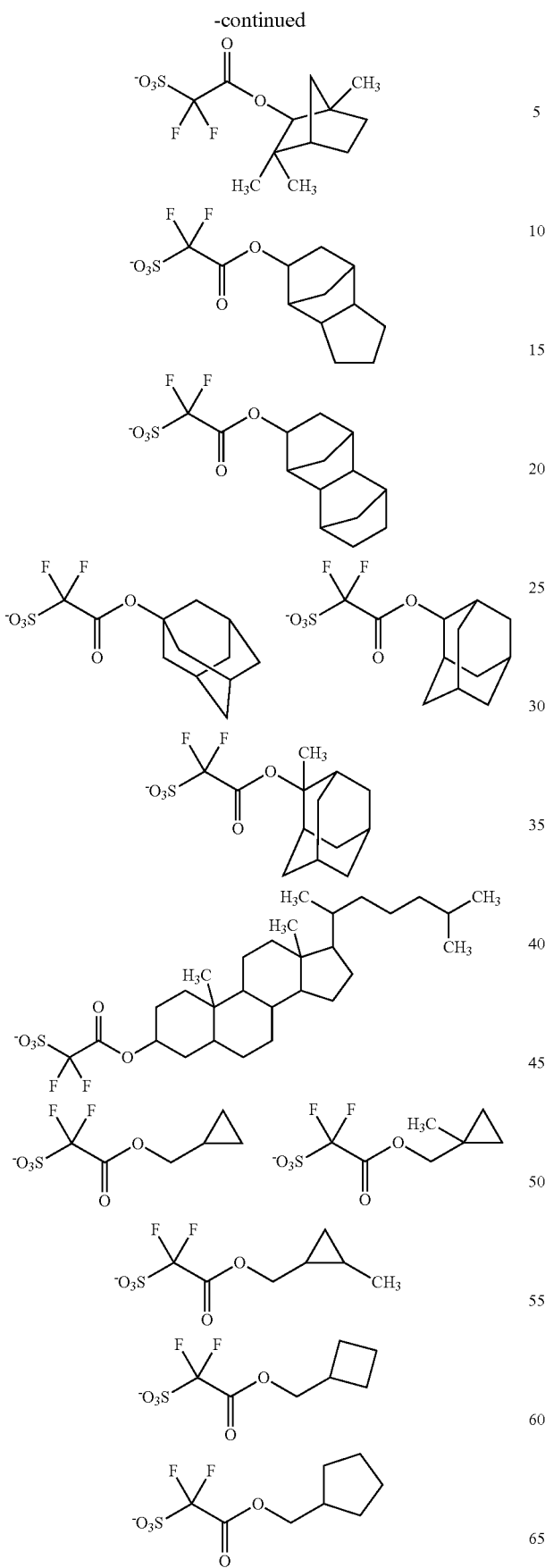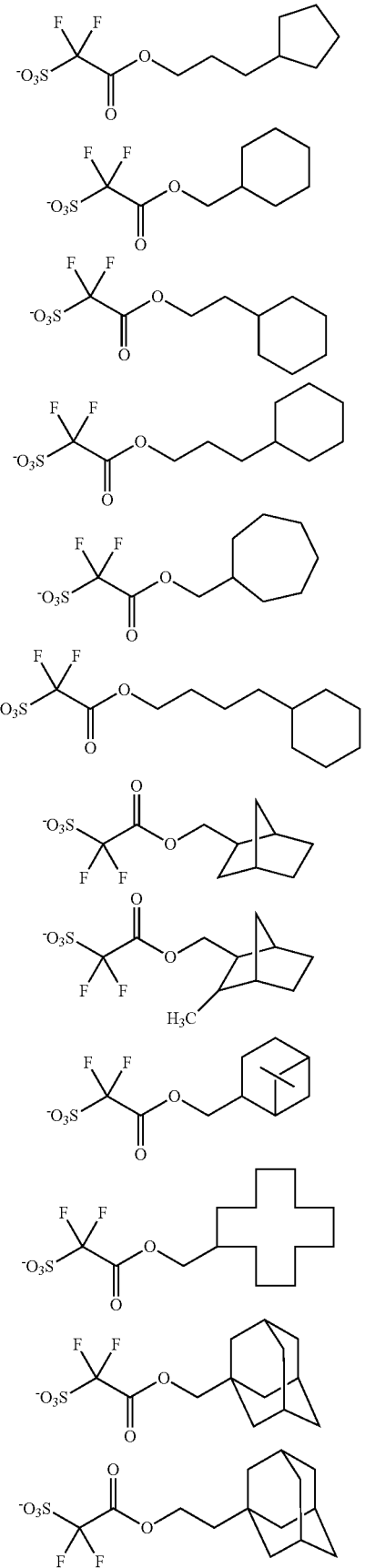

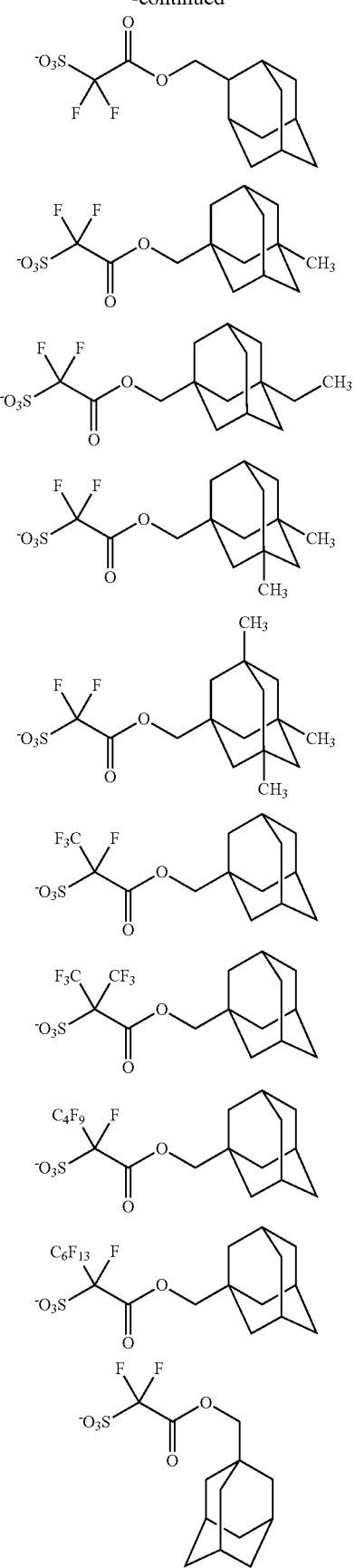
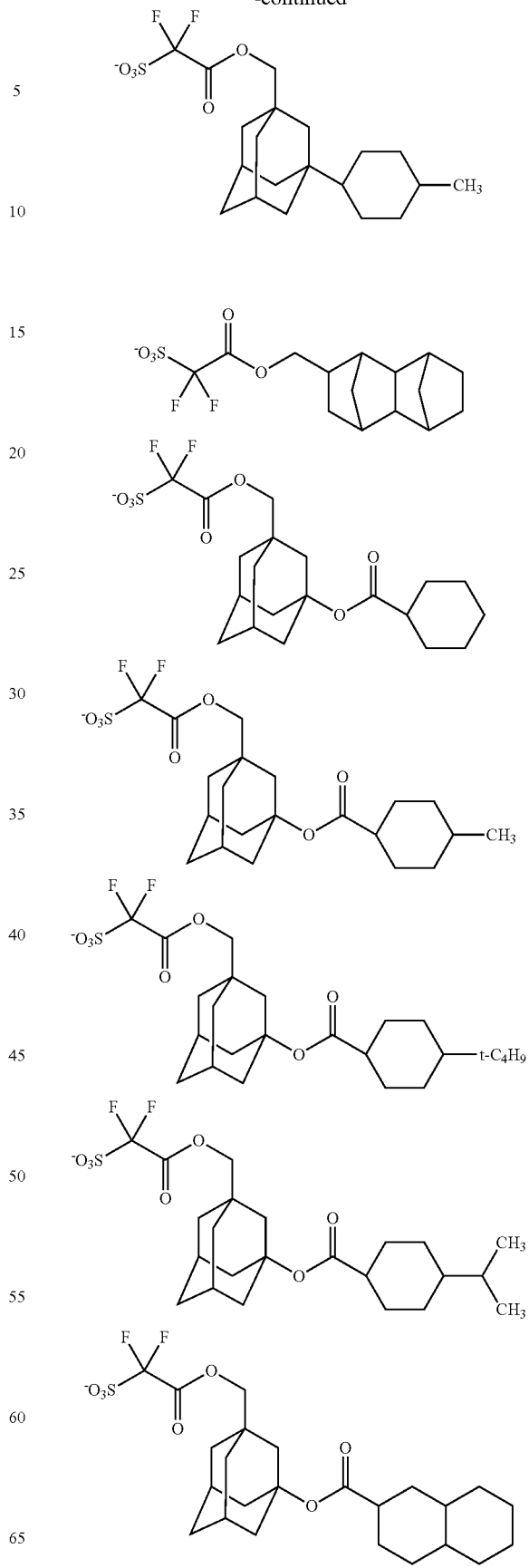

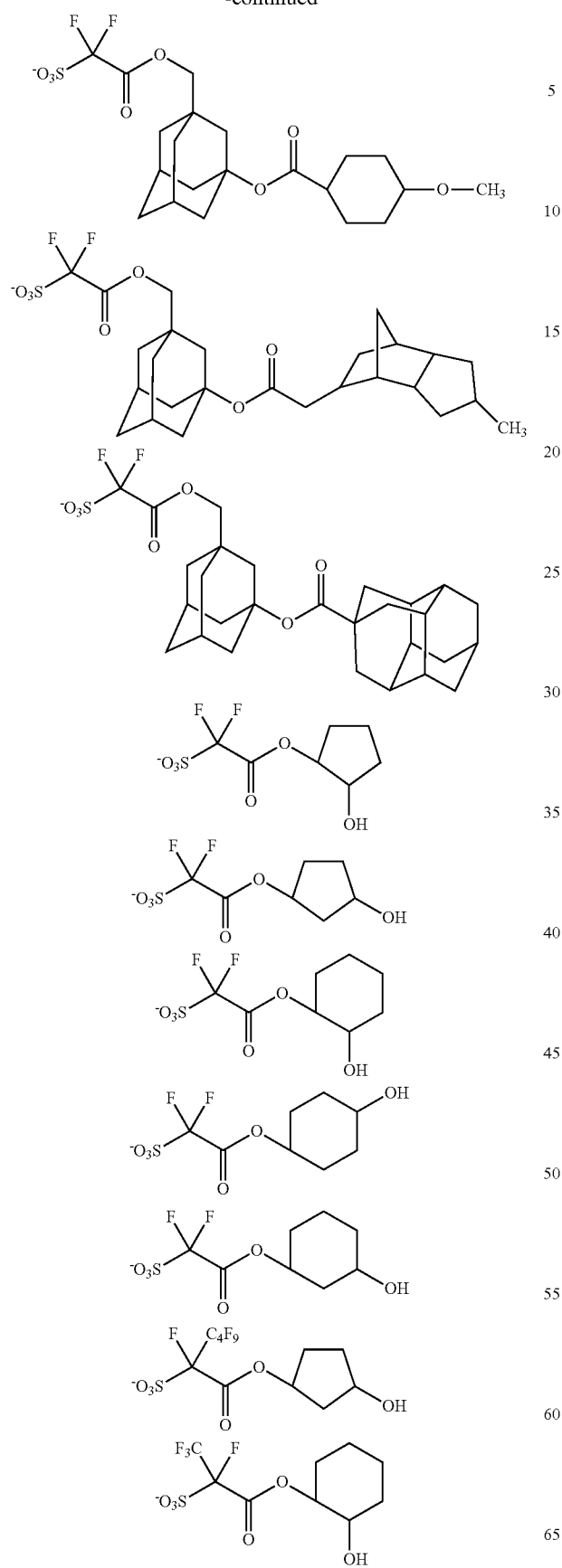
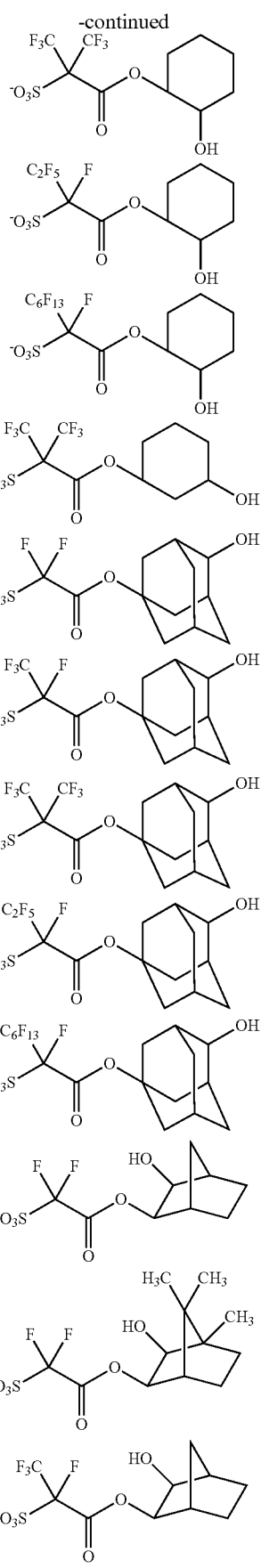

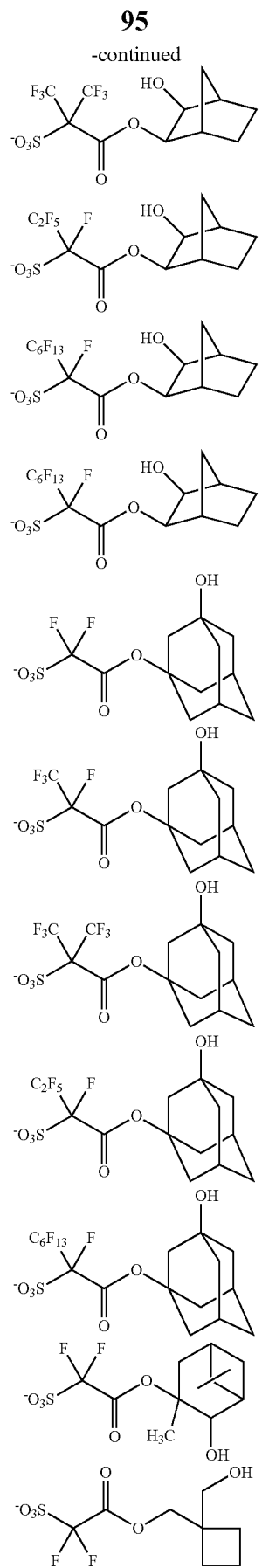
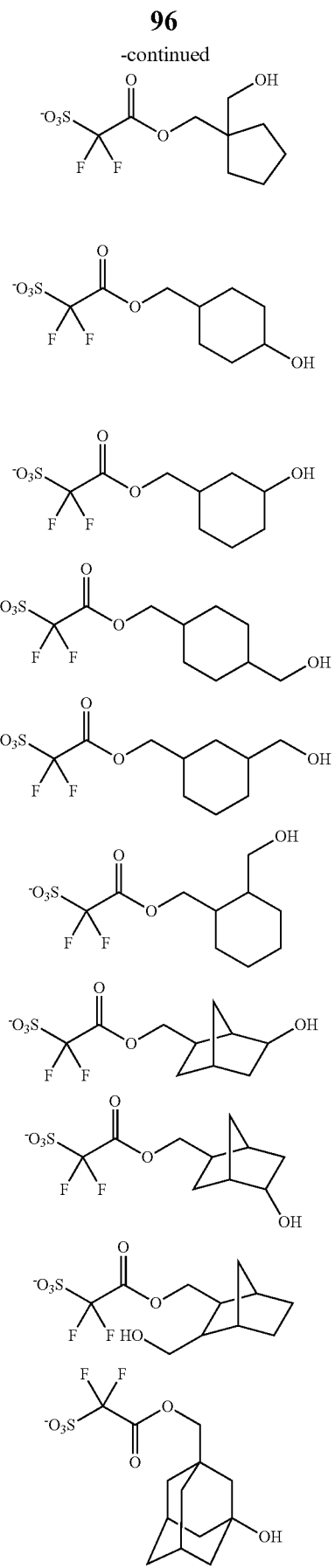

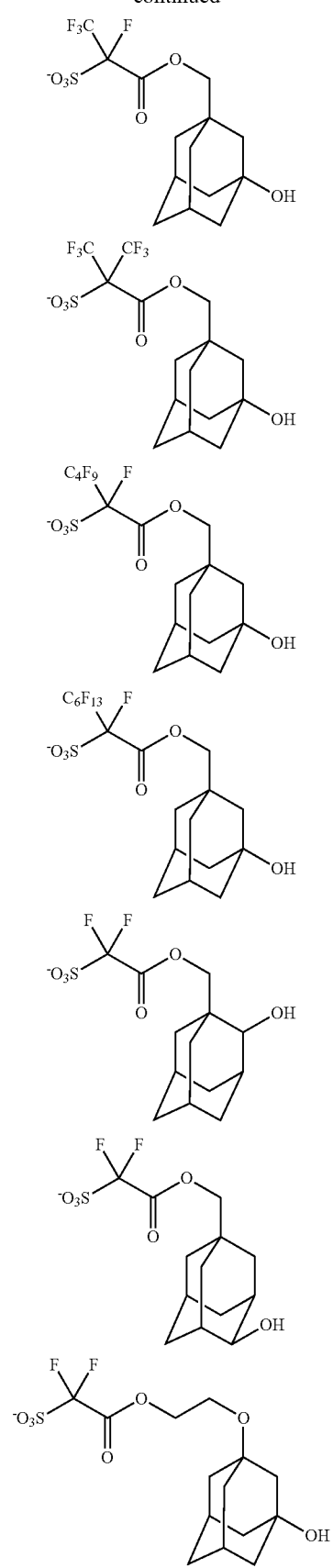
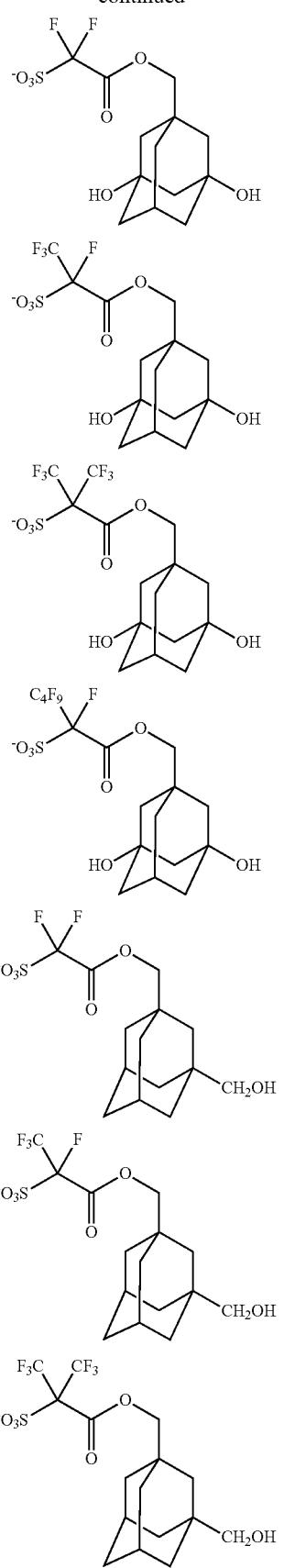

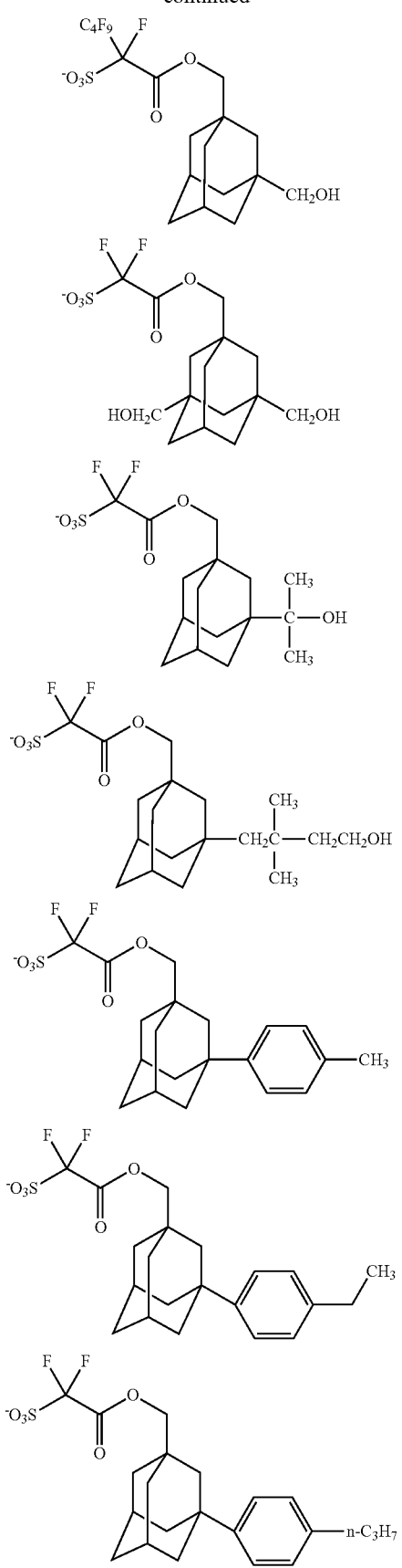
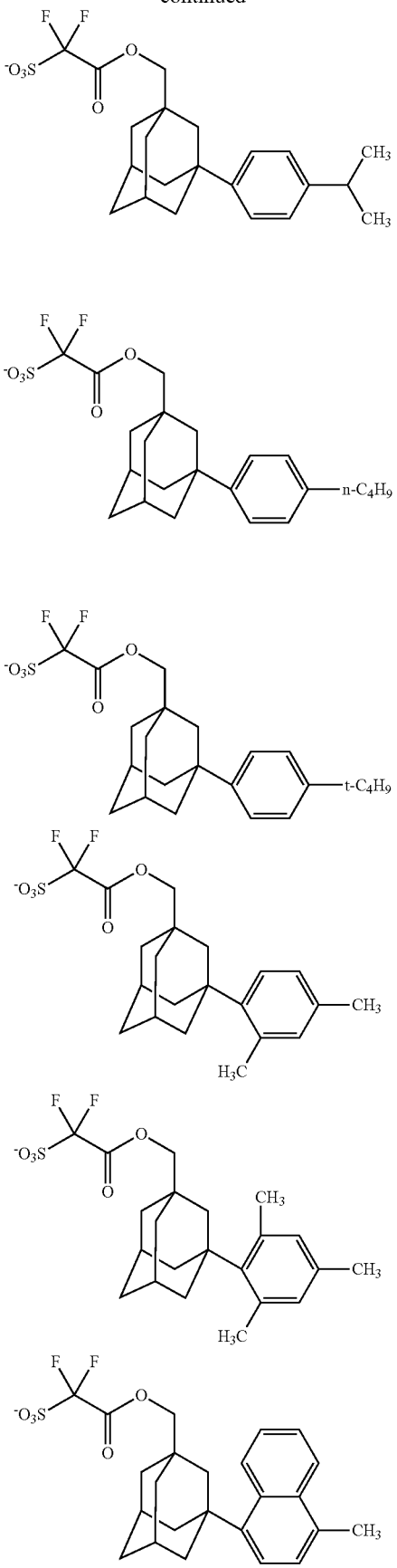

-continued
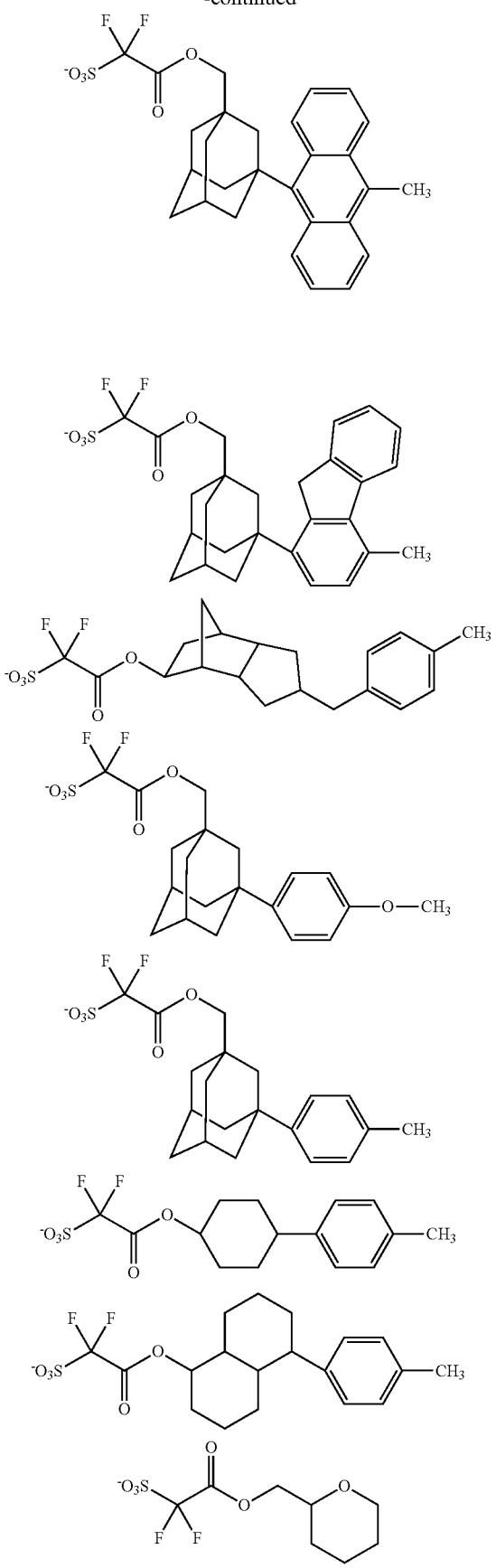
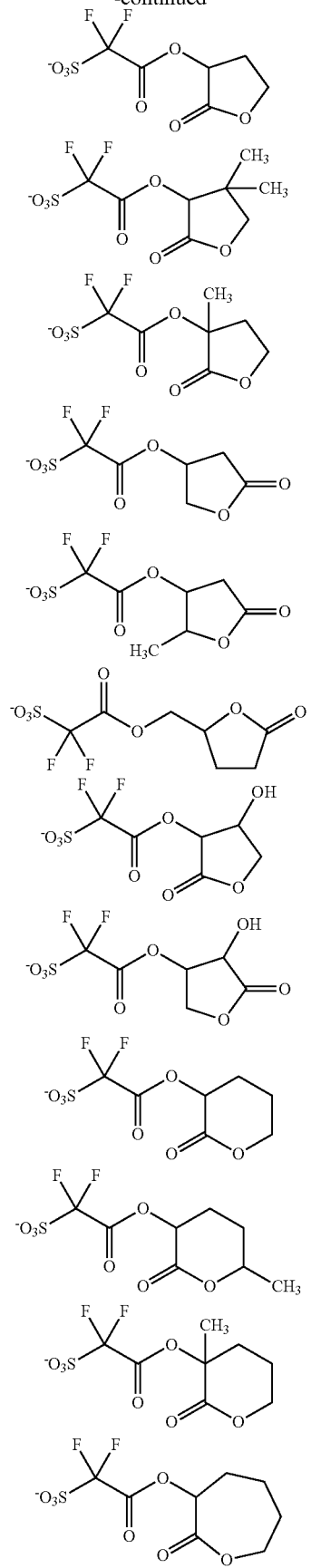

103    104
-continued    -continued
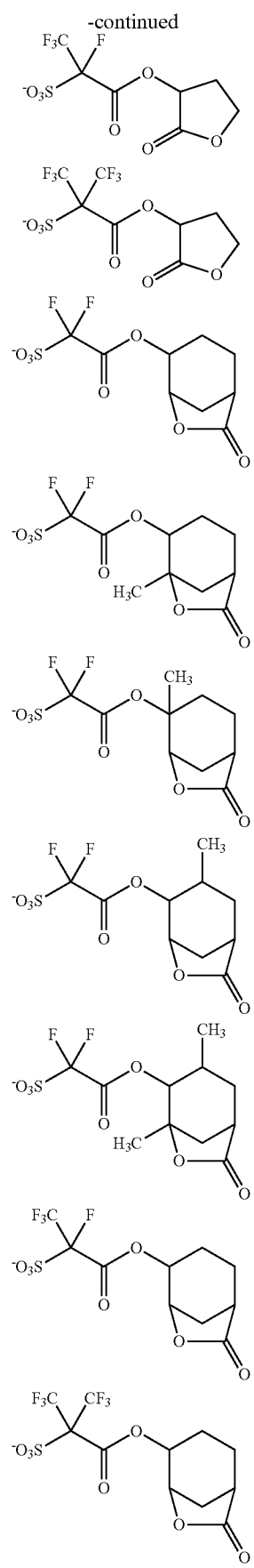
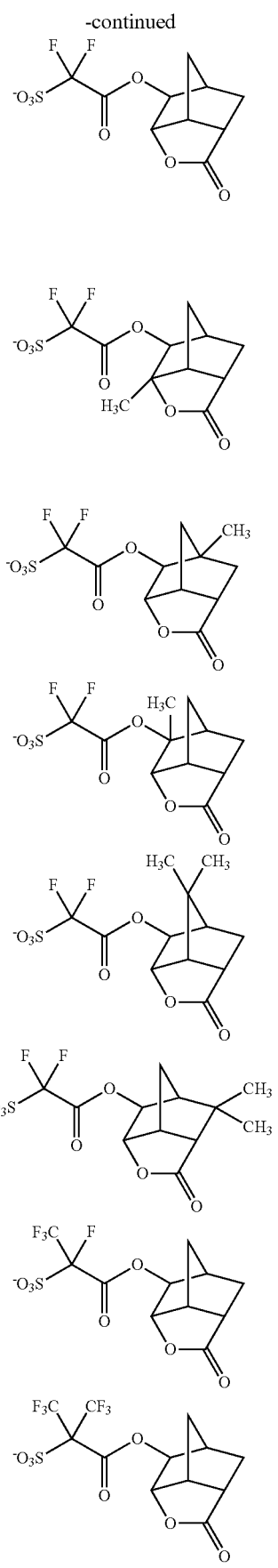

-continued
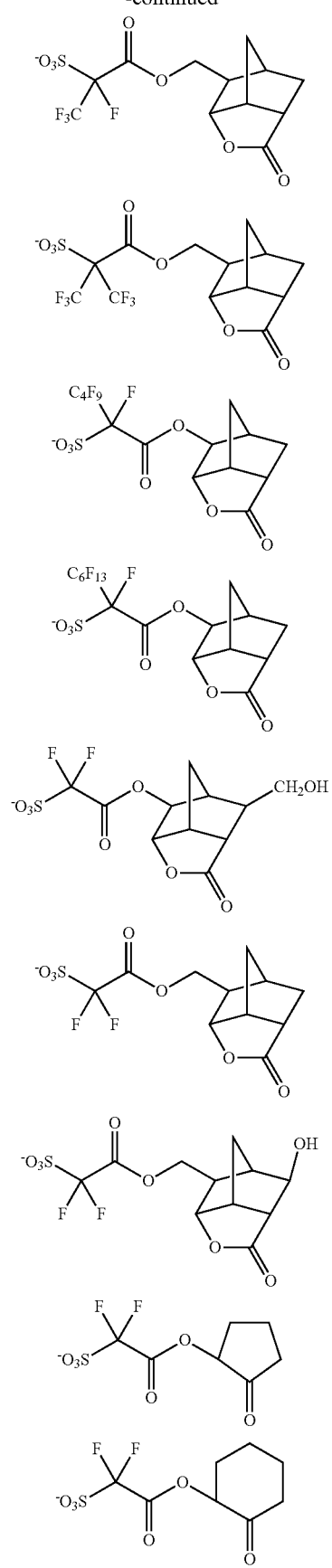
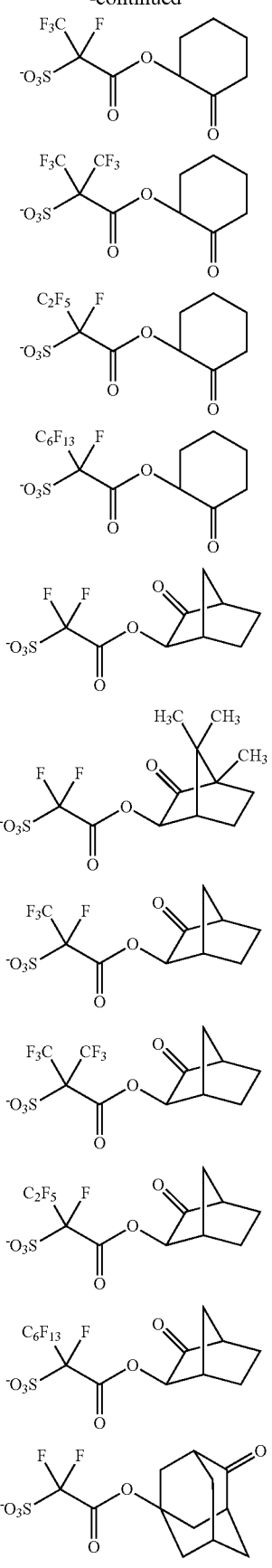

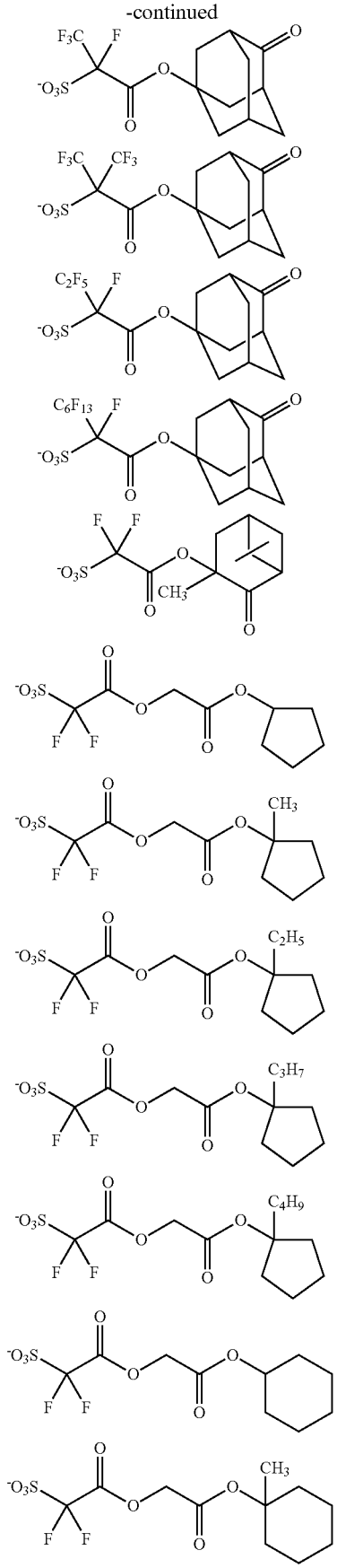
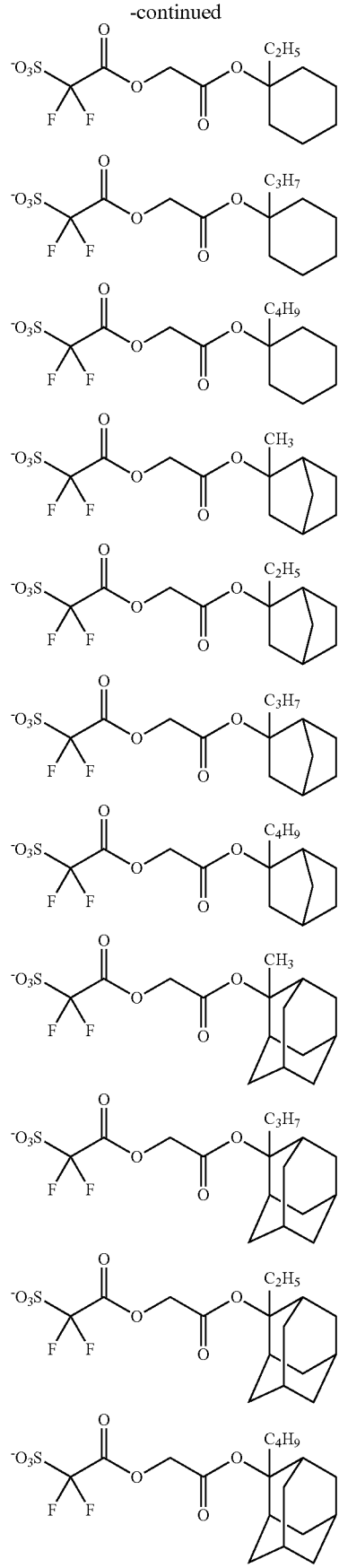

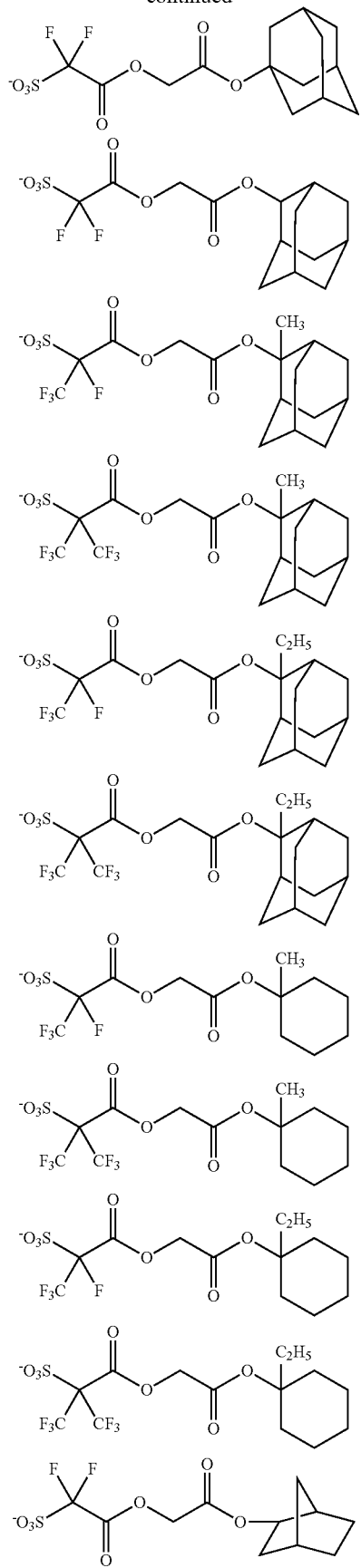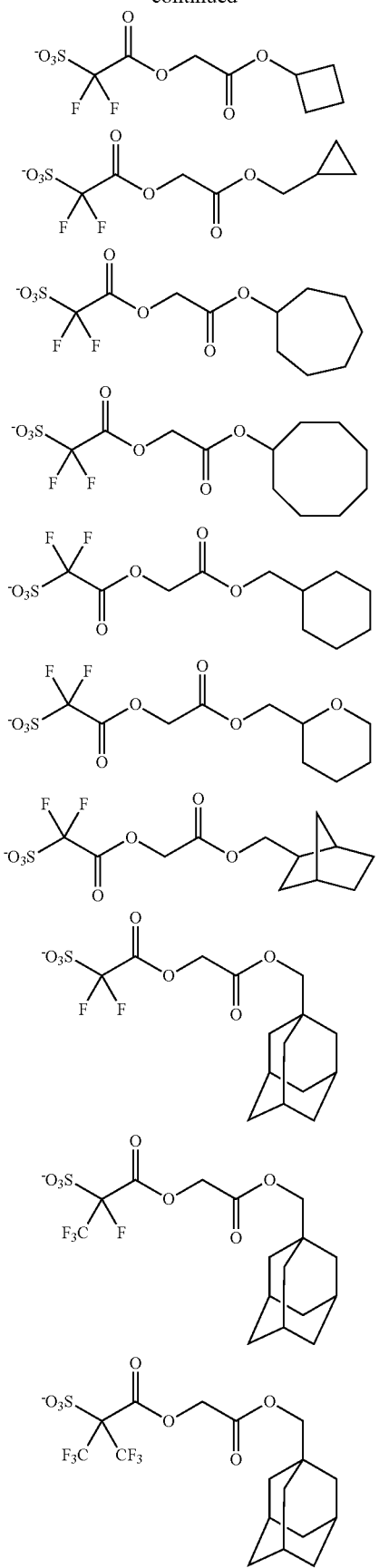

111
-continued
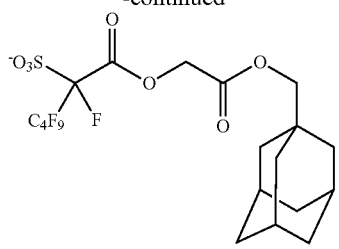
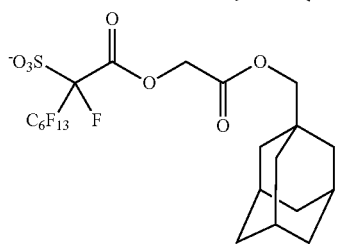
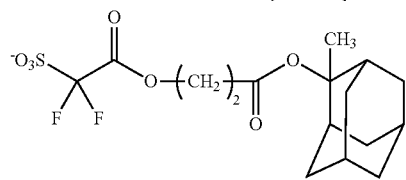
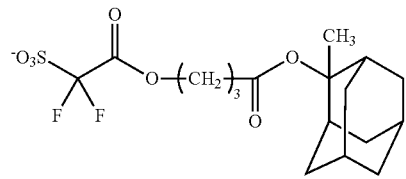
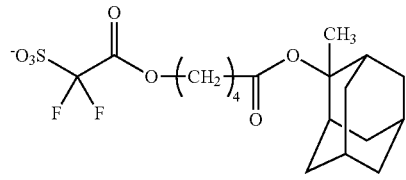
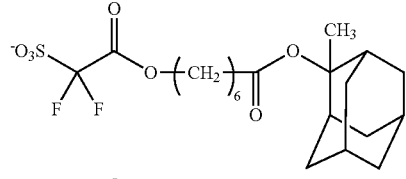
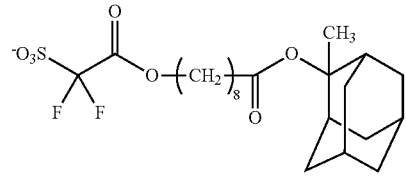
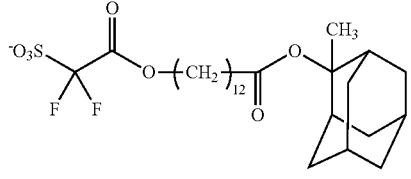
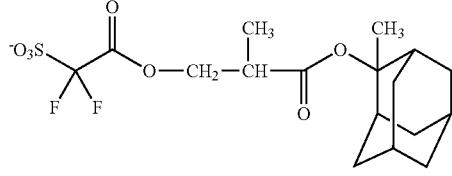
112
-continued
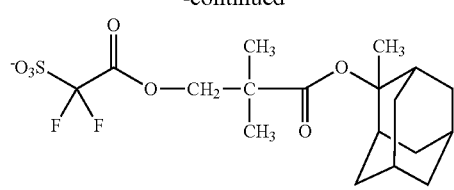
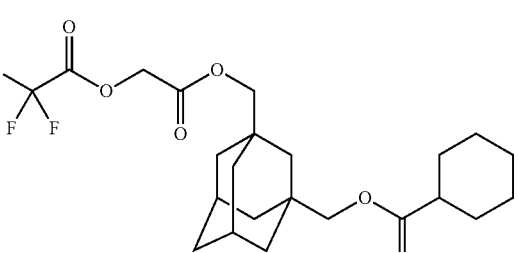
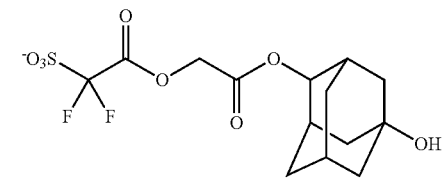
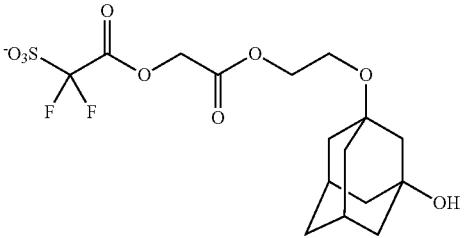
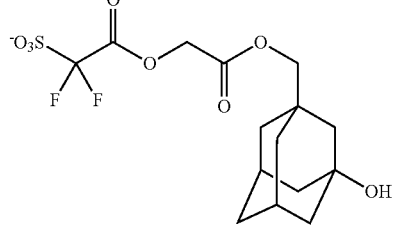
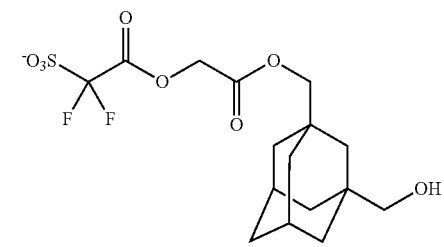
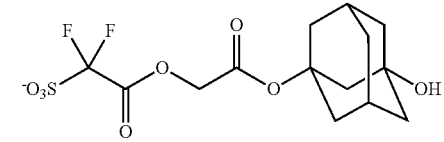
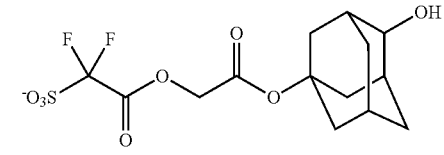

113
-continued
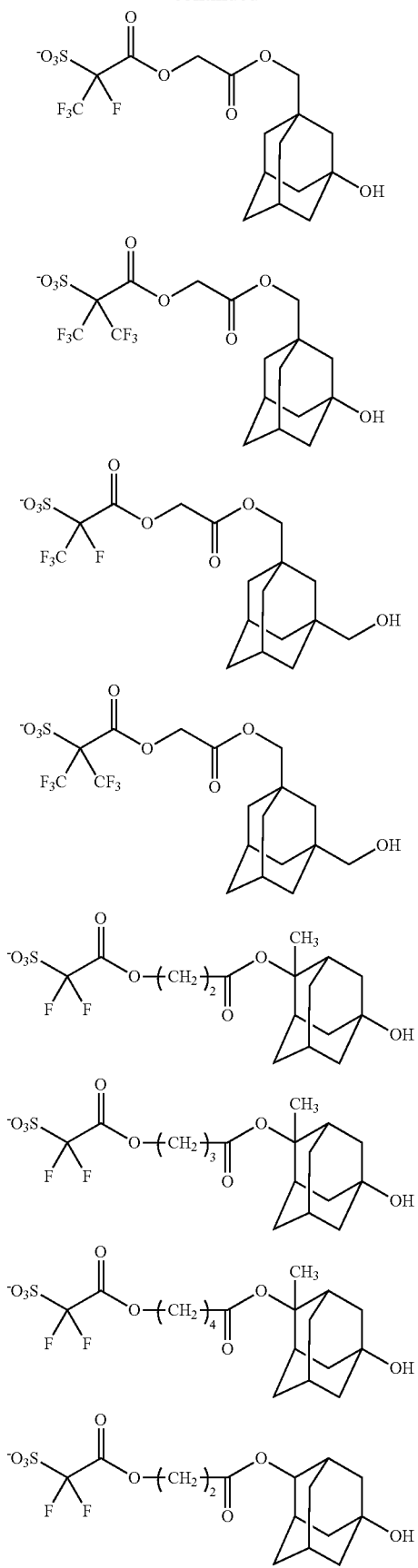
114
-continued
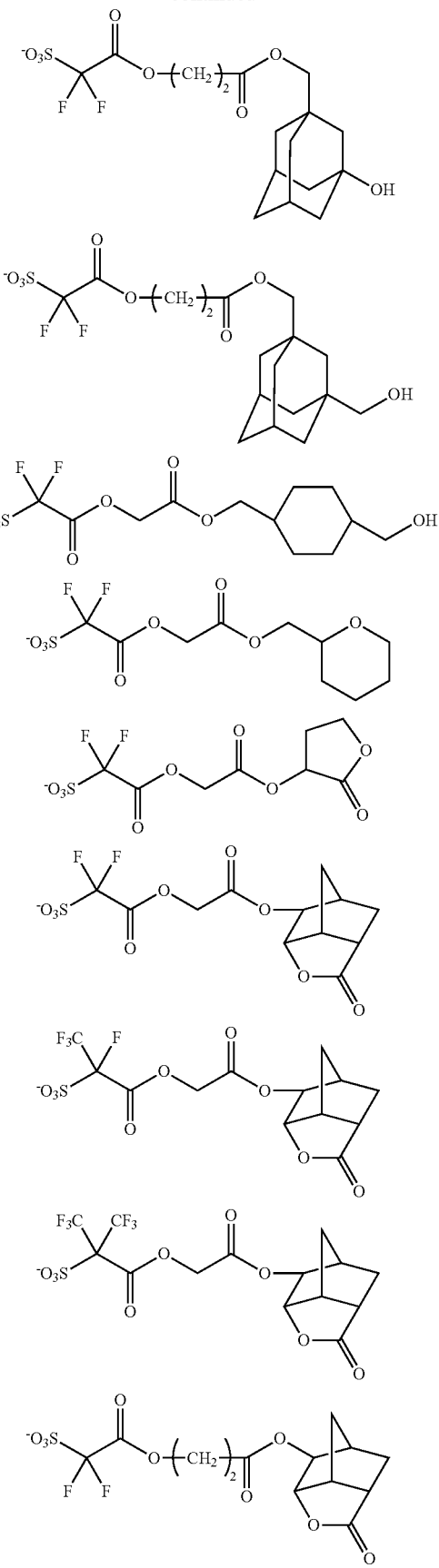

115
-continued
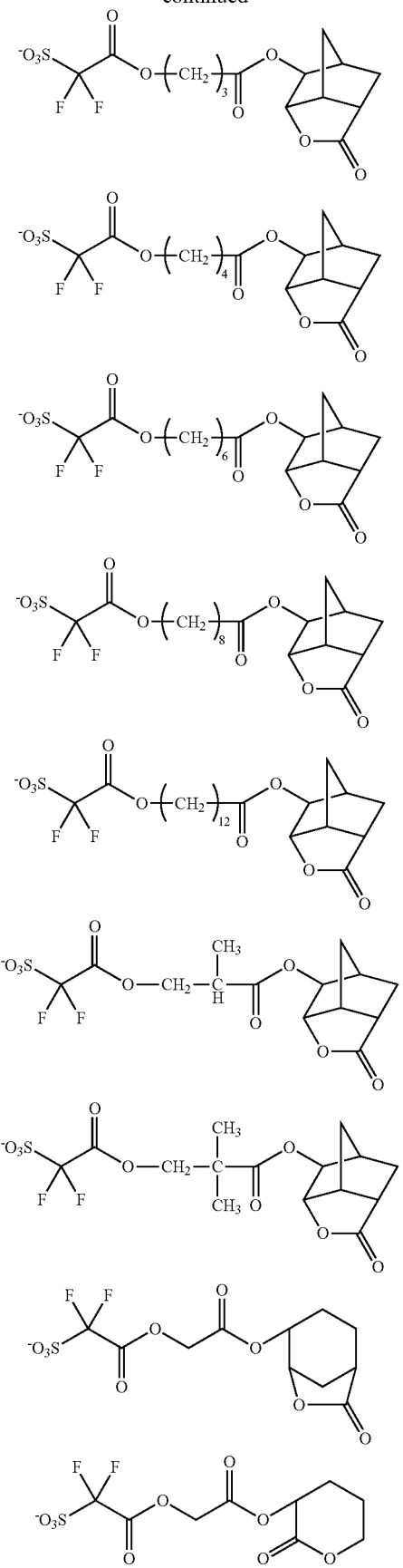
116
-continued
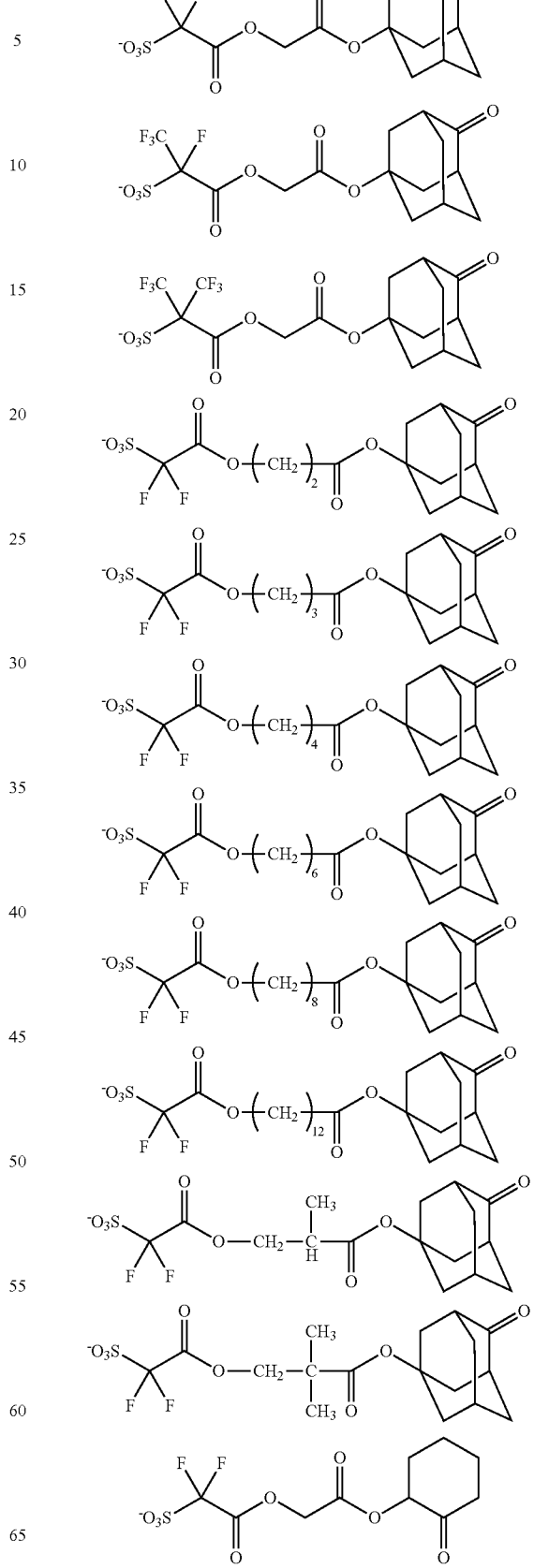

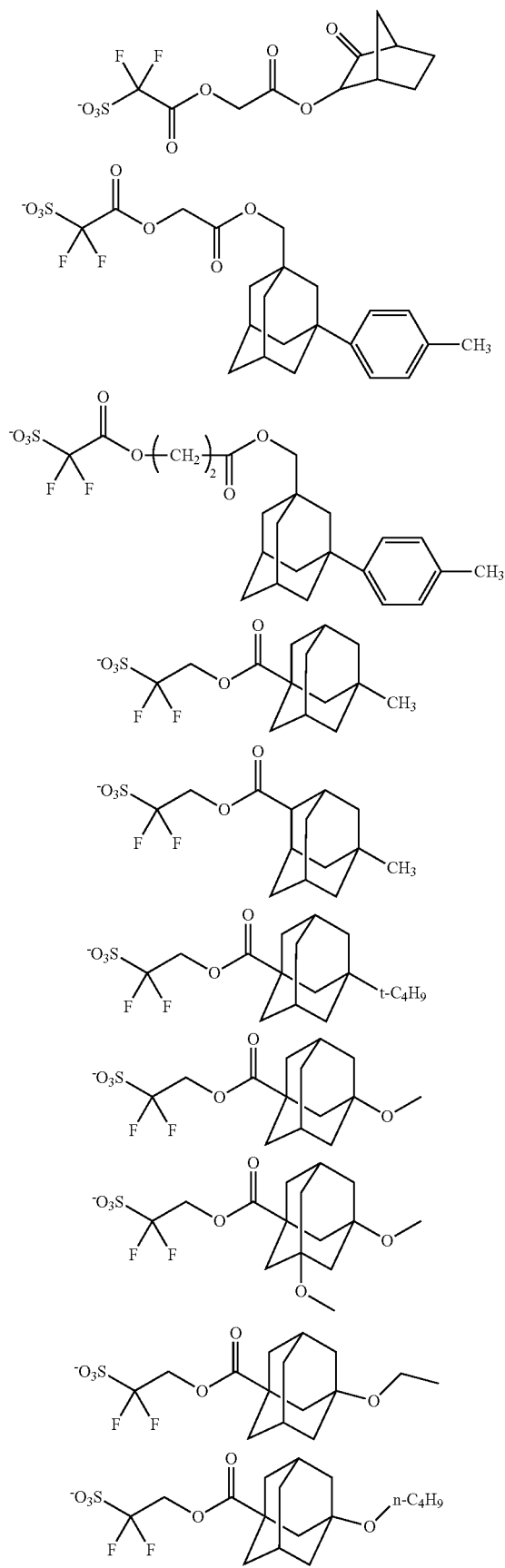
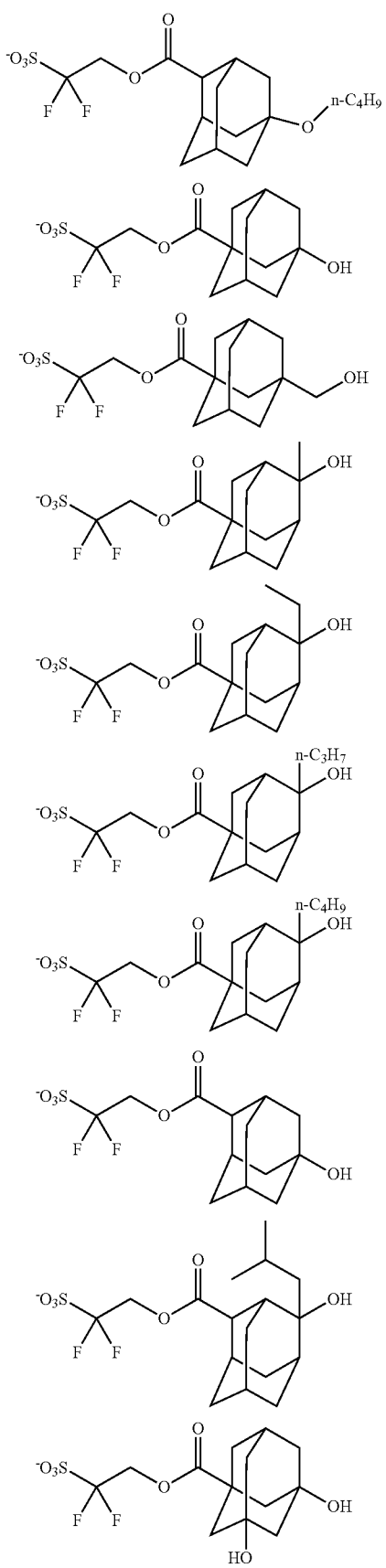

119
-continued
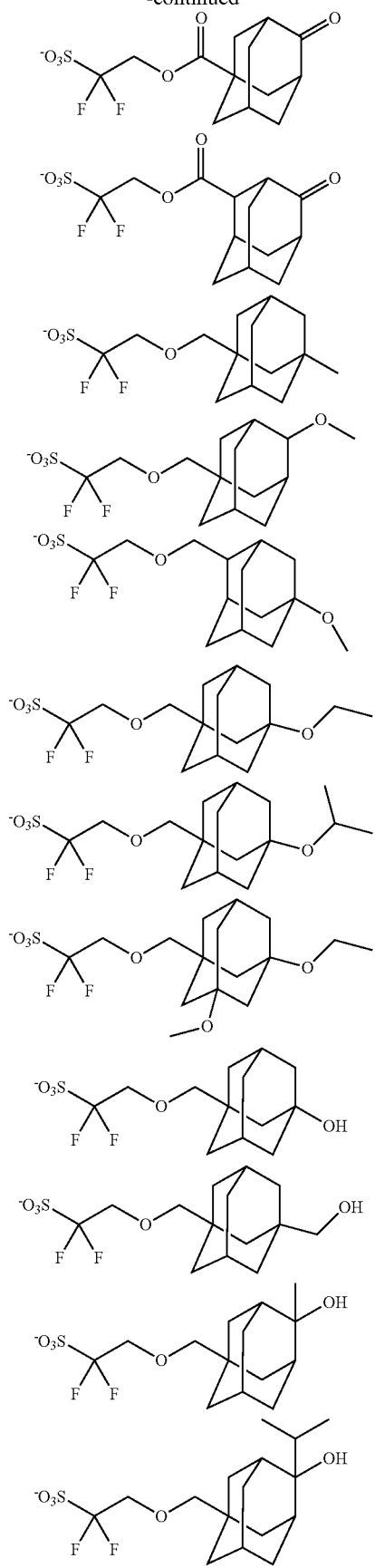
120
-continued
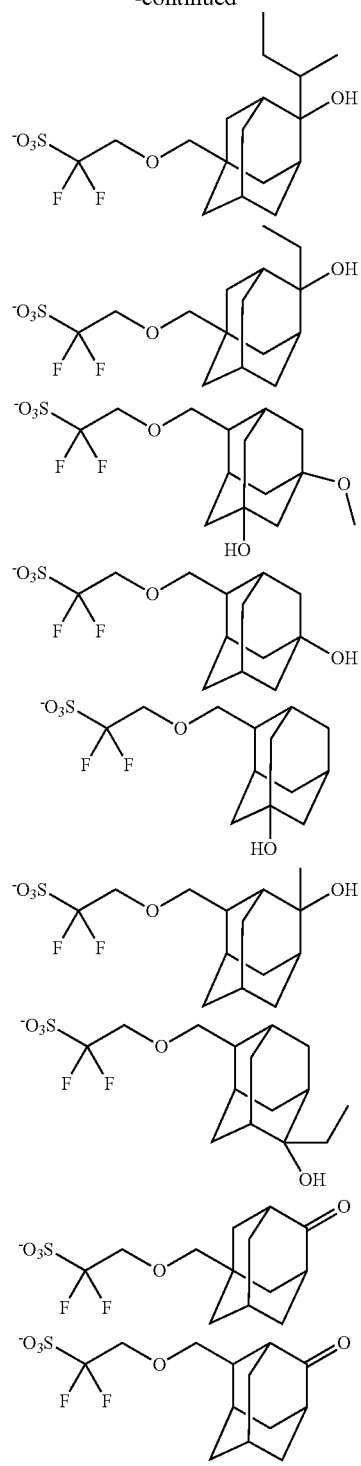
Among them, preferred are the following sulfonic anions.
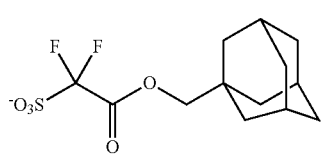

-continued

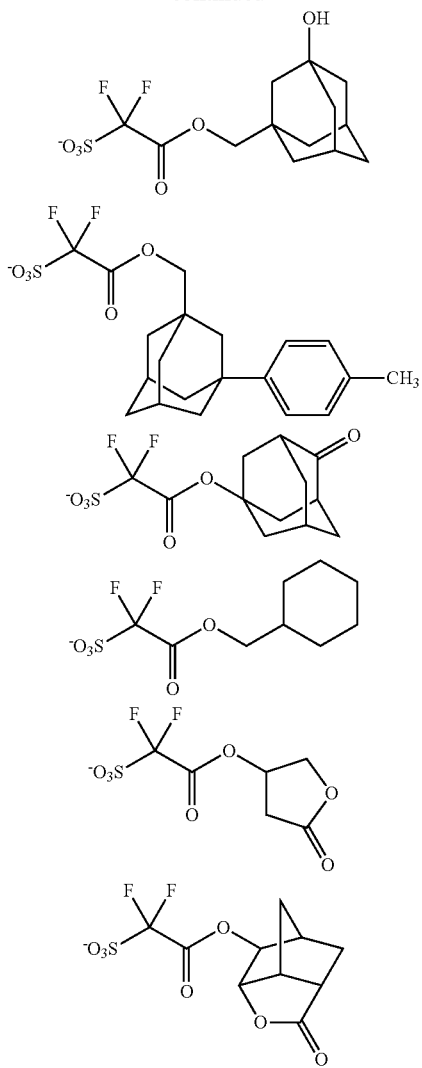

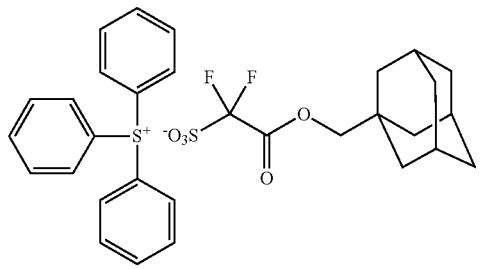
(B1-1)

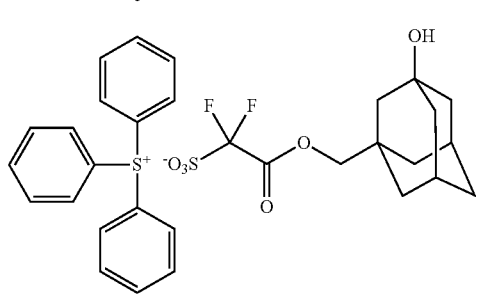
(B1-2)

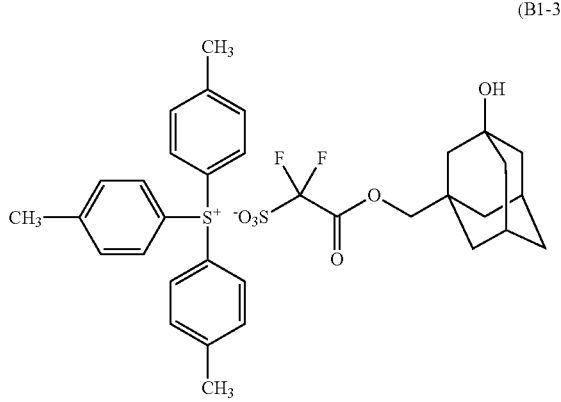
(B1-3)

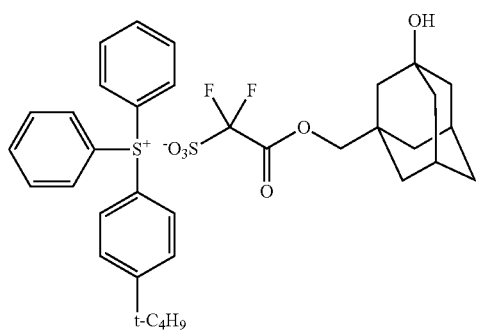
(B1-4)

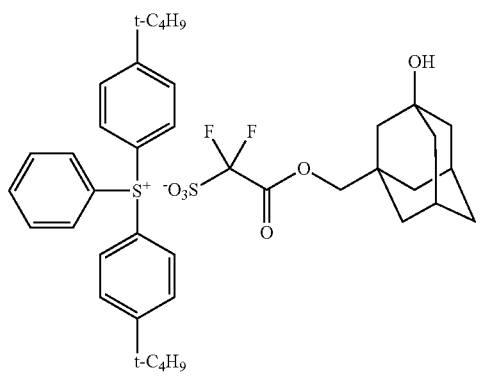
(B1-5)

Examples of the organic counter ion represented by $Z^+$ in the salt represented by the formula (B1) include the same as described in the above-mentioned $Z^{1+}$. Preferable examples of the cation represented by $Z^+$ include the cations represented by the formulae (b2-1) to (b2-4). Among them, preferred is the cation represented by the formula (b2-1), and more preferred is the cation represented by the formula (b2-1-1). A triphenylsulfonium cation is especially preferable.

Examples of the salt represented by the formula (B1) include a salt wherein the anion is any one of the abovementioned anion parts and the cation is any one of the abovementioned cation parts.

Preferable examples of the salt represented by the formula (B1) include a combination of any one of anions represented by the formulae (b1-1-1) to (b1-1-9) and the cation represented by the formulae (b2-1-1), and a combination of any one of anions represented by the formulae (b1-1-3) to (b1-1-5) and the cation represented by the formulae (b2-3).

The salt represented by the formulae (B1-1) to (B1-17) are preferable, and the salt represented by the formulae (B1-1), (B1-2), (B1-6), (B1-11), (B1-12), (81-13) and (B1-14) are more preferable, (B1-6)
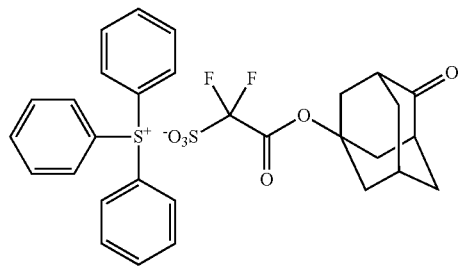
(B1-7)
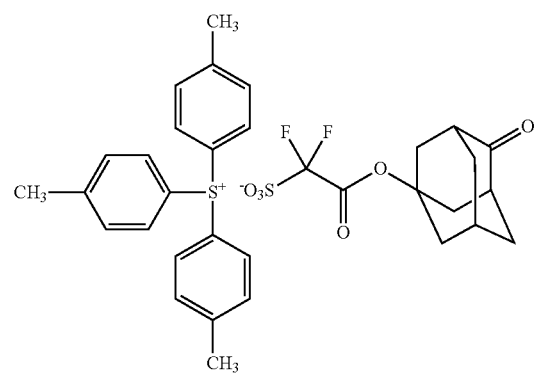
(B1-8)
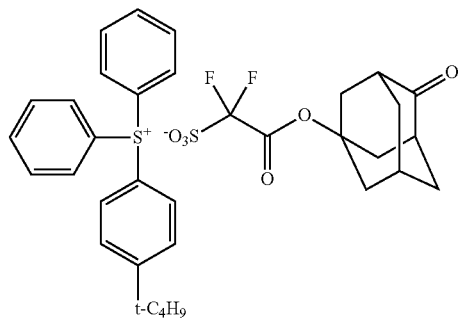
(B1-9)
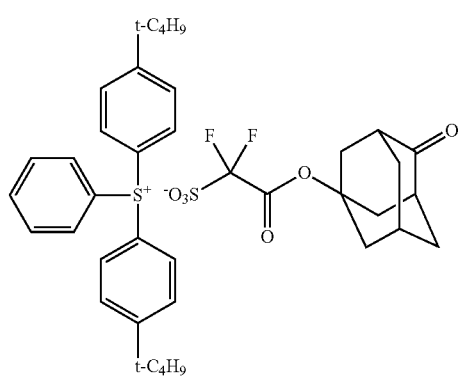
(B1-10)
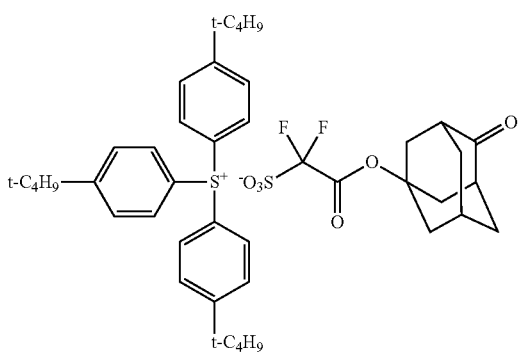
(B1-11)
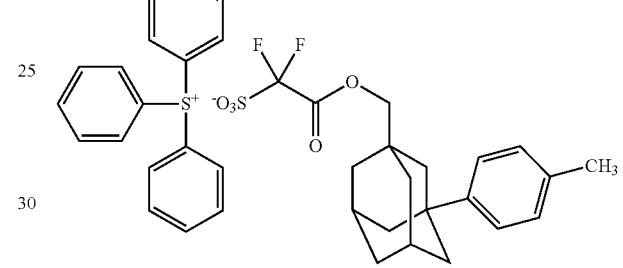
(B1-12)
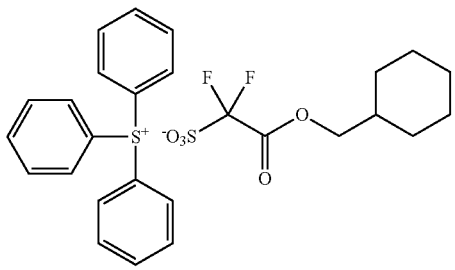
(B1-13)
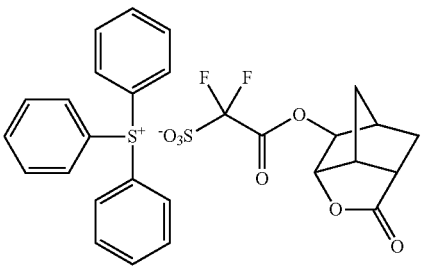
(B1-14)
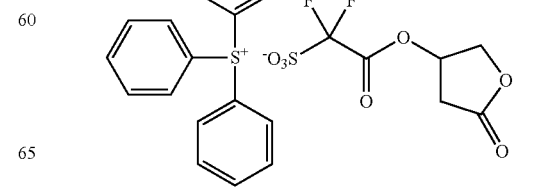

-continued

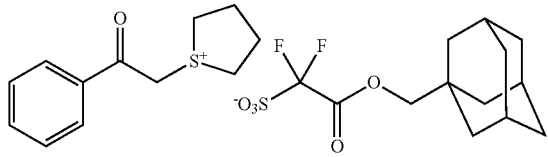
(B1-15)

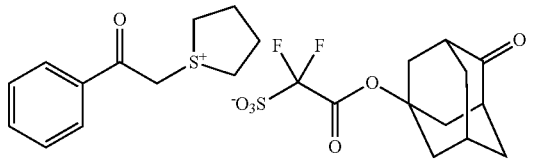
(B1-16)

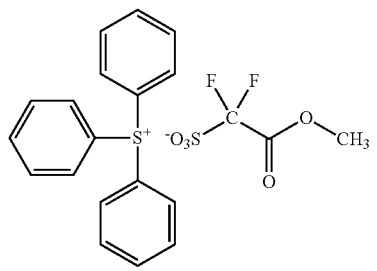
(B1-17)

Two or more kinds of the photoacid generator can be used in combination.

The content of the acid generator of the present invention is usually 1 part by weight or more and preferably 3 parts by weight or more per 100 parts by weight of the resin, and it is usually 30 parts by weight or less and preferably 25 parts by weight or less per 100 parts by weight of the resin.

The content of SALT (I) is usually 1 part by weight or more and preferably 3 parts by weight or more per 100 parts by weight of the resin, and it is usually 30 parts by weight or less and preferably 25 parts by weight or less per 100 parts by weight of the resin.

The content of acid generator other than SALT (I) in the first photoresist composition is usually 1 part by weight or more and preferably 3 parts by weight or more per 100 parts by weight of the resin, and it is usually 30 parts by weight or less and preferably 25 parts by weight or less per 100 parts by weight of the resin.

The second photoresist composition of the present invention comprises POLYMER (I). The second photoresist composition can contain one or more acid generators. Examples of the acid generator include SALT (I) and the acid generators other than SALT (I) as described in the above. The content of acid generator in the second photoresist composition is usually 1 part by weight or more and preferably 3 parts by weight or more per 100 parts by weight of POLYMER (I), and it is usually 30 parts by weight or less and preferably 25 parts by weight or less per 100 parts by weight of POLYMER (I).

The content of POLYMER (I) in the second photoresist composition of the present invention is usually 80% by weight or more based on 100% by weight of the solid component.

The first and second photoresist compositions of the present invention can contain a basic compound as a quencher.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2);

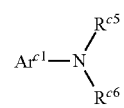
(C2)

wherein $Ar^{c1}$ represents an aromatic hydrocarbon group, and $R^{c5}$ and $R^{c6}$ independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

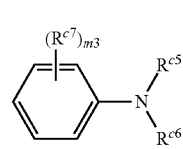
(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline Other examples of the basic compound include amines represented by the formulae (C3) to (C11):

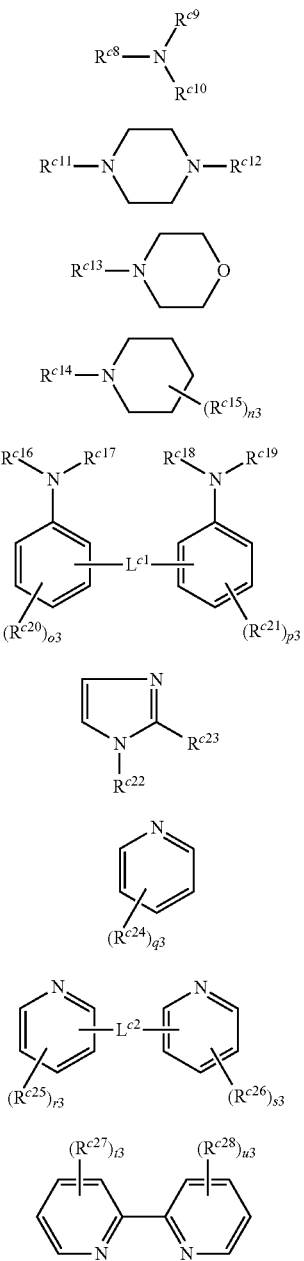

wherein $R^{c8}$, $R^{c20}$, $R^{c21}$, and $R^{c23}$ to $R^{c28}$ independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ independently represents a divalent aliphatic hydrocarbon group, —CO—, —C(=NH)—, —C(=NR$^{c3}$)—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldipentylamine, methyldihexylamine, methyldicyclohexylamine, methyldiheptylamine, methyldioctylamine, methyldinonylamine, methyldidecylamine, ethyldibutylamine, ethyldipentylamine, ethyldihexylamine, ethydiheptylamine, ethyldioctylamine, ethyldinonylamine, ethyldidecylamine, dicyclohexylmethylamine, tris[2- (2-methoxyethoxy)ethyl]amine, triisopropanolamine, ethylenediamine, tetramethylenediamine, hexamethylenediamine, 4,4'- diamino-1,2-diphenylethane, 4,4'- diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (CB) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the first and second photoresist compositions contain the basic compound, the content thereof is usually 0.01 to 1% by weight based on sum of solid component, respectively.

The first and second photoresist compositions of the present invention usually contain one or more solvents, respectively. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by weight or more, preferably 92% by weight or more preferably 94% by weight or more based on total amount of the photoresist composition of the present invention. The amount of the solvent is usually 99.9% by weight or less and preferably 99% by weight or less based on total amount of the photoresist composition of the present invention.

The first and second photoresist compositions of the present invention can contain, if necessary, a small amount of various additives such as a sensitizer, a dissolution inhibitor, other polymers, a surfactant, a stabilizer and a dye as long as the effect of the present invention is not prevented.

The first and second photoresist compositions of the present invention are useful for a chemically amplified photoresist composition A photoresist pattern can be produced by the following steps (1) to (5)

(1) a step of applying the first or second photoresist composition of the present invention on a substrate, (2) a step of forming a photoresist film by conducting drying, (3) a step of exposing the photoresist film to radiation, (4) a step of baking the exposed photoresist film, and (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having 0.2 μm of a pore size before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength; 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammoniumhydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern showing good Exposure Latitude (EL), and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for EUV lithography and EB lithography.

EXAMPLES

The present invention will be described more specifically by Examples, which are not construed to limit the scope of the present invention.

The "%" and "part(s)" used to represent the content of any component and the amount of any material used in the following examples and comparative examples are on a weight basis unless otherwise specifically noted. The weight-average molecular weight of any material used in the following examples is a value found by gel permeation chromatography [HLC-8120GPC Type, Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 μL] using standard polystyrene as a standard reference material. Structures of compounds were determined by mass spectrometry (Liquid Chromatography: 1100 Type, manufactured by AGILENT TECHNOLOGIES LTD., Mass Spectrometry: LC/MSD Type or LC/MSD TOF Type, manufactured by AGILENT TECHNOLOGIES LTD.).

Example 1

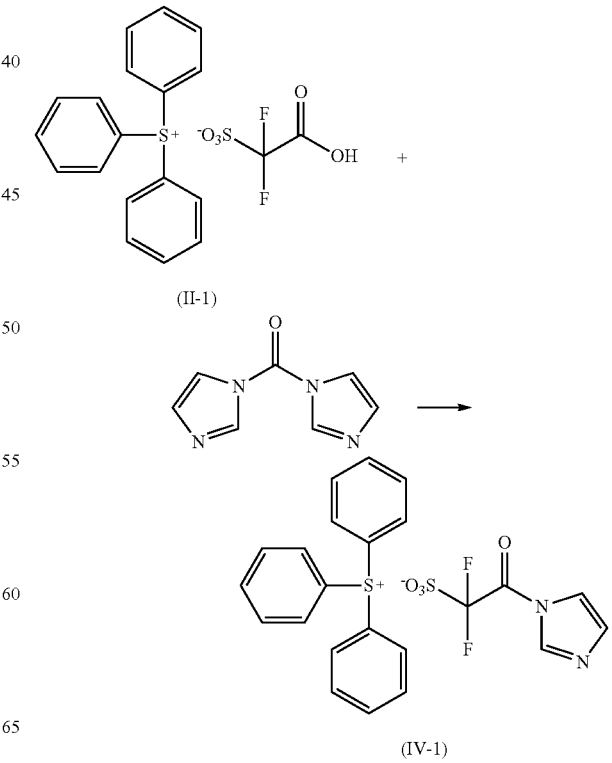

MS (ESI(+) Spectrum): M⁺ 263.1
MS (ESI(−) Spectrum): M⁻ 335.0

Example 2

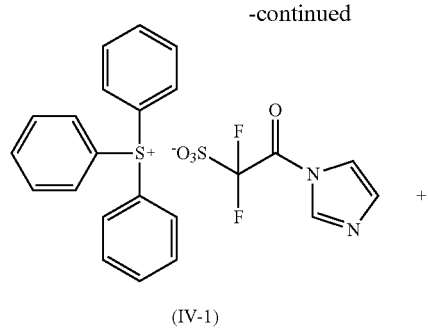
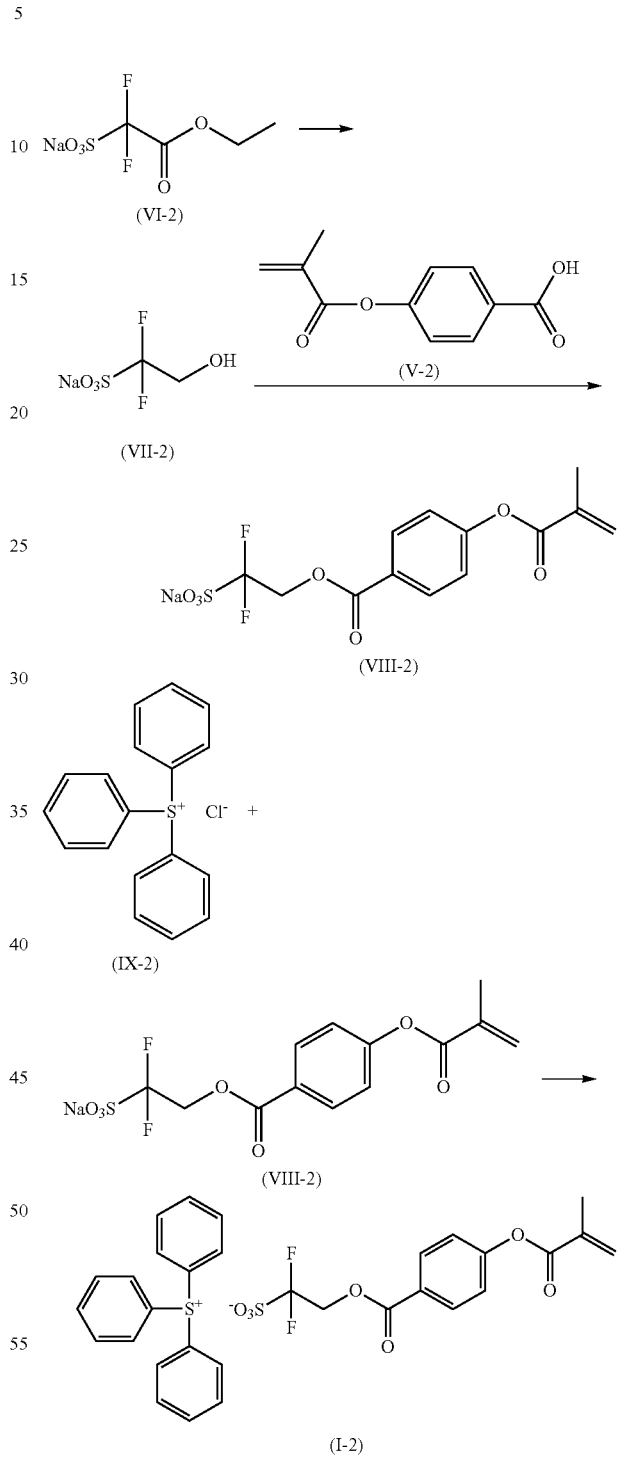

The salt represented by the formula (II-1) was prepared according to the method described in JP 2008-127367 A. A mixture of 10.00 parts of the salt represented by the formula (II-1), 50.00 parts of acetonitrile and 4.44 parts of carbonyldiimidazole which was available from Tokyo Chemical Industry Co., Ltd. was stirred at 80° C. for 30 minutes. The mixture obtained was cooled down to 23° C. and then, filtrated to obtain 59.57 parts of a solution containing the salt represented by the formula (IV-1).

A mixture of 59.57 parts of a solution containing the salt represented by the formula (IV-1) and 3.94 parts of p-hydroxyphenyl methacrylate which was available from Osaka Organic Chemical Industry Ltd. was stirred at 23° C. for 1 hour. The obtained reaction mixture was filtrated. The filtrate obtained was concentrated, and to the residue obtained, 100 parts of chloroform and 30 parts of ion-exchanged water were added. The resultant mixture was stirred for 30 minutes, and then, separated. The organic layer obtained was washed three times with ion-exchanged water. The organic layer obtained was concentrated to obtain 6.24 parts of a salt represented by the formula (I-1). This is called as Salt (I-1).

The mixture of 10.4 parts of lithium aluminum hydride and 120 parts of anhydrous tetrahydrofuran was stirred at 23° C. for 30 minutes. To the mixture, a solution prepared by dissolving 62.2 parts of a compound represented by the formula (B5-a) in 900 parts of tetrahydrofuran was added dropwise under cooling with ice-bath, and the resultant mixture was stirred at 23° C. for 5 hours. To the obtained reaction mixture, 50 parts of ethyl acetate and 50 parts of 6N hydrochloric acid were added to conduct separation. The organic layer obtained was concentrated and the residue obtained was purified with silica gel column chromatography (silica gel: silica gel 60-200 mesh available from Merck KGaA, solvent: chloroform/methanol=5/1) to obtain 84.7 parts of a compound represented by the formula (VII-2) of which purity was 60%.

A mixture of 36.90 parts of a compound represented by the formula (V-2) and 750 parts of anhydrous tetrahydrofuran was stirred at 23° C. for 30 minutes. To the mixture, a solution prepared by dissolving 28.90 parts of carbonyldiimidazole in 500 parts of anhydrous tetrahydrofuran was added dropwise at 23° C., and then, the resultant mixture was stirred at 23° C. for 4 hours. The obtained mixture was added dropwise into a mixture of 60.04 parts of the compound represented by the formula (VII-2) of which purity was 60% and 500 parts of anhydrous tetrahydrofuran, at 54 to 60° C. over 25 minutes. The resultant mixture was stirred at 65° C. for 18 hours, and then, cooled followed by filtration. The filtrate was concentrated and the residue obtained was purified with silica gel column chromatography (silica gel: silica gel 60-200 mesh available from Merck KGaA, solvent: chloroform/methanol=5/1) to obtain 26.24 parts of a compound represented by the formula (VIII-2).

A mixture of 10.30 parts of the compound represented by the formula (VIII-2) and 300 parts of chloroform was stirred at 23° C. for 30 minutes. To the mixture, 8.30 parts of a salt represented by the formula (IX-2) was added, and then, the resultant mixture was stirred at 23° C. for 12 hours followed by conducting separation. The obtained organic layer was washed three times with 100 parts of ion-exchanged water, and then, 5 parts of active carbon was added thereto to stir at 23° C. for 30 minutes followed by filtration. The filtrate obtained was concentrated, and to the residue obtained, 200 parts of acetonitrile was added to prepare a solution. The obtained solution was concentrated, and 200 parts of ethyl acetate was added to the obtained residue. The resultant mixture was stirred and then, the supernatant solution was removed from the mixture. To the obtained residue, 200 parts of tert-butyl methyl ether was added. The resultant mixture was stirred and then, the supernatant solution was removed from the mixture. The obtained residue was dissolved in chloroform, and the obtained solution was concentrated to obtain a residue. The residue was purified with silica gel column chromatography (silica gel: silica gel 60-200 mesh available from Merck KGaA, solvent: chloroform/methanol=5/1) to obtain 6.52 part of a salt represented by the formula (I-2). This is called as Salt I-2.

MS (ESI(+) Spectrum): M⁺ 263.1
MS (ESI(−) Spectrum): M⁻ 349.0

Example 3

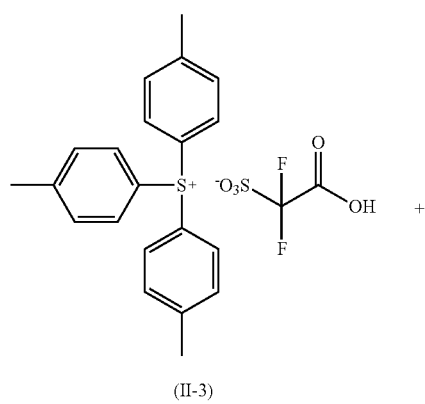

(II-3)

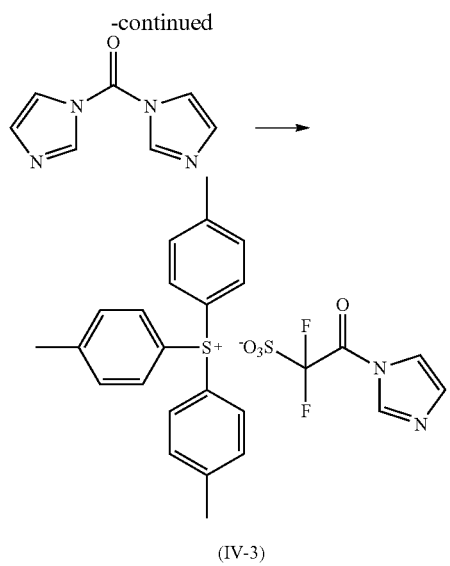

(IV-3)

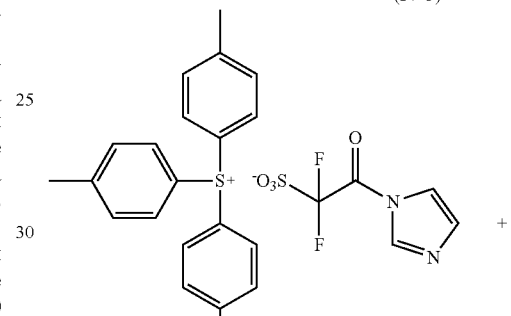

(IV-3)

(V-3)

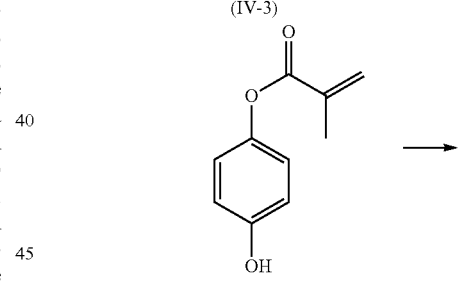

(I-3)

A mixture of 10.96 parts of the salt represented by the formula (II-3), 50.00 parts of acetonitrile and 4.44 parts of carbonyldiimidazole which was available from Tokyo Chemical Industry Co., Ltd. was stirred at 80° C. for 30 minutes. The mixture obtained was cooled down to 23° C. and then, filtrated to obtain 60.54 parts of a solution containing the salt represented by the formula (IV-3).

A mixture of 60.54 parts of a solution containing the salt represented by the formula (IV-3) and 3.94 parts of p-hydroxyphenyl methacrylate was stirred at 23° C. for 1 hour. The obtained reaction mixture was filtrated. The filtrate obtained was concentrated, and to the residue obtained, 100 parts of chloroform and 30 parts of ion-exchanged water were added. The resultant mixture was stirred for 30 minutes, and then, separated. The organic layer obtained was washed three times with ion-exchanged water. The organic layer obtained was concentrated to obtain 6.58 parts of a salt represented by the formula (I-3). This is called as Salt (I-3).

MS (ESI(+) Spectrum): M⁺ 305.1
MS (ESI(−) Spectrum): M⁻ 335.0

Example 4

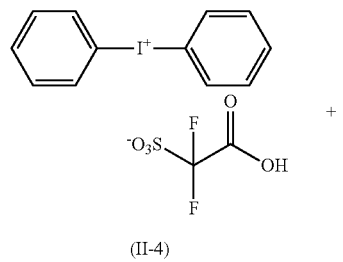

(II-4)

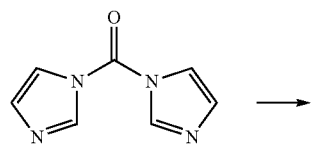

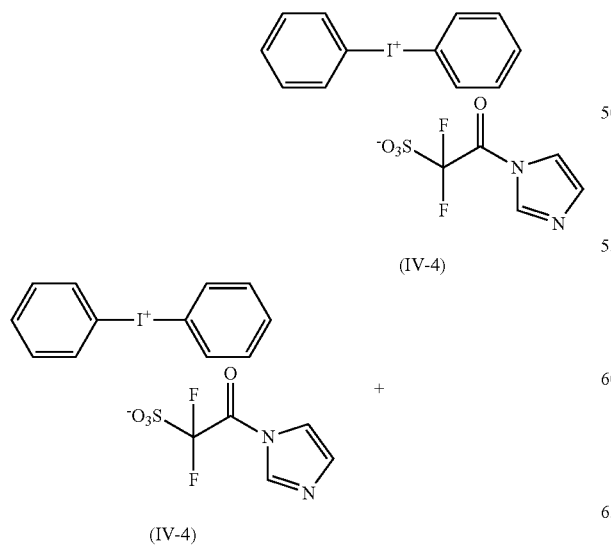

(IV-4)

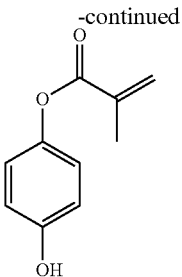

(V-4)

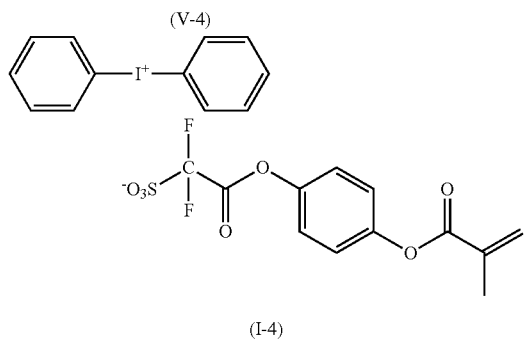

(I-4)

A mixture of 10.40 parts of the salt represented by the formula (II-4), 50.00 parts of acetonitrile and 4.44 parts of carbonyldiimidazole which was available from Tokyo Chemical Industry Co., Ltd. was stirred at 80° C. for 30 minutes. The mixture obtained was cooled down to 23° C. and then, filtrated to obtain 59.98 parts of a solution containing the salt represented by the formula (IV-4).

A mixture of 59.98 parts of a solution containing the salt represented by the formula (IV-4) and 3.94 parts of p-hydroxyphenyl methacrylate was stirred at 23° C. for 1 hour. The obtained reaction mixture was filtrated. The filtrate obtained was concentrated, and to the residue obtained, 100 parts of chloroform and 30 parts of ion-exchanged water were added. The resultant mixture was stirred for 30 minutes, and then, separated. The organic layer obtained was washed three times with ion-exchanged water. The organic layer obtained was concentrated to obtain 6.12 parts of a salt represented by the formula (I-4). This is called as Salt (I-4).

MS (ESI(+) Spectrum): M⁺ 281.0
MS (ESI(−) Spectrum): M⁻ 335.0

Example 5

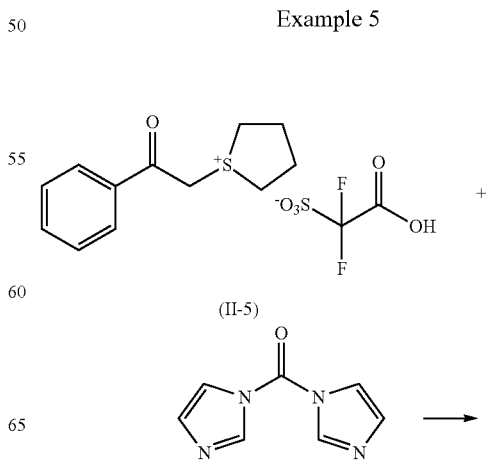

(II-5)

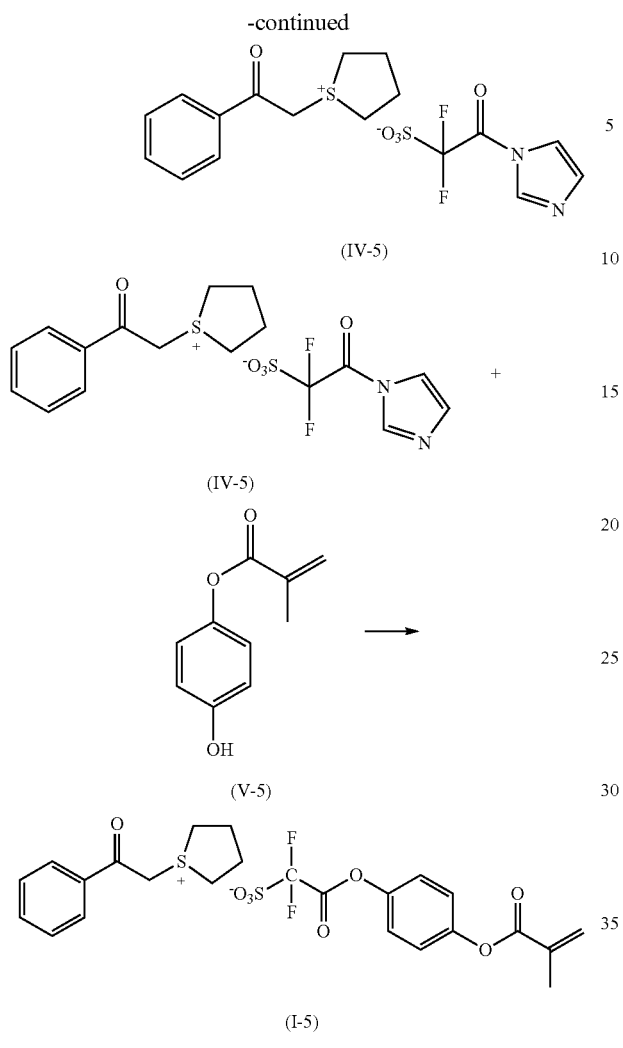

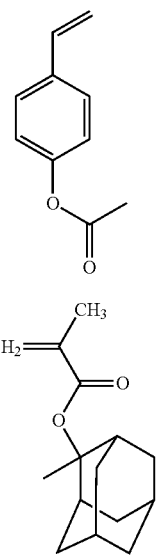

(A)

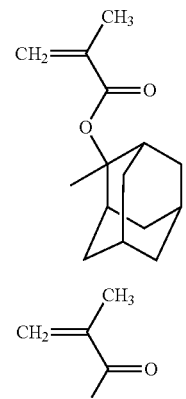

(B)

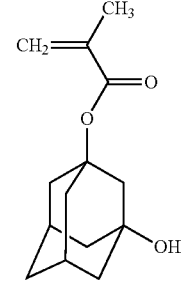

(C)

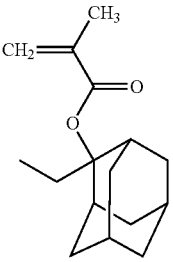

(D)

Example 6

A mixture of 8.72 parts of the salt represented by the formula (II-5), 50.00 parts of acetonitrile and 4.44 parts of carbonyldiimidazole which was available from Tokyo Chemical Industry Co., Ltd. was stirred at 80° C. for 30 minutes. The mixture obtained was cooled down to 23° C. and then, filtrated to obtain 58.24 parts of a solution containing the salt represented by the formula (IV-5).

A mixture of 58.24 parts of a solution containing the salt represented by the formula (IV-5) and 3.94 parts of p-hydroxyphenyl methacrylate was stirred at 23° C. for 1 hour. The obtained reaction mixture was filtrated. The filtrate obtained was concentrated, and to the residue obtained, 100 parts of chloroform and 30 parts of ion-exchanged water were added. The resultant mixture was stirred for 30 minutes, and then, separated. The organic layer obtained was washed three times with ion-exchanged water. The organic layer obtained was concentrated to obtain 5.29 parts of a salt represented by the formula (I-5). This is called as Salt (I-5).

MS (ESI(+) Spectrum): M$^+$ 207.1

MS (ESI(−) Spectrum): M$^-$ 335.0

In the following Examples and Resin Synthesis Examples, Monomer (A), Monomer (B), Monomer (C) and Monomer (D) represented by the followings were used in addition to the salts prepared in the above.

Fifteen (15) parts of Monomer (A), 11.82 parts of Monomer (B), 3.97 parts of Monomer (C) and 5.03 parts of Salt (I-1) were mixed (molar ratio: Monomer (A)/Monomer (B)/Monomer (C)/Salt (I-1)=55/30/10/5), and 71.66 parts of methyl ethyl ketone was added thereto. To the resultant mixture, 3.31 parts of azobisisobutyronitrile as an initiator (ratio based on all monomer molar amount was 12 mol %) was added, and the obtained mixture was refluxed for 12 hours. The reaction mixture obtained was poured into a large amount of mixed solvent of methanol and water (methanol/water=3/1) to cause precipitation. This operation was repeated three times for purification to obtain a copolymer.

The obtained copolymer and 3.58 parts of 4-dimethylaminopyridine (ratio based on all monomer molar amount was 10%) were mixed with 107.48 parts of methanol, and the resultant mixture was refluxed for 20 hours. The obtained mixture was cooled and then, was neutralized with 4.49 parts of glacial acetic acid. The obtained mixture was poured into excess amount of water to cause precipitation. The precipitate was collected by filtration and dissolved in acetone. The obtained solution was poured into excess amount of water to cause precipitation, and the precipitate was collected by filtration. This operation was repeated three times to obtain 24.59 parts of a polymer having a weight-average molecular weight of about $3.0 \times 10^3$. This polymer had the structural units represented by the followings. This polymer called as Polymer D1.

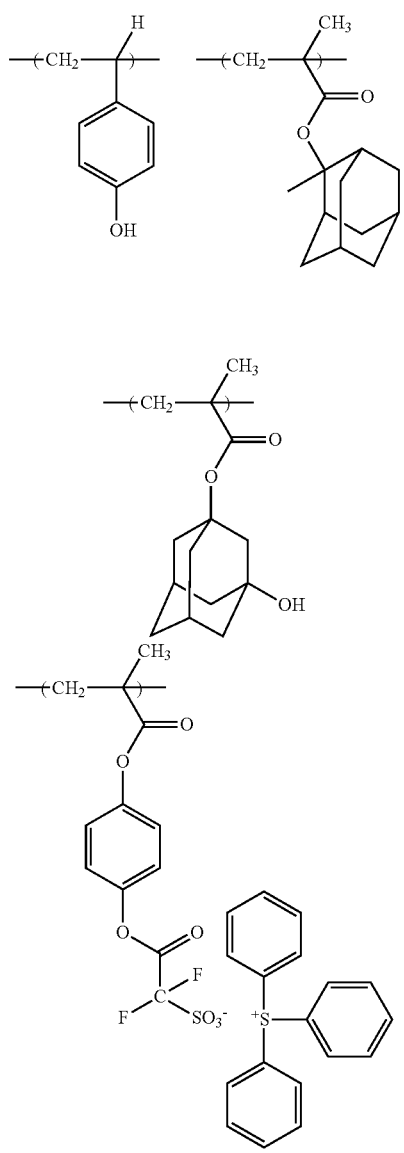

Example 7

The polymerization was conducted according to the same as described in Example 6 except that 5.15 parts of Salt (I-2) was used in place of 5.03 parts of Salt (I-1) to obtain 24.46 parts of a polymer having a weight-average molecular weight of about $4.0 \times 10^3$. This polymer had the structural units represented by the followings. This polymer is called as Polymer D2.

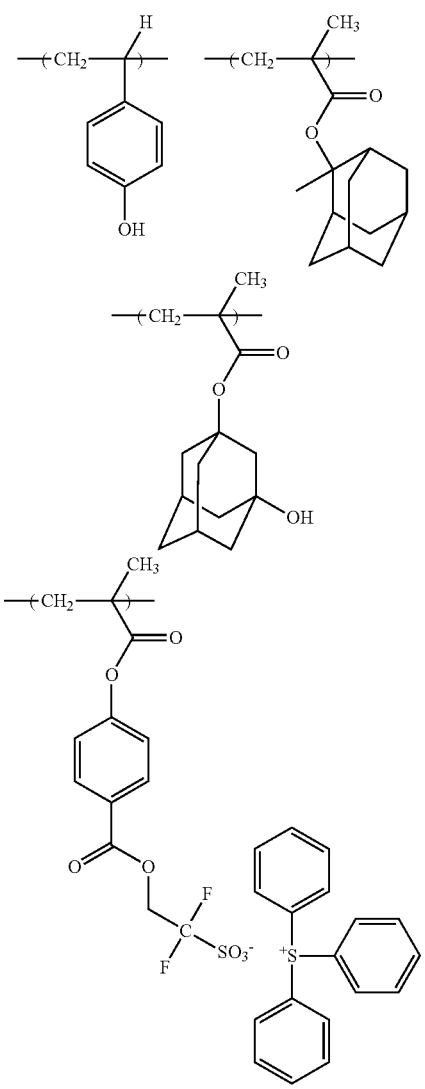

Example 8

The polymerization was conducted according to the same as described in Example 6 except that 5.38 parts of Salt (I-3) was used in place of 5.03 parts of Salt (I-1) to obtain 24.68 parts of a polymer having a weight-average molecular weight of about $3.9 \times 10^3$. This polymer had the structural units represented by the followings. This polymer is called as Polymer D3.

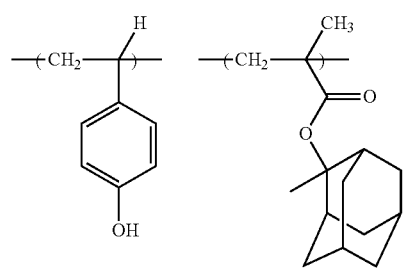

-continued

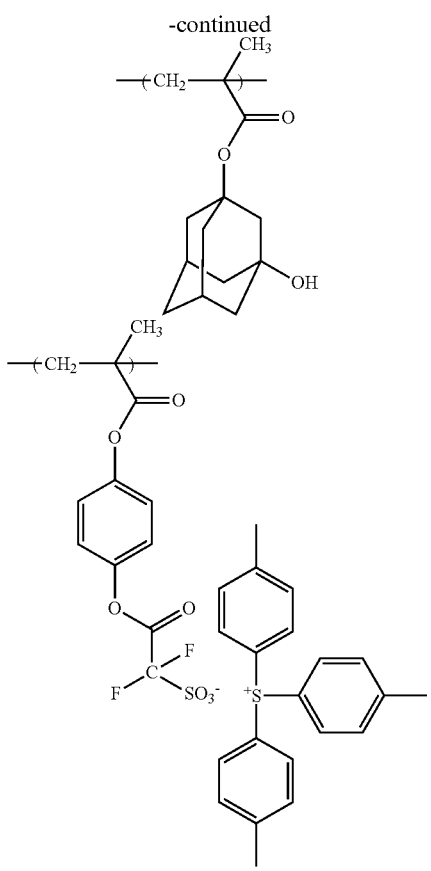

Example 9

The polymerization was conducted according to the same as described in Example 6 except that 5.18 parts of Salt (I-4) was used in place of 5.03 parts of Salt (I-1) to obtain 21.86 parts of a polymer having a weight-average molecular weight of about 4.2×10. This polymer had the structural units represented by the followings. This polymer is called as Polymer b4.

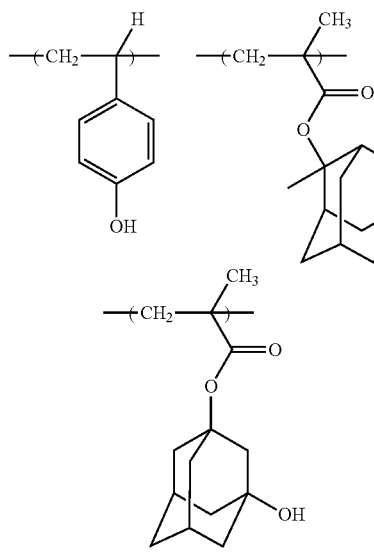

-continued

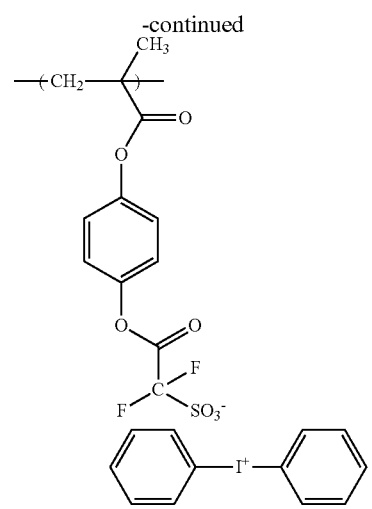

Example 10

The polymerization was conducted according to the same as described in Example 6 except that 4.56 parts of Salt (I-5) was used in place of 5.03 parts of Salt (I-1) to obtain 18.12 parts of a polymer having a weight-average molecular weight of about $4.4 \times 10^3$. This polymer had the structural units represented by the followings. This polymer is called as Polymer D5.

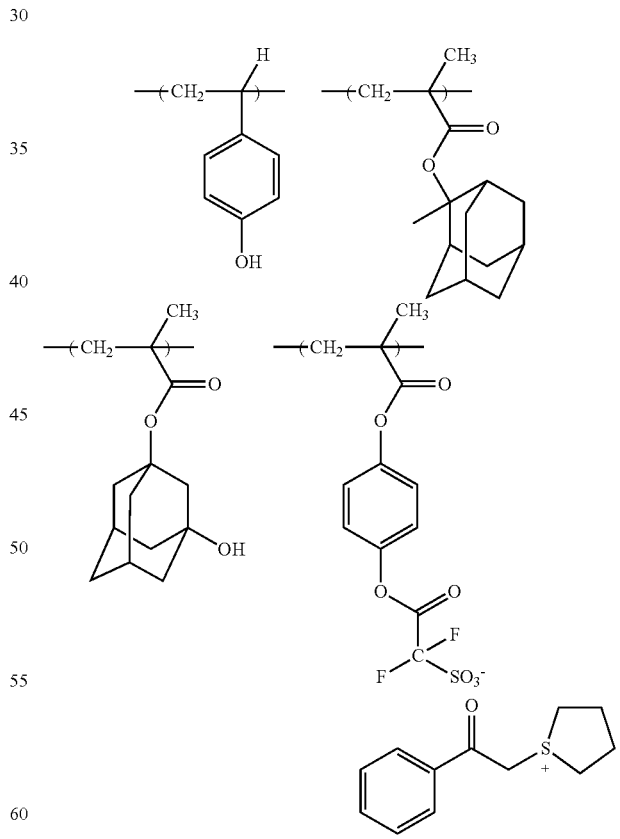

Resin Synthesis Example 1

A solution prepared by dissolving 39.7 parts of Monomer (D) and 103.8 parts of Monomer (A) in 265 parts of isopropanol was heated up to 75° C. under an nitrogen atmosphere.

To a solution, a solution prepared by dissolving 11.05 parts of dimethyl 2,2-azobis(2-methylpropionate) in 22.11 parts of isopropanol was added dropwise, and the resultant mixture was refluxed for 12 hours. The obtained reaction mixture was cooled, and then, was poured into a large amount of methanol to cause precipitation. The precipitate was collected by filtration to obtain 250 parts of a copolymer. The obtained copolymer and 10.3 parts of 4-dimethylaminopyridine were mixed with 202 parts of methanol, and the resultant mixture was refluxed for 20 hours. The obtained mixture was cooled and then, was neutralized with 7.6 parts of glacial acetic acid. The obtained mixture was poured into excess amount of water to cause precipitation. The precipitate was collected by filtration and dissolved in acetone. The obtained solution was poured into excess amount of water to cause precipitation, and the precipitate was collected by filtration. This operation was repeated three times to obtain 95.9 parts of a resin having a weight-average molecular weight of about $8.6 \times 10^3$. This resin had the structural units represented by the followings. This resin is called as Resin A1. The ratio of the structural unit derived from Monomer (D) to Monomer (A) was about 20/80.

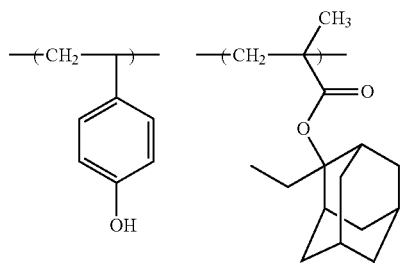

Resin Synthesis Example 2

The polymerization was conducted according to the same as described in Resin Synthesis Example 1 except that 59.6 parts of Monomer (D) was used in place of 39.7 parts of Monomer (D) and 90.8 parts of Monomer (A) was used in place of 103.8 parts of Monomer (A) to obtain 102.8 parts of a resin having a weight-average molecular weight of about $8.2 \times 10^3$. This resin had the structural units represented by the followings. This resin is called as Resin A2.

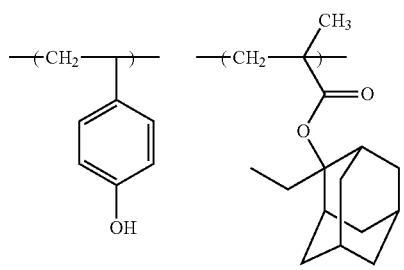

Examples 11 to 19 and Comparative Example 1

Resin

Resin A1, A2
<Polymer>
D1: Polymer D1
D2: Polymer D2
D3: Polymer D3
D4: Polymer D4
D5: Polymer D5
<Acid Generator>
I-1: Salt (I-1)
I-2: Salt (I-2)
B1:

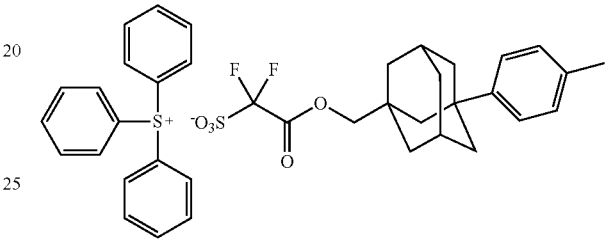

B2: triphenylsulfonium 2,4,6-triisopropylbenzenesulfonate
B3: bis(cyclohexylsulfonium)diazomethane
<Quencher>
C1: 2,6-diisopropylaniline
C2: tetrabutylammonium hydroxide
<Solvent>
E1: propylene glycol monomethyl ether acetate 400 parts
propylene glycol monomethylether 100 parts
γ-butyrolactone 5 parts The following components were mixed and dissolved, further, filtrated through a fluorine resin filter having pore diameter of 0.2 μm, to prepare photoresist compositions.
Resin (kind and amount are described in Table 1)
Polymer (kind and amount are described in Table 1)
Acid generator (kind and amount are described in Table 1)
Quencher (kind and amount are described in Table 1)
Solvent E1

TABLE 1

| Ex. No. | Resin (kind/amount (part)) | Polymer (kind/amount (part)) | Acid generator (kind/amount (part)) | Quencher (kind/amount (part)) |
|---|---|---|---|---|
| Ex. 11 | A1/6.75 A2/6.75 | — | I-1/1.20 | C1/0.03 C2/0.03 |
| Ex. 12 | — | D1/10 | — | C1/0.03 C2/0.03 |
| Ex. 13 | — | D1/10 | B1/0.80 | C1/0.03 C2/0.03 |
| Ex. 14 | A1/6.75 A2/6.75 | — | I-2/1.20 | C1/0.03 C2/0.03 |
| Ex. 15 | — | D2/10 | — | C1/0.03 C2/0.03 |
| Ex. 16 | — | D2/10 | B1/0.80 | C1/0.03 C2/0.03 |
| Ex. 17 | — | D3/10 | — | C1/0.03 C2/0.03 |
| Ex. 18 | — | D4/10 | — | C1/0.03 C2/0.03 |
| Ex. 19 | — | D5/10 | — | C1/0.03 C2/0.03 |

TABLE 1-continued

| Ex. No. | Resin (kind/amount (part)) | Polymer (kind/amount (part)) | Acid generator (kind/amount (part)) | Quencher (kind/amount (part)) |
|---|---|---|---|---|
| Comp. Ex. 1 | A1/6.75 A2/6.75 | — | B2/0.45 B3/0.60 | C1/0.049 |

Silicon wafers were each contacted with hexamethyldisilazane at 90° C. for 60 seconds on a direct hot plate and each of the photoresist compositions prepared as above was spin-coated over the silicon wafer to give a film thickness after drying of 0.06 pin. After application of each of the photoresist compositions, the silicon wafers thus coated with the respective resist compositions were each prebaked on a direct hotplate at a temperature shown in column "PB" in Table 2 for 60 seconds. Using a writing electron beam lithography system ("HL-800D" manufactured by Hitachi, Ltd., 50 KeV), each wafer on which the respective resist film had been thus formed was exposed to a line and space pattern, while changing stepwise the exposure quantity.

After the exposure, each wafer was subjected to post-exposure baking on a hotplate at a temperature shown in column "PEB" in Table 2 for 60 seconds and then to paddle development with an aqueous solution of 2.38% by weight tetramethylammonium hydroxide for 60 seconds.

Each of a photoresist pattern developed on the silicon substrate after the development was observed with a scanning electron microscope, and the results of which are shown in Table 2.

Resolution: The amount of exposure that each photoresist pattern of the line width of 100 nm became 1:1 line and space pattern was as effective sensitivity. When line and space pattern having the line width of 70 nm was developed at effective sensitivity, resolution is good and its evaluation is marked by "◯", and when line and space pattern having the line width of 70 nm was not developed at effective sensitivity, resolution is bad and its evaluation is marked by "X".

TABLE 2

| Ex. No. | PB (° C.)/PEB (° C.) | Resolution |
|---|---|---|
| Ex. 11 | 110/110 | ◯ |
| Ex. 12 | 110/110 | ◯ |
| Ex. 13 | 110/110 | ◯ |
| Ex. 14 | 110/110 | ◯ |
| Ex. 15 | 110/110 | ◯ |
| Ex. 16 | 110/110 | ◯ |
| Ex. 17 | 110/110 | ◯ |
| Ex. 18 | 110/110 | ◯ |
| Ex. 19 | 110/110 | ◯ |
| Comp. Ex. 1 | 110/110 | X |

Silicon wafer was contacted with hexamethyldisilazane at 90° C. for 60 seconds on a direct hot plate and the photoresist composition prepared in Example 12, Example 15 or Comparative Example 1 was spin-coated over the silicon wafer to give a film thickness after drying of 0.05 μm, After application of the photoresist composition, the silicon wafer thus coated with the photoresist composition was prebaked on a direct hotplate at a temperature shown in column "PB" in Table 3 for 60 seconds. Using an EUV (extreme ultraviolet) exposure system, each wafer on which the respective resist film had been thus formed was exposed to a line and space pattern, while changing stepwise the exposure quantity.

After the exposure, each wafer was subjected to post-exposure baking on a hotplate at a temperature shown in column "PEB" in Table 3 for 60 seconds and then to paddle development with an aqueous solution of 2.30% by weight tetramethylammonium hydroxide for 60 seconds.

The pattern developed on the silicon substrate after the development was observed with a scanning electron microscope, and the results of which are shown in Table 3.

Resolution: The amount of exposure that the photoresist pattern of the line width of 50 nm became 1:1 line and space pattern was as effective sensitivity. When line and space pattern having the line width of 40 nm was developed at effective sensitivity, resolution is good and its evaluation is marked by "◯", and when line and space pattern having the line width of 40 nm was not developed at effective sensitivity, resolution is bad and its evaluation is marked by "X".

TABLE 3

| Ex. No. | PB (° C.)/PEB (° C.) | Resolution |
|---|---|---|
| Ex. 12 | 110/110 | ◯ |
| Ex. 15 | 110/110 | ◯ |
| Comp. Ex. 1 | 110/110 | X |

The salt of the present invention is suitable for an acid generator and the photoresist composition comprising the salt of the present invention provides a good photoresist pattern having good resolution.

What is claimed is:

1. A salt represented by the formula (I):

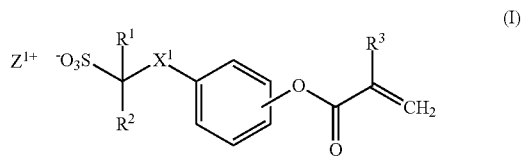

wherein $R^1$ and $R^2$ each independently represent a fluorine atom or a C1-C6 perfluoroalkyl group, $X^1$ represents *—CO—O—$L^{b2}$-, *—CO—O—$L^{b4}$-CO—O—$L^{b3}$-, *—CO—O—$L^{b8}$-O—, and *—CO—O—$L^{b10}$-O—$L^{b9}$-CO—O— where $L^{b2}$ represents a single bond or a C1-C15 saturated hydrocarbon group, $L^{b3}$ represents a single bond or a C1-C12 saturated hydrocarbon group, $L^{b4}$ represents a C1-C13 saturated hydrocarbon group, with the proviso that total carbon number of $L^{b3}$ and $L^{b4}$ is 1 to 13, $L^{b8}$ represents a C1-C14 saturated hydrocarbon group, $L^{b9}$ represents a C1-C11 saturated hydrocarbon group, $L^{b10}$ represents a C1-C11 saturated hydrocarbon group, with the proviso that total carbon number of $L^{b9}$ and $L^{b10}$ is 1 to 12, and * represents a binding position to —C($R^1$)($R^2$)—, and
$R^3$ represents a hydrogen atom or a methyl group, and $Z^{1+}$ represents an organic counter cation.

2. The salt according to claim 1, wherein $X^1$ is *—CO—O— in which * represents a binding position to —C($R^1$)($R^2$)—.

3. The salt according to claim 1, wherein $Z^{1+}$ is a triarylsulfonium cation.

4. An acid generator comprising the salt according to claim 1.

5. A polymer comprising a structural unit derived from the salt according to claim 1.

6. A photoresist composition comprising the acid generator according to claim 4.

7. A photoresist composition comprising the polymer according to claim 5.

8. The photoresist composition according to claim 6 or 7, which further comprises a basic compound.

9. A process for producing a photoresist pattern comprising the following steps (1) to (5):
   (1) a step of applying the photoresist composition according to claim 6 or 7 on a substrate,
   (2) a step of forming a photoresist film by conducting drying,
   (3) a step of exposing the photoresist film to radiation,
   (4) a step of baking the exposed photoresist film, and
   (5) a step of developing the baked photoresist film with an alkaline developer, thereby forming a photoresist pattern.

* * * * *